US011944676B2

(12) United States Patent
Sayre et al.

(10) Patent No.: US 11,944,676 B2
(45) Date of Patent: Apr. 2, 2024

(54) SYSTEMS AND METHODS FOR THE CONTROL OF ACUTE HEPATOPANCREATIC NECROSIS DISEASE

(71) Applicant: Pebble Labs Inc., Los Alamos, NM (US)

(72) Inventors: Richard Sayre, Los Alamos, NM (US); Tatiana Vinogradova-Shah, Rochester, NY (US); Elena Sineva, Bernalillo, NM (US)

(73) Assignee: Pebble Labs Inc., Los Alamos, NM (US)

( * ) Notice: Subject to any disclaimer, the term of this patent is extended or adjusted under 35 U.S.C. 154(b) by 980 days.

(21) Appl. No.: 16/637,612

(22) PCT Filed: Aug. 7, 2018

(86) PCT No.: PCT/US2018/045687

§ 371 (c)(1),
(2) Date: Feb. 7, 2020

(87) PCT Pub. No.: WO2019/032629

PCT Pub. Date: Feb. 14, 2019

(65) Prior Publication Data

US 2020/0178566 A1 Jun. 11, 2020

Related U.S. Application Data

(63) Continuation-in-part of application No. PCT/US2018/033976, filed on May 22, 2018, and a continuation-in-part of application No. PCT/US2018/025766, filed on Apr. 2, 2018.

(60) Provisional application No. 62/541,824, filed on Aug. 7, 2017.

(51) Int. Cl.

| | |
|---|---|
| ***A61K 39/02*** | (2006.01) |
| ***A01N 63/60*** | (2020.01) |
| ***A23K 10/16*** | (2016.01) |
| ***A23K 50/80*** | (2016.01) |
| ***A61K 35/741*** | (2015.01) |
| ***C12N 15/113*** | (2010.01) |
| ***C12N 15/52*** | (2006.01) |
| ***C12N 15/63*** | (2006.01) |

(52) U.S. Cl.

CPC ............ *A61K 39/107* (2013.01); *A01N 63/60* (2020.01); *A23K 10/16* (2016.05); *A23K 50/80* (2016.05); *A61K 35/741* (2013.01); *C12N 15/113* (2013.01); *C12N 15/52* (2013.01); *C12N 15/63* (2013.01); *C12N 2310/11* (2013.01)

(58) Field of Classification Search

CPC ............ A61K 39/107; A61K 2039/542; A61K 2039/523; A23K 10/16; C12N 15/113; C12N 15/63; C12N 2310/11

USPC ..................... 435/6.1, 91.1, 91.31, 455, 458; 514/44 A, 44 R; 546/23.1, 24.5

See application file for complete search history.

(56) References Cited

U.S. PATENT DOCUMENTS

| | | | |
|---|---|---|---|
| 5,294,533 | A | 3/1994 | Lupski et al. |
| 2005/0080032 | A1 | 4/2005 | Gross et al. |
| 2005/0130921 | A1 | 6/2005 | Waldor et al. |
| 2005/0158326 | A1 | 7/2005 | Chen et al. |
| 2005/0227933 | A1 | 10/2005 | Benkovic et al. |
| 2006/0269951 | A1 | 11/2006 | Taga et al. |
| 2008/0194504 | A1 | 8/2008 | Kyle et al. |
| 2010/0092428 | A1 | 4/2010 | Schmidt et al. |
| 2011/0158946 | A1 | 6/2011 | Durvasula et al. |
| 2014/0038296 | A1 | 2/2014 | Palsson et al. |
| 2014/0213779 | A1 | 7/2014 | Dixon et al. |
| 2014/0271559 | A1 | 9/2014 | Baum et al. |
| 2014/0371295 | A1 | 12/2014 | Loy et al. |
| 2015/0125545 | A1 | 5/2015 | Kolstad et al. |
| 2016/0281053 | A1 | 9/2016 | Sorek et al. |

FOREIGN PATENT DOCUMENTS

| | | | |
|---|---|---|---|
| CN | 103403146 | | 11/2015 |
| WO | 2005/079236 | A2 | 9/2005 |
| WO | 2012105805 | A2 | 8/2012 |
| WO | 2012105808 | A2 | 8/2012 |
| WO | 2018184029 | | 10/2014 |
| WO | 2018053451 | A1 | 3/2018 |
| WO | 2018217819 | | 11/2018 |
| WO | 2019032629 | | 2/2019 |

OTHER PUBLICATIONS

Defoirdt, T. (Reviews in Aquaculture, vol. 6, pp. 100-114 (2014)) (Year: 2014).*

Taga et al.(Molecular Microbiology, vol. 42, No. 3, pp. 777-793 (2001) (Year: 2001).*

Mei et al.(Applied and Environmental Micro biology, vol. 76, No. 15, pp. 4933-4942 (2010)) (Year: 2010).*

(Continued)

*Primary Examiner* — Jane J Zara

(74) *Attorney, Agent, or Firm* — Hovey Williams LLP; Crissa A. Cook

(57) ABSTRACT

Generally, the inventive technology relates to novel strategies for disease control in animal systems. Specifically, the inventive technology relates to novel methods, systems and compositions for the biocontrol of pathogens in aquatic systems. Specifically, the invention may comprise novel techniques, systems, and methods for the biocontrol of disease-transmitting pathogens affecting shrimp in aquaculture systems.

15 Claims, 22 Drawing Sheets

Specification includes a Sequence Listing.

(56) References Cited

OTHER PUBLICATIONS

Thammasorn et al.(Aquacult Int, vol. 25, pp. 1679-1692 (2017)) (Year: 2017).*
Subhadra et al (J. Applied Microbiology, vol. 108, pp. 831-849 (2010)). (Year: 2010).*
The Written Opinion of Intellectual Property Office of Singapore in Application No. 11202001143Y dated Jul. 28, 2021.
Thammasorn T. et al., Probiotic bacteria (*Lactobacillus plantarum*) expressing specific double-stranded RNA and its potential for controlling shrimp viral and bacterial diseases. Aquaculture International, Apr. 6, 2017, vol. 25, No. 5, pp. 1679-1692.
Taga M.E. et al., The LuxS-dependent autoinducer Al-2 controls the expression of an ABC transporter that functions in Al-2 uptake in *Salmonella typhimurium*. Molecular Microbiology , Nov. 2001, vol. 42, No. 3, pp. 777-793.
Defoirdt T., Virulence mechanisms of bacterial aquaculture pathogens and antivirulence therapy for aquaculture. Reviews in Aquaculture, May 14, 2013, vol. 6, No. 2, pp. 100-114section "Quorum sensing-bacterial cell-to-cell communication".
Sully E.K. and Geller B.L., Antisense antimicrobial therapeutics. Current Opinion in Microbiology, Jun. 29, 2016, vol. 33, pp. 47-55.
The Search Report from Intellectual Property Office of Singapore in Application No. 11202001143Y dated Jul. 28, 2021.
EP Search Report in European Patent Office in Application No. 18844522.5 dated Jul. 27, 2021.
Sun et al., "DNA adenine methylase is involved in the pathogenesis of Edwardsiella tarda", Veterinary microbiology, Feb. 24, 2010, vol. 141, No. 1-2, 6 pp. 149-154. Full document, especially abstract and p. 3, col. 1.
Mei et al., "AidH, an alpha/beta-hydrolase fold family member from an *Ochrobactrum* sp. strain, is a novel N-acylhomoserine lactonase", Applied and environmental microbiology, Aug. 2010, vol. 76, No. 15, 10 pp. 4933-4942. Full document, especially p. 4936, col. 2; p. 4938, col. 2 to p. 4939, col. 2.
Genbank, Accession No. EF421460 "Vibrio haNeyi 3-dehydroquinate synthase (dqs), DamX-related protein, and DNA adenine methylase (dam) genes, complete eds.", Mar. 7, 2007 [on!ine]. [Retrieved on Dec. 4, 2018]. Retrieved from the internet <URL: https://www.ncbi.nlm.nih.gov/nuccore/EF421460 > full sequence, 3 pages.
Genbank, Accession No. GQ84901 O "*Ochrobactrum* sp. T63 peptidyl-tRNA hydrolase domain protein, alpha/beta hydrolase fold protein (aidH), pyruvate dehydrogenase, pantothenate kinase, and phosphoribosyl-ATP byrophosphohydrolase", Jul. 27, 2010 [online]. [Retrieved on Dec. 4, 2018]. Retrieved from the internet <URL: https://www.ncbi.nlm.nih.gov/nuccore/GQ84901 OJ, 3 pages.
Julio et al., "DNA Adenine Methylase Is Essential for Viability and Plays a Role in the Pathogenesis of Yersinia pseudotuberculosis and Vibrio cholerae", Infection and Immunity, Dec. 1, 2001 (Dec. 1, 2001), vol. 69, No. 12, 6 pp. 7610-7615. entire document.
Genbank, "EF421460: Vibrio harveyi 3-dehydroquinate synthase (dqs), DamX-related protein, and DNA adenine methylase (dam) genes, complete eds", NCBI, Accession: EF421460.1, Mar. 7, 2007 (Mar. 7, 2007), 5 pages: 1-5. Retrieved from the Internet: <https:/lwww.ncbi.nlm.nih.gov/nuccore/12650fi72fi/> on Jul. 25, 2018 (Jul. 27, 2018). entire document.
Subhadra et al., "Development of Paratransgenic Artemia as a Platform for Control of Infectious Diseases in Shrimp Mariculture", Journal of Applied Microbiology, Feb. 8, 2010 (Feb. 8, 2010), vol. 108, Iss. 3, 10 pp. 831-840. entire document.
International Search Report and Written Opinion in PCT Application No. PCT/US18/45687, filed on Aug. 7, 2018, 39 pages.
International Search Report and Written Opinion in PCT Application No. PCT/US18/25766, filed on Apr. 2, 2018, 22 pages.
International Search Report and Written Opinion in PCT Application No. PCT/US18/33976, filed on May 22, 2018, 24 pages.
Indonesia Substantive Examination Result Stage I in Application No. P00202001822 dated Mar. 8, 2022, 4 pages.
Office Action in corresponding Brazilian Patent Application Serial No. 112019024615-0, dated Jan. 12, 2023.
Olmos, et al., "Bacillus subtilis A potential probiotic bacterium to formulate functional feeds for aquaculture", J Micro & Bio Tech, 2014, 6(7), pp. 361-365.
Extended Search Report in corresponding European Patent Application Serial No. 18805259.1, dated Feb. 26, 2021.
Office Action in corresponding Chinese Patent Application Serial No. 201880059868.5, dated Jun. 13, 2023 (English machine translation attached).

* cited by examiner pAidH

SYSTEMS AND METHODS FOR THE CONTROL OF ACUTE HEPATOPANCREATIC NECROSIS DISEASE

CROSS REFERENCE TO RELATED APPLICATION

This application is a national stage application under 35 U.S.C. 371 of PCT Application No. PCT/US2018/045687 having an international filing date of Aug. 7, 2018, which designated the United States, which PCT application claimed the benefit of U.S. Application No. 62/541,824, filed Aug. 7, 2017, and PCT Application No. PCT/US18/25766, filed Apr. 2, 2018, and PCT Application No. PCT/US18/33976, filed May 22, 2018. The entire specifications and figures of the above-mentioned applications are hereby incorporated, in their entirety by reference.

SEQUENCE LISTING

The instant application contains a Sequence Listing which has been submitted electronically in ASCII format and is hereby incorporated by reference in its entirety. Said ASCII copy, created on Aug. 7, 2018, is named PCT7-AF.txt and is 12 Kbytes in size.

TECHNICAL FIELD

Generally, the inventive technology relates to novel trans-biotic strategies for controlling disease-causing agents. In particular, the inventive technology may include novel systems, methods, and compositions for treating and/or preventing Early Mortality Syndrome (EMS) associate mortality susceptible organisms, through the use of genetically engineered bacteria expressing one or more molecules that reduce virulence/fitness of pathogenic *Vibrio* sp. in the shrimp intestine.

The inventive technology may include novel systems for disrupting bacterial quorum sensing, and its associated virulence and biofilm formation, through the introduction of "quorum quenching" molecules delivered to a target host by genetically modified bacteria. In some embodiments, the inventive technology may include a novel EMS control strategy which includes the introduction of genetically engineered donor bacterial strains configured too efficiently and continuously deliver quorum quenching molecules to a target host/environment resulting in the reduction in levels of bacterial quorum sensing molecules that may regulate the pathogenic states of EMS-mediated pathogens.

The inventive technology may further include novel systems for regulating bacterial gene expression through the introduction of antisense RNA (asRNA) that may disrupt expression of targeted pathogenic genes and/or their products (RNA, proteins). In some embodiments, the inventive technology may include novel genetically engineered donor bacterial strains configured too efficiently and continuously deliver pathogen disruptive molecules and/or asRNA polynucleotides to a recipient pathogen/host to treat and/or prevent EMS-mediated disease conditions.

BACKGROUND OF THE INVENTION

The development of aquaculture has generated a significant shift in global food production away from traditional catch production methods. Driven primarily by population increases, as well as a lack of growth in traditional capture fishery production, aquaculture has expanded rapidly to become a major component in the world-wide food production eco-system. Aquaculture is now seen as playing a key role in many emerging economies, by virtue of its potential to contribute to increased food production while helping reduce pressure on fish resources. As noted by the United Nations Food and Agriculture Organization (UNFAO) in its 2016 Report on the State of the World Fisheries and Aquaculture, aquaculture is the fastest growing area of animal protein production and has significantly outpaced traditional capture fishery production. For example, the UNFAO estimates that aquaculture production now accounts for half of all seafood produced for human consumption.

The increasing global population, growing demand for seafood, and limitations on production from capture fisheries will inevitably lead the continued global expansion of aquaculture with its associated risks of disease emergence and spread. Despite the world's growing reliance on aquaculture as a primary source of food production, especially in many developing economies, traditional aquaculture systems present several technical and biological challenges that limit their overall effectiveness. One major drawback of aquaculture systems is that the aquatic animals are typically placed in high density production systems. This can result in stress from crowding and sub-optimal water quality conditions that provide for easy transmission of disease. In particular, disease outbreaks in aquaculture systems can result in massive losses among aquatic populations, resulting in large economic losses in commercial aquaculture. Indeed, such disease outbreaks have reportedly cost the aquaculture industry tens of billions dollars in the last 20 years.

In the case of shrimp aquaculture, the problem of disease is especially severe. According to the UNFAO, although global aquaculture shrimp production has increased, major producing countries, particularly in Asia, have experienced a significant decline in output as a result of widespread shrimp disease. There are several reasons for this. First, unlike vertebrates, shrimp lack many of the key components of adaptive and innate immune response mechanisms preventing many traditional methods of inducing or enhancing natural disease resistance. Second, most of the major pathogenic viruses cause very low level persistent infections that can occur at moderate to very high prevalence in apparently healthy shrimp populations. The majority of shrimp pathogens are transmitted vertically and disease is the result of a massive viral amplification that follows exposure to various forms of environmental or physiological stress. Stressors can include handling, spawning, poor water quality, or abrupt changes in temperature or salinity. Shrimp viruses can also be transmitted horizontally. Once viral loads are high and disease is manifest, horizontal transmission of infection is accompanied by transmission of disease. Third, shrimp commonly are infected simultaneously or sequentially with multiple viruses, or even different strains of the same virus. This fact poses significant challenges for diagnosis, detection, and pathogen exclusion in aquaculture systems.

Acute Hepatopancreatic Necrosis Disease (AHND), also known as Early Mortality Syndrome (EMS) has emerged as one of the most devastating diseases in shrimp aquaculture. EMS has severely affected the aquaculture industries in several countries in the eastern and western hemispheres such as China, Vietnam, Malaysia, Thailand, and Mexico. As shown in FIG. 1, The Global Aquaculture Alliance has estimated that losses to the Asian shrimp culture sector due to EMS amount to USD 1 billion. In some instances, outbreaks of EMS have result in a staggering 80% loss of shrimp aquaculture populations. EMS is caused by *Vibrio* bacterial species, for example, *V. harveyi* and *V. parahaemolyticus*, which can be transmitted orally. These *Vibrio* species colonize the shrimp gastrointestinal tract and produce a toxin that causes tissue destruction and dysfunction of the shrimp digestive organ known as the hepatopancreas. EMS typically affects post-larvae shrimp within 20-30 days after stocking and frequently causes up to 100% mortality.

Currently, there are no available methods to treat EMS. Traditional strategies to prevent or treat outbreaks of EMS may actually have the effect of aggravating the disease propagation. For example, attempts at total disinfection of pond bottom and water to kill possible vectors of EMS may actually contribute to the epidemic spread of the EMS disease rather than control it by removing potentially competitive microbial populations. In addition, the use of disinfectants not only destroys microbially mature systems; these methods have already been shown to be ineffective in treating diseases caused by luminescent Vibrios (i.e., *V. harveyi* and other bacteria which are closely related to the bacteria causing EMS).

Other attempts have been made to create and isolate EMS pathogen-free populations for aquaculture. However, such efforts are slow and require significant expertise and diagnostic capabilities that are prohibitively expensive, not to mention largely ineffective. Large-scale applications of antibiotics have been applied to shrimp aquaculture, in particular during the production cycle, both in the larval and growth phases. Sensitivity tests have shown EMS causing bacteria have already developed resistance to the full range of antibiotics. As such, the use of antibiotics to control EMS has been associated with environmental and human health problems, including bacterial resistance, and persistence of the disease in the aquatic environment. The accumulation of antibiotic residues in the edible tissues of shrimp may also alter human intestinal flora and cause food poisoning or allergy problems. Other methods such as the application of immunostimulants or bacteriophage treatments to target other types of shrimp aquaculture pathogens have been tried in other instances with limited commercial and practical success and would be equally ineffective against EMS causing pathogens.

One proposed solution is the utilization of engineered RNA-based molecules. For example, the use of asRNA as highly specific antibacterial drugs has been broadly explored in recent decades. Antisense RNA (asRNA) technology employs production of an RNA molecule which is complementary and hybridizes to a targeted mRNA. As a result of the hybridization of the asRNA to the targeted mRNA, the mRNA is unable to serve as template for protein translation, therefore asRNA-mRNA interaction leads to elimination or reduction of levels of the mRNA encoded protein in the bacteria. In addition, the targeted mRNA may be hydrolyzed by RNases, resulting in post-transcriptional gene silencing. One of the greater obstacles for practical application of asRNA as antibacterial treatments, however, has been the mode of production and delivery of asRNA to infection sites. The challenge has been how to continuously produce and deliver sufficient quantities of asRNA over a long period of time to silence the targeted essential gene in the pathogen at very low or no cost.

The foregoing problems regarding the biocontrol of EMS pathogens in shrimp aquaculture populations may represent a long-felt need for an effective—and economical—solution to the same.

As will be discussed in more detail below, the current inventive technology overcomes the limitations of traditional EMS pathogen control systems, while meeting the objectives of a truly effective EMS vector biocontrol strategy.

BRIEF SUMMARY OF THE INVENTION

Generally, the inventive technology relates to novel strategies for disease control in animal systems. Specifically, the invention may comprise novel techniques, systems, and methods for the biocontrol of pathogens in aquatic systems. In certain embodiments, this may be accomplished through the introduction of genetically modified bacteria to hosts that express specific molecules that may downregulate key targeted pathogen genes and/or disrupt molecular pathways that lead to, for example enhanced pathogenicity and/or biofilm formation. The inventive technology may further comprise novel systems for the biocontrol of virulence-specific pathogens in aquaculture systems. This system may also use a novel cross-kingdom mechanism to introduce engineered microorganisms that may inactivate specific genes in the pathogen using asRNA that may disrupt expression of one or more genes of interest and/or specific molecules that may inhibit quorum-sensing and or biofilm formation in bacterial pathogen populations.

One aspect of the inventive technology may include systems, methods, and techniques for the biocontrol of bacterial diseases in shrimp aquaculture by introducing engineered microorganisms that may modulate the concentration and/or bioavailability of quorum-sensing molecules as a novel method to EMS pathogenicity. One aspect the invention includes systems, methods, and compositions for treating and/or preventing EMS in shrimp, through the use of genetically engineered enteric bacteria expressing one or more molecules that reduce virulence/fitness of pathogenic *Vibrio* sp. in the shrimp intestine. In one preferred aspect, the invention involves the generation of genetically engineered enteric shrimp bacteria configured to reduce quorum sensor or autoinducer molecules in shrimp intestines to treat and/or prevent EMS-associated shrimp mortality.

Another aspect of the invention may include systems, methods and compositions to reduce autoinducer 2 (AI-2) levels in the environment and thereby disrupt pathogenic quorum-sensing as well as the production of biofilms. In one preferred aspect, the invention may include the reduction in levels of bacterial quorum sensing (QS) molecules that regulate the pathogenic states of *Vibrio*, which in turn may be part of an effective EMS control strategy. For example, the autoinducer 2 (AI-2 class, furanosyl borate diester) of QS molecules may up-regulate EMS pathogenesis in *Vibrio*. Additional aspects may include the control of *Vibrio* QS regulated gene expression through the control of two additional classes of QS molecules including, the acylated homoserine lactones (AHL) and the CAI-1 class of QS molecules. As such, in one preferred aspect, the invention includes the creation of genetically modified bacteria that may be configured to overexpress the lsr operon from *E. coli* in enteric bacteria able to colonize shrimp intestines to reduce exogenous AI-2 levels produced by pathogenic or other QS capable bacteria. In this aspect, the reduction in AI-2 levels of QS molecules may reduce and/or prevent EMS pathogenesis in *Vibrio*.

Another aspect of the invention may include systems, methods and compositions to reduce AI-1 autoinducer molecules levels in the environment and thereby disrupt pathogenic quorum-sensing as well as the production of biofilms. In one preferred aspect, the invention includes the creation of genetically modified enteric bacteria that may be configured to overexpress to express homoserine lactonases (AHL lactonase) to inactivate the AHL class (Hal-1) of QS molecules that can also activate the expression of pathogenicity genes in *Vibrio*.

The present invention also relates to the utilization of genetically modified donor bacteria that may be configured to produce certain asRNA polynucleotides that may target specific bacterial genes and/or their products (RNA, proteins) in eukaryotic systems. These asRNA polynucleotides may inhibit or reduce the expression of certain genes and/or cause the impairment or degradation of gene products in a disease-causing agent. The invention may comprise novel techniques, systems, and methods for controlling pathogenic bacteria, for example EMS-causing *Vibrio* species.

One aim of the current inventive technology may include novel systems, methods and compositions for the transbiotic regulation of bacterial gene expression in a recipient pathogenic bacterium by asRNA. One embodiment of the invention may include the effective expression of high levels of asRNA in a donor bacterium species harbored in the host. In certain embodiments, this donor bacterium may be a symbiotic, endosymbiotic, and/or probiotic enteric or other bacterium species genetically engineered to express one or more heterologous asRNA polynucleotides.

Another aim of the current invention may include the production of heterologous asRNA in a donor bacterium that may further be delivered to an acceptor bacterium, more specifically an EMS-causing pathogenic bacterium. These heterologous asRNA polynucleotides may target specific genes and their RNA and/or protein products that may be unique and/or restricted to a target bacterial pathogen. Such heterologous asRNA polynucleotides can be fully complementary, or contain mismatches in relation to their targets; both aspects can induce degradation of their targets or impair their translation, making them unavailable for accomplishing their function.

Yet another aim of the current invention may include the suppression of targeted gene expression in the recipient bacteria, resulting in the suppression of bacterial populations and/or pathogenic activity of the bacteria in a host eukaryotic organism.

Another aim of the present invention may include the generation of one or more plasmids and/or bacterial artificial chromosomes (BACs) that may encode one or more heterologous asRNA polynucleotides. An additional aim may include integration of specific genetic elements encoding one or more asRNA into the genome of a pathogen. An additional aim of the invention may be to produce genetic constructs that may produce non-coding RNA molecules, such as the aforementioned heterologous asRNA polynucleotides, by a constitutive, inducible, heterologous, or homologous gene promoter/terminator pair in the donor bacterium strain. Yet another aim of the present invention may include the co-expression of certain proteins or other factors that may protect the non-coding RNA molecule from degradation.

An additional aim of the present invention may include the development of genetically modified auxotrophic bacterial strains that may produce heterologous asRNA polynucleotides that may further be more efficiently delivered to a target pathogen via nanotubes.

Another aim of the present invention may include novel biocontrol strategies for various aquatic organisms, such as shrimp. Another aim of the present invention may include, in a preferred embodiment, novel biocontrol strategies for aquaculture populations. In this embodiment, the inventive technology includes various cross-kingdom mechanisms for the knockdown of essential pathogen genes in aquatic animals grown in aquaculture systems. This may be accomplished through the introduction of engineered microorganisms into aquaculture animal populations that express specific heterologous asRNA polynucleotides that may downregulate and/or suppress selected pathogen essential genes.

In one preferred aspect, the invention may include the generation of genetically modified bacteria that may be configured to express one or more asRNA targeting DNA methylation in Vibrios. In one preferred embodiment, the invention may include the generation of genetically modified bacteria that may be configured to express one or more asRNA targeting the *Vibrio* DNA adenine methylase dam gene In this aspect, the asRNA is configured to significantly suppress dam expression in *Vibrio harveyi* during co-cultivation or in host-pathogen system. In this preferred aspect, the invention may further include delivery of pathogen-specific asRNA-dam to an infected and/or susceptible host by enteric bacteria configured to reduce dam expression in *Vibrio parahaemolyticus* in shrimp intestines and therefore prevent EMS-associated mortality.

Another aim of the invention may include methods of targeting multiple essential bacterial-specific gene targets for silencing as well as inhibit QS-mediated pathogenesis states, such that it may be possible to selectively diminish EMS causing *Vibrio* pathogens in shrimp populations grown in aquaculture environments. In this embodiment, the invention may include the generation of feeds containing genetically modified bacteria configured to express select quorum quenching molecules that may inhibit quorum sensing in *Vibrio* populations and thereby control EMS. In other aspects, the invention may include the generation of feeds containing genetically modified bacteria configured to express select asRNAs that may target and suppress one or more *Vibrio* pathogen genes. In one embodiment, such a treated feed may be introduced to a pathogen-susceptible or pathogen-affected population.

In some aspect of the invention, such interfering RNA molecules, such as asRNA, and/or quorum quenching molecules expressed by genetically modified bacteria may act as a vaccine to immunize shrimp. As such, one aim of the invention may include the use of genetically modified bacteria to colonize and express molecules that provide individual or herd immunity in aquatic animals directed to EMS, such as shrimp populations grown in aquaculture systems.

Another aim of the invention may be the generation of genetically modified symbiotic and/or probiotic bacterial strains that may express one or more quorum quenching molecules and/or inhibitory RNA molecules directed to EMS causing Vibrios. In a certain embodiments, shrimp bacteria enteric or endosymbiotic such as *Enterobacter* sp., may be genetically modified to express one or more quorum quenching molecules and/or inhibitory RNA molecules directed to EMS causing Vibrios.

Yet further embodiments may include genetically modified microorganisms that may include genetic constructs that may further co-express certain proteins having processing enzymatic activity. Such co-expressed proteins may include enzymes that may inhibit and/or enhance post-translational processing and/or modification of inhibitory RNA molecules. Other similar embodiments may include the introduction of microorganisms into a target organism that may express, or even over-express, various genes that may enhance mobilization of inhibitory RNA molecules and/or genes that may activate secondary downstream host genes that may target pathogenic pathways.

Finally, the present inventors describe embodiments of the invention including protocol for shrimp feeding by an RNaseIII deficient genetically modified bacteria that express inhibitory RNA molecules directed to EMS causing Vibrios.

Additional aspects of the invention will be evident from the detailed figures and descriptions below.

BRIEF DESCRIPTION OF THE FIGURES

The accompanying figures, which are incorporated into and form a part of the specification, illustrate one or more embodiments of the present invention and, together with the description, serve to explain the principles of the invention. The drawings are only for the purpose of illustrating one or more preferred embodiments of the invention and are not to be construed as limiting the invention.

MODE(S) FOR CARRYING OUT THE INVENTION(S)

Figure 1:
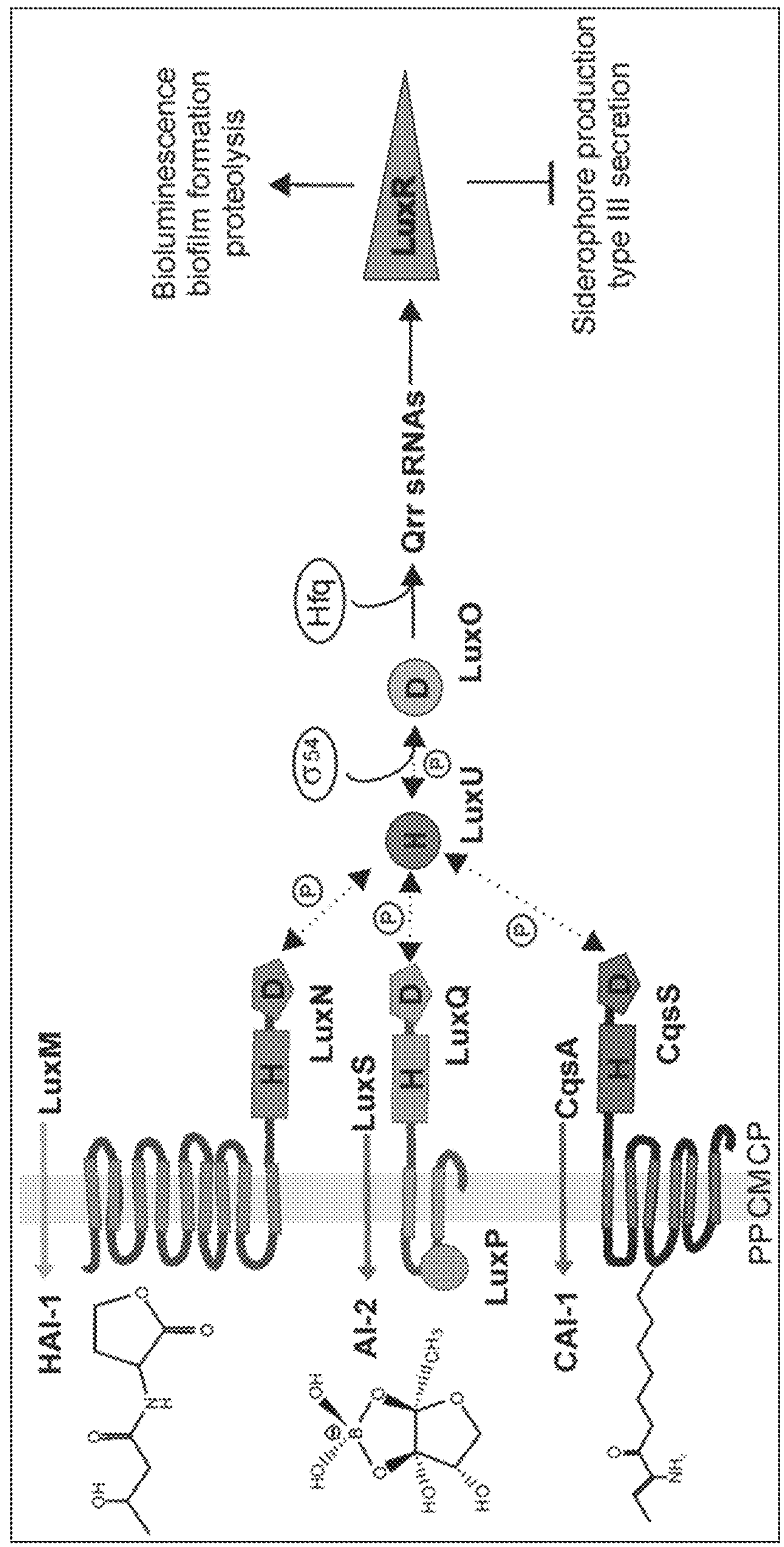
FIG. 1: Exemplary bacterial quorum-sensing pathways.

The present invention includes a variety of aspects, which may be combined in different ways to generally describe the novel systems, methods and compositions related to the control and treatment of Acute Hepatopancreatic Necrosis Disease A/K/A Early Mortality Syndrome (EMS). The following descriptions are provided to list elements and describe some of the embodiments of the present invention. These elements are listed with initial embodiments, however it should be understood that they may be combined in any manner and in any number to create additional embodiments. The variously described examples and preferred embodiments should not be construed to limit the present invention to only the explicitly described systems, techniques, and applications. Further, this description should be understood to support and encompass descriptions and claims of all the various embodiments, systems, techniques, methods, devices, and applications with any number of the disclosed elements, with each element alone, and also with any and all various permutations and combinations of all elements in this or any subsequent application.

The invention may include systems, methods and compositions for the inhibition of quorum-sensing (QS), QS-mediated pathogenesis, and the formation of biofilms in target pathogenic bacteria. (See FIG. 1). Generally, QS describes a system of stimuli and response correlated to bacterial population density. Quorum sensing may allow bacteria to constantly produce and excrete low-molecular-weight signaling molecules, generally referred to as autoinducers (AIs), into the surrounding environment. As the number of bacteria increase, so does the concentration of AIs. At a defined threshold of AI concentration, the bacterial population may express a synchronized, AI-specific response—usually a phenotype, such as virulence, light production or biofilm formation, which is more effective when deployed by a group of cells rather than a single bacterium. Such quorum sensing responses can greatly enhance a bacterial pathogen's virulence gene expression, as well as make it more difficult to arrest microbial growth through antibiotics or other chemical means, as is the case with bacterial biofilms.

In one embodiment, the invention may include an isolated expression vector, such as a plasmid configured to be expressed in genetically modified bacteria that may further express a one or more heterologous polypeptides that actively transport AIs from the surrounding environment back into the genetically modified bacteria. In a preferred embodiment, the invention may include and one or more isolated expression vectors, such as a plasmid configured to be expressed in bacteria that may further express a heterologous lsr operon, preferably from the exemplary organism *E. coli* and/or *Salmonella typhimurium*. As detailed above, the lsr operon encodes an ATP-binding cassette transporter (ABC transporter) and associated chaperones that actively pump AI-2 into bacterial cells. By doing so, AI-2 concentrations in the surrounding environment are reduced, in some cases to concentrations approaching zero, thereby preventing QS-mediated activation of pathogenic states in many pathogenic bacteria, such as *Vibrio*.

The invention further includes novel systems, methods and compositions to reduce AI-2 levels in an aquaculture of other aquatic environments and thus reduce and/or treat EMS in shrimp. In one specific embodiment, this novel system may include the overexpression of a heterologous lsr operon in enteric bacteria in the intestines of shrimp. Exemplary enteric bacteria may include *Salmonella typhimurium*, as well as *Enterobacter* sp., such as Ag1. In one embodiment, through overexpression of the lsr operon, AI-2 may be actively transported back into a bacterial cell such that AI-2 concentrations in the target environment may be reduced sufficiently to prevent QS-mediated activation of pathogenic states.

In another embodiment, enteric bacteria such as Ag1, may be genetically modified to express and/or overexpress a heterologous lsr operon from the bacterial chromosome. These genetically modified bacteria may be introduced to a shrimp or other aquaculture or aquatic organism, for example through a bacteria-infused feed or through direct bacterial delivery to. for example a shrimp population in a pond or other aquaculture environment. Once permanently and/or transiently colonized in the shrimp gut, the genetically modified enteric bacteria may express and/or overexpress a heterologous lsr operon which in turn will produce the aforementioned ABC transporter and associated chaperon proteins that may actively transport AI-2 back into a bacterial cell such that concentrations in media may be significantly reduced preventing QS-mediated activation of pathogenic states in pathogenic bacteria.

The invention further includes novel systems, methods and compositions to reduce AI-2 levels in an aquaculture of other aquatic environments and thus reduce and/or treat EMS in shrimp. In one specific embodiment, this novel system may include the overexpression of a heterologous lsr operon in genetically modified enteric bacteria that may be introduced to the intestines of shrimp, for example through a bacteria-infused shrimp feed or through direct bacterial delivery to. for example a shrimp population in a pond or other aquaculture environment. As noted above, non-limiting example of enteric bacteria may include *Salmonella typhimurium*, as well as *Enterobacter* sp., such as Ag1, or other probiotic bacteria that enhance shrimp growth. The heterologous lsr operon encodes an ATP-binding cassette transporter (ABC transporter) and associated chaperonins that actively transport AI-2 into a genetically modified bacterial cell such that concentrations in media may be significantly reduced preventing QS-mediated activation of pathogenic states in EMS causing *Vibrio* that may be configured to respond to autoinducer molecules, in particular AI-2. More specifically, the extracellular reservoirs of the QS molecule AI-2 may be reduced and/or eliminated preventing both QS phenotypes, such as biofilms, from forming, as well as the QS-mediated activation and expression of EMS pathogenicity genes in *Vibrio* and other pathogen species.

In one embodiment, one or more genetically modified strains of shrimp symbiotic, endosymbiotic, and/or probiotic bacteria may contain one or more genetic constructs that may result in the overexpression of a heterologous lsr operon. In this embodiment, the genetically modified enteric bacteria may be introduced to a target shrimp or aquaculture shrimp population and become a part of the host's natural microbiome. The overexpression of the lsr operon may cause in increased number of ABC transporter and associated chaperonins that actively transport AI-2 generated by EMS pathogens, such as the various species of *Vibrio* identified herein, into the genetically modified enteric cell and thus inhibit QS, as well as biofilm formation in such *Vibrio* pathogen species.

In a preferred embodiment, genetically modified symbiotic, endosymbiotic, and/or probiotic bacteria that overexpress a heterologous lsr operon may colonize in the gut or other part of the shrimp. In this embodiment, once colonized in the host, vertical transmission of the genetically modified bacteria may be passed to the host's progeny, thus naturally replicating the pathogenic QS and biofilm suppression to subsequent generations. Additionally, the genetically modified bacteria may also be horizontally transmitted to host population at large through the distribution of the modified bacteria into the environment by shedding. Such a feature may allow for the one-time and/or periodic administration of the modified bacteria to the host and/or host's environment generating a significant commercial, technical, and cost advantage.

In another embodiment, the colonized bacteria may overexpress an lsr operon, having become a part of the host's natural microbiome, may continuously express the ABC transporter and associated chaperonins that actively transport AI-2 generated by EMS pathogens back into the colonized genetically modified bacteria, such as *Vibrio* via the intestine or other areas from the earliest larval stages to the adult stage preventing QS-mediated EMS pathogenesis throughout the host's lifecycle. As such, such genetically modified bacteria may acts as a molecular sink for AI-2 molecules. In addition, as the enteric bacteria vector may be an already naturally occurring part of the host's microbiome, its presence may not pose any risk to the organism, environment, or end-consumers.

The inventive technology may further comprise methods and techniques to control the levels and timing of the expression of the heterologous lsr operon in the target host. In one preferred embodiment, the expression of the heterologous lsr operon may be under the control of an inducible promoter or other novel gene switch. The gene switch may be controlled by a switch molecule, which may be a water-soluble and food-grade molecule that can be added to a host organism's environment or food supply. The presence of this switch molecule may activate the expression and/or over-expression of the heterologous lsr operon. It absence may prevent, or decrease expression of the heterologous lsr operon.

This embodiment may be demonstrated in genetic constructs that may include other transcription regulation elements such as promoters, terminators, co-activators and co-repressors, as well as other control elements that may regulate the expression and/or overexpression of the heterologous lsr operon. Such systems may allow for control of the timing and amount of the lsr operon proteins expressed within the system. Additional embodiments may include genetic constructs that may be induced through additional outside and/or environmental factors, such as the presence of a specific protein or compound, such as stress related proteins generated in response to a pathogen or even proteins and other precursor compounds generated by pathogens and the like.

The invention may include systems, methods, and compositions for the introduction of genetically modified bacteria, preferably enteric bacteria expressing a heterologous lsr operon to an EMS susceptible organisms and/or populations, preferably aquatic organisms grown in aquaculture environments. In this embodiment, the colonized bacteria may overexpress the lsr operon, and having become a part of the host's natural microbiome, and may continuously express the ABC transporter and associated chaperonins that actively transport AI-2 generated by EMS pathogens, such as *Vibrio* via the intestine or other areas and thus providing prophylactic protection to the population against EMS, preferably *Vibrio*-mediated EMS.

In a preferred embodiment, an exemplary lsr operon may be identified as SEQ ID NO. 2, or a sequence having 70% to 99% homology thereof. In this embodiment, the lsr operon may be part of an expression cassette, and may further be operably linked to a promoter.

The invention may include systems, methods and compositions for the inhibition of pathogenicity and the formation of biofilms in target pathogenic bacteria through the inhibition of bacterial QS. In a preferred embodiment, the invention may include systems, methods, and compositions for the inhibition/inactivation of the autoinducer-1 molecules (AH-1). In this preferred embodiment, endosymbiotic, symbiotic and/or probiotic bacteria may be genetically modified to express and/or overexpress one or more heterologous acylated homoserine lactonases (AHL lactonase) that inactivate the AI-1 molecules, specifically AHL class (Hal-1) QS molecules. The expression of such heterologous AHL lactonase may further inhibit the expression of pathogenicity genes in one or more EMS-causing species of *Vibrio*. In some embodiments, the reduction of AHLs may reduce *Vibrio* bacterial reservoirs in aquaculture environments, or other natural environments, such as ponds and lakes that may act as stage gates for shrimp infections.

In one embodiment, the invention may include an isolated expression vector, such as a plasmid configured to be expressed in bacteria that may further express one or more heterologous polypeptides that inhibit QS and/or biofilm production, as well as the expression of pathogenicity genes, preferably through the inhibition/inactivation of the AHL class (Hal-1) of QS molecules. In a preferred embodiment, the invention may include and one or more isolated expression vectors, such as a plasmid configured to be expressed in bacteria that may further express a heterologous AHL lactonase, preferably the aidH gene from Ochrobactrum.

As noted above, bacteria expressing AHL lactonase may reduce virulence/fitness of pathogenic *Vibrio* sp. in shrimp. As such, the invention further includes novel systems, methods and compositions to inhibit QS, biofilm formation and pathogenicity/fitness of *Vibrio* species in an aquaculture of other aquatic environments and thus reduce and/or treat EMS in shrimp. In one specific embodiment, this novel system may include the overexpression of a heterologous AHL lactonase, such as aidH in enteric bacteria in the intestines of shrimp. Exemplary enteric bacteria may include *Salmonella typhimurium*, as well as *Enterobacter* sp. such as Ag1. The aidH gene encodes a hydrolytic protein that interferes with QS-mediated functions through the inactivation of AHL class (Hal-1) of QS molecules thereby preventing QS-mediated activation of pathogenic states in bacteria, preferably EMS-causing *Vibrio* species.

In another embodiment, enteric bacteria such as Ag1, may be genetically modified to express and/or overexpress a heterologous aidH gene. This genetically modified bacteria may be introduced to a shrimp or other aquaculture or aquatic organisms, for example through a bacteria-infused feed. Once permanently and/or transiently colonized in the shrimp gut, the genetically modified enteric bacteria may express and/or overexpress a heterologous aidH gene which in turn will produce the aforementioned inactivation of AHL class (Hal-1) of QS molecules and thereby inhibit QS-mediated activation of pathogenic states in bacteria.

The invention further includes novel systems, methods and compositions to reduce active AI-1 activity in an aquaculture of other aquatic environments and thus reduce and/or treat EMS in shrimp. In one specific embodiment, this novel system may include the overexpression of a heterologous aidH gene in genetically modified enteric bacteria that may be introduced to the intestines of shrimp, for example through a bacterial-infused shrimp feed. As noted above, non-limiting examples of enteric bacteria may include *Salmonella typhimurium*, as well as *Enterobacter* sp., such as Ag1. The heterologous aidH gene encodes an polypeptide that inactivates AI-1s in the environment which may preventing QS-mediated activation of pathogenic states in EMS causing *Vibrio* that may be configured to respond to autoinducer molecules, in particular AI-1. More specifically, the extracellular reservoirs of the QS molecule AI-1 may be reduced and/or inactivated preventing both QS phenotypes, such as biofilms, from forming, as well as the QS-mediated activation and expression of EMS pathogenicity genes in *Vibrio* and other pathogen species.

In one embodiment, one or more genetically modified strains of shrimp symbiotic, endosymbiotic, and/or probiotic bacteria may contain one or more genetic constructs that may result in the overexpression of a heterologous aidH gene. In this embodiment, the genetically modified enteric bacteria may be introduced to a target shrimp or aquaculture shrimp population and become a part of the host's natural microbiome. The overexpression of the aidH gene may cause inactivation of AI-1 class QS-mediators generated by EMS pathogens, such as the various species of *Vibrio* identified herein, thus inhibit QS, as well as biofilm formation in such *Vibrio* pathogen species.

In a preferred embodiment, genetically modified symbiotic, endosymbiotic, and/or probiotic bacteria that overexpress a heterologous aidH gene may colonize in the gut or other part of the shrimp. In this embodiment, once colonized in the host, vertical transmission of the genetically modified bacteria may be passed to the host's progeny, thus naturally replicating the pathogenic QS and biofilm suppression to subsequent generations. Additionally, the genetically modified bacteria may also be horizontally transmitted to host population at large through the distribution of the modified bacteria into the environment as waste. Such a feature may allow for the one-time and/or periodic administration of the modified bacteria to the host and/or host's environment generating a significant commercial, technical, and cost advantage.

In another embodiment, the colonized bacteria may overexpress a heterologous aidH gene, having become a part of the host's natural microbiome, and may continuously inhibit AI-1 generated by EMS pathogens, such as *Vibrio* via the intestine or other areas from the earliest larval stages to the adult stage preventing QS-mediated EMS pathogenesis throughout the host's lifecycle. In addition, as the enteric bacteria vector may be an already naturally occurring part of the host's microbiome, its presence may not pose any risk to the organism, environment, or end-consumers.

The inventive technology may further comprise methods and techniques to control the levels and timing of the expression of the heterologous aidH gene in the target host. In one preferred embodiment, the expression of the heterologous aidH gene may be under the control of an inducible promoter or other novel gene switch. The gene switch may be controlled by a switch molecule, which may be a water-soluble and food-grade molecule that can be added to a host organism's environment or food supply. The presence of this switch molecule may activate the expression and/or overexpression of the heterologous aidH gene. It absence may prevent, or decrease expression of the heterologous aidH gene.

This embodiment may be demonstrated in genetic constructs that may include other transcription regulation elements such as promoters, terminators, co-activators and co-repressors, as well as other control elements that may regulate the expression and/or overexpression of a heterologous aidH gene. Such systems may allow for control of the timing and amount of the aidH gene proteins expressed within the system. Additional embodiments may include genetic constructs that may be induced through additional outside and/or environmental factors, such as the presence of a specific protein or compound, such as stress related proteins generated in response to a pathogen or even proteins and other precursor compounds generated by pathogens and the like.

The invention may include systems, methods, and compositions for the introduction of genetically modified bacteria, preferably enteric bacteria expressing a heterologous aidH gene to an EMS susceptible organisms and/or population, preferably shrimp grown in aquaculture environments. In this embodiment, the colonized bacteria may overexpress the aidH gene, having become a part of the host's natural microbiome, and may continuously inhibit AI-1 generated by EMS pathogens, such as *Vibrio* via the intestine or other areas and thus providing prophylactic protection to the population against EMS, in particular *Vibrio*-mediated EMS.

In a preferred embodiment, an exemplary heterologous AHL lactonase may include the aidH gene from Ochrobactrum identified as SEQ ID NO. 1, or a sequence having 70% to 99% homology thereof. In this embodiment, heterologous aidH may be part of an expression cassette, and may further be operably linked to a promoter.

The inventive technology may comprise systems and methods to control the virulence of specific bacterial or other pathogens by selective inactivation of pathogenic, essential or other target genes. This targeted gene inactivation may be accomplished by the expression and delivery of heterologous asRNA molecules from a donor bacterium to a target host pathogen. In one preferred embodiment, one or more donor bacterial species or strains may be genetically engineered to express heterologous asRNA molecules that may act to regulate and/or inhibit gene expression in target disease-causing agents, preferably EMS disease causing agents.

In certain embodiments, asRNA may include a non-coding single-stranded RNA molecule that may exhibit a complementary relationship to a specific messenger RNA (mRNA) strand transcribed from a target gene. Additional embodiments may include asRNA having one or more mismatches in relation to their target mRNA. Regardless of the homology between the mRNA and asRNA, in this embodiment, the asRNA may physically pair with, and bond to, the complementary mRNA. This complementary binding may inhibit translation of a complementary mRNA by base pairing the RNA molecules and thereby physically obstructing, or sterically hindering the translation machinery.

It should be noted that when referring to asRNA being complementary, it means that the polynucleotide for use in antisense suppression may correspond to all or part of the complement of the sequence encoding the target polypeptide, all or part of the complement of the 5' and/or 3' untranslated region of the target polypeptide transcript, or all or part of the complement of both the coding sequence and the untranslated regions of a transcript encoding the target polypeptide. A complementary nucleic acid molecule is that which is complementary to an mRNA transcript of all or part of a target nucleic acid molecule. In addition, the antisense polynucleotide may be fully complementary (i.e., 100% identical to the complement of the target sequence) or partially complementary (i.e., less than 100% identical to the complement of the target sequence) to the target sequence.

Antisense suppression may be used to inhibit the expression of multiple proteins in the same cell. Furthermore, portions of the antisense nucleotides may be used to disrupt the expression of the target nucleic acid molecule. Generally, antisense sequences of at least 10 nucleotides, 20 nucleotides, 50 nucleotides, 100 nucleotides, 200 nucleotides, 300, 500, 550, 500, 550, or greater, and any amount in-between, may be used. The sequence may be complementary to any sequence of the messenger RNA, that is, it may be proximal to the 5'-terminus or capping site, downstream from the capping site, between the capping site and the initiation codon and may cover all or only a portion of the non-coding region, may bridge the non-coding and coding region, be complementary to all or part of the coding region, complementary to the 3'-terminus of the coding region, or complementary to the 3'-untranslated region of the mRNA.

The antisense sequence may be complementary to a unique sequence or a repeated sequence, so as to enhance the probability of binding. Thus, the antisense sequence may be involved with the binding of a unique sequence, a single unit of a repetitive sequence or of a plurality of units of a repetitive sequence. Methods of preparing antisense nucleic acid molecules are generally known in the art.

As such, in certain embodiments, the present invention may include systems, methods and compositions to inhibit the expression of a nucleic acid molecule of a disease-causing agent, and more preferably an EMS-causing agent. When referring to inhibiting expression of a target gene, it is meant that expression of the nucleic acid molecule is inhibited, disrupted, or otherwise interfered with such that the target host is protected from a disease. Inhibiting expression of a target gene may also generally refer to translation of the nucleic acid molecule being inhibited, disrupted, or otherwise interfered with such that the eukaryotic recipient, or target host is protected from a disease. Inhibiting expression of a target gene, may also mean that expression of the nucleic acid molecule, such as an asRNA polynucleotide, inhibits, disrupts, or otherwise interferes with the expression or translation of an essential gene in a pathogen such that the eukaryotic recipient, or target host exhibits lower infection rates, transmission rates, pathogen loads, or disease symptoms than that of a wild-type (WT) hosts.

As noted above, in one embodiment, the invention may include the use of asRNA that is complimentary to a nucleic acid molecule of a target gene in an EMS-causing agent. In a preferred embodiment, a donor bacterium may be genetically modified to express a heterologous asRNA. This expression may be part of an expression vector, and may be part of an expression cassette and may further be operably linked to an expression control sequence(s). This genetically modified donor bacterium may be introduced to a target host and express the targeted heterologous asRNA which may be exported from the donor bacterium and be taken-up into the target EMS-causing agent, which in this embodiment may be a pathogenic bacteria. The heterologous asRNA, being delivered to the recipient pathogenic *Vibrio* bacteria, may prevent normal expression of the protein encoded by the targeted nucleic acid molecule. This may result in the interference with the EMS-causing agent's lifecycle, ability to replicate and/or pathogenicity, thus providing an effective antibacterial delivery system. In this embodiment, the donor bacterium may be a symbiotic bacterium strain that may persist in the target host and provide continuing expression of heterologous asRNA, thus providing on-going production in the host target to counter the EMS-causing agent. In additional embodiments, the donor bacterium may be a probiotic, or probiotic-like bacteria that may persist in the target host and express and deliver heterologous asRNA to a recipient bacterial pathogen for a limited period of time. In this manner, multiple and sequential exposures of the target host to a probiotic, or probiotic-like bacteria may effectively deliver heterologous asRNA, but not persist permanently within the target host.

In another preferred embodiment, a genetically modified donor bacterium may be introduced to a target host that has not been exposed to an EMS-causing agent and may express the targeted heterologous asRNA which may be exported from the donor bacterium into the target host's cellular and/or intracellular environment. The heterologous asRNA, being delivered to the recipient host may act as a prophylactic treatment such that when the target EMS-causing agent, such as a pathogenic *Vibrio* bacteria, is introduced to the target host, heterologous asRNA prevents normal expression of the protein encoded by the targeted nucleic acid molecule and may prevent the ability of the EMS-causing agent to colonize or affect the target host. In this embodiment, the donor bacterium may be a symbiotic bacterium strain that may persist in the target host and provide continuing expression of heterologous asRNA, thus providing on-going prophylactic vaccine production in the host imparting a level of immunity to the EMS-causing agent.

Additional embodiments may include asRNA-induced gene inactivation of one, or a plurality, of target genes. For example, in one preferred embodiment, gene inactivation may be directed to one or more pathogen genes that are essential to virulence, coat proteins, metabolic activity, infection pathways and/or energy-production and the like. While provided in an exemplary model, a target gene may include one or more genes that are responsible for a bacteria's pathogenicity, or the capacity to cause a disease condition in the host.

In one embodiment, the invention may include identification of a target gene in an EMS-causing agent. In this preferred embodiment, the target gene may include an essential gene of an EMS-causing agent, meaning that the inhibition, disruption, or interference with in the expression and/or translation of one or more essential genes results in the reduction in the number of EMS-causing agents, amelioration of pathogenicity of the EMS-causing agent, interruption in the EMS-causing agent's life-cycle, ability to colonize the eukaryotic host, evade a specific or general immune response in the host, or cause a disease state.

In one embodiment, the heterologous asRNA, directed to a nucleic acid sequence in the EMS-causing agent which is to be expressed or inhibited (target nucleic acid molecule or target gene), may either express, inhibit, or compete for binding sites with any such target nucleic acid molecule which, when administered, results in protection to the eukaryotic host from the disease causing agent.

According to one aspect of the present invention there is provided a method of controlling a pathogenically infected organism, the method comprising administering to a target host organism, which in a preferred embodiment may include aquatic organisms, a nucleic acid agent comprising a nucleic acid sequence which specifically downregulates an expression of at least one essential target pathogen gene product, wherein downregulation of the expression of at least one essential target pathogen gene product in the target host rendering the target host protected from the pathogen-caused disease state.

In one preferred embodiment, such a nucleic acid agent may include an asRNA polynucleotide identified as SEQ ID NO. 4, or a homolog and/or ortholog, or other sequence having 70%-99% homology thereof. Additional embodiments may include any nucleic acid that spans a region of greater than average homology between an essential target gene of various strains of an EMS-causing pathogen. One preferred embodiment may include any nucleic acid that spans a region of greater than average homology between the essential target genes of various strains of a *Vibrio*. In the example of an EMS-causing *Vibrio* disease causing agent, this may include, as shown generally below in the region encoding the dam gene identified as SEQ ID NO. 4, among others. As noted elsewhere, dam is an essential gene in *Vibrio* sp. and is involved in regulation of gene expression. Dam is also involved in regulation of virulence pathway in many EMS-causing bacteria.

In a preferred embodiment, the invention may include one or more genetically engineered Ag1 bacteria configured to deliver one or more asRNA molecules to pathogenic bacteria in a host organism. In a preferred embodiment, the invention may include one or more genetically engineered bacteria configured to deliver one or more asRNA molecules identified as SEQ ID NO. 3, or a sequence having 70% to 99% homology thereof, directed to inhibit dam gene expression, identified as SEQ ID NO. 3, or a sequence having 70% to 99% homology thereof, in EMS-causing pathogenic bacteria in an aquatic host organism, such as shrimp or other organisms commonly raised through aquaculture.

In another preferred embodiment, the current inventive technology may extend this technology to symbiotic microorganisms that persist in the tissues, offspring and/or eggs of a host throughout their development and into the adult stage. In this manner, genetically modified microorganisms may produce and deliver asRNA molecules continuously to target pathogens such as EMS-causing *Vibrio*. This may be used to treat an EMS disease-condition in an already infected host, and/or immunize a susceptible host population.

The present invention may further include one or more vectors for inhibiting the expression of multiple pathogen genes, wherein the vector comprising one, or a plurality of heterologous asRNA polynucleotides that may correspond to one or more select pathogen genes. This embodiment may include the use of a plasmid expression system. In some embodiments, this plasmid may have one or more expression cassettes, including: at least one gene suppressing cassette containing a polynucleotide operably linked to an expression control sequence(s), wherein the polynucleotide encodes a heterologous asRNA molecule configured to reduce expression of a target pathogen gene as generally described herein.

A preferred embodiment of the present invention includes a vector for modulating multiple pathogen genes, wherein the vector comprising one or a plurality of asRNAs may correspond to one or more select host genes. This embodiment may include the use of a plasmid expression system. In some embodiments, this plasmid may have one or more expression cassettes, including: at least one gene suppressing cassette containing a polynucleotide operably linked to an expression control sequence(s), wherein the polynucleotide encodes a heterologous asRNA molecule configured to reduce expression of a target pathogen gene as generally described herein.

The present invention also includes a vector for inhibiting the expression of EMS-causing agent gene in a host, wherein the vector comprises at least one gene suppressing cassette containing a polynucleotide operably linked to an expression control sequence(s), wherein the polynucleotide encodes an asRNA molecule that reduces expression of a target pathogen gene. In one embodiment, the polynucleotide encoding the asRNA comprises the nucleotide sequence of SEQ ID NO. 3. Examples of suitable promoters for gene suppressing cassettes include, but are not limited to, Pupp, T7 promoter, bla promoter, U6 promoter, pol II promoter, Ell promoter, and CMV promoter and the like. Optionally, each of the promoter sequences of the gene promoting cassettes and the gene suppressing cassettes can be inducible and/or tissue-specific.

In further aspects, the present invention includes methods of administering a therapeutically effective amount of one or more genetically modified donor bacteria expressing a heterologous asRNA polynucleotide and/or quorum quencher molecule as generally described above. In one embodiment, this therapeutically effective amount may be the amount of bacteria, or the amount of heterologous asRNA polynucleotide and/or quorum quencher molecule expressed by a donor genetically modified bacteria that may be transported out of the donor and taken-up by a target *Vibrio* pathogen to ameliorate, reduce or eliminate a disease condition, preferably EMS, and/or said quorum quenchers may inhibit GQ-mediated pathogenicity respectively. In one preferred embodiment, as asRNA and one or more quorum quenchers may be co-expressed as generally described herein.

In another embodiment, this therapeutically effective amount may be the amount of genetically modified bacteria, or the amount of heterologous asRNA polynucleotide and/or quorum quencher molecule expressed by a donor genetically modified bacteria that may be transported out of the donor such that the host has increased resistance to infection by a later introduced EMS-causing *Vibrio* pathogen.

In another embodiment, this therapeutically effective amount may be the amount of genetically modified donor bacteria that can colonize, or become endemic within a population of target hosts through vertical and/or horizontal transfer.

In one embodiment, the present invention may include methods of administering a therapeutically effective amount of a genetically modified bacterium, configured to express heterologous asRNA polynucleotide that may target an essential target gene in *Vibrio* that is involved in DNA methylation. In a preferred embedment, this target gene may include SEQ ID NO. 4, or a sequence having 70% to 99% homology therein.

In one embodiment, the present invention may include methods for modulating DNA methylation in a *Vibrio*, or other bacterial pathogens. In this embodiment, the method may include the step of administering a therapeutically effective amount of a genetically modified bacteria, configured to express heterologous asRNA polynucleotide may target an essential target gene in *Vibrio* that is involved in DNA methylation. In a preferred embodiment, this target gene may include SEQ ID NO. 4, or a sequence having 70% to 99% homology therein.

In one embodiment, the present invention may include methods of administering a therapeutically effective amount of a genetically modified bacteria, configured to express heterologous asRNA polynucleotide, may target an essential target gene in *Vibrio* that is involved in DNA methylation and, wherein said asRNA may be identified as SEQ ID NO. 3, or a sequence having 70% to 99% homology therein.

Alternative embodiments of the present invention may include a novel in vitro and/or in vivo method to select symbiotic bacteria that may be utilized in an effective system of pathogen gene suppression. In particular, another aim of the present invention may include a novel in vitro and/or in vivo method to select symbiotic host bacteria that may be utilized in an effective system of pathogen gene suppression. These symbiotic host bacteria may be non-pathogenic in humans, and further have culturability, transformability, plasmid mobilization, and be able to able to secrete target nucleic acids, such as asRNA and the like, endemic or able to become endemic in host populations, dispersible, for example through aerosolization, able to survive in the environment and be eaten or taken up by hosts at all stages of life preferably.

In another aspect, the present invention includes methods for producing the vectors of the present invention. In yet another aspect, the present invention includes methods for producing the transformed or genetically modified microorganisms of the present invention, for example through transformation with a recombinant plasmid.

Another embodiment of the present invention may include a cell, such as a genetically modified microorganism, configured to express a heterologous nucleic acid agent, such as a asRNA, or the nucleic acid construct, such as a plasmid, of some embodiments of the invention. In one preferred embodiment, the present invention may include a genetically modified bacteria, configured to express a heterologous asRNA polynucleotide and/or a quorum quenching molecule.

Another embodiment of the present invention may include a cell comprising the isolated nucleic acid agent, such as a asRNA or a quorum quenching molecule, or the nucleic acid construct, such as a plasmid, of some embodiments of the invention wherein the cell is selected from the group consisting of a bacterial cell, an algae cell, a symbiotic bacteria, and a cell of a water surface microorganism. According to an aspect of some embodiments of the present invention, there is provided an ingestible compound comprising the cell of some embodiments of the invention.

In another preferred embodiment, a species or strain of bacteria may be modified to produce an asRNA that may be complementary to the mRNA encoding DNA adenine methylase (Dam) in *Vibrio*. These modified bacteria may include strains or species that are part of the normal flora of shrimp, and or symbiotic and/or endosymbiotic with a target host, such as shrimp or other aquatic organisms. Upon introduction, these genetically engineered bacteria maybe taken up by the shrimp and become part of the normal flora.

In this embodiment, asRNA identified as SEQ ID NO. 1, may be expressed in a donor bacterium, such as *E. coli* or and *Enterobacter* strain such as Ag1, and may suppress the expression of the dam, or other essential gene in *Vibrio* in a target host. In another embodiment, asRNA-Dam, identified as SEQ ID NO. 1, expressed in a donor bacterium, identified as SEQ ID NO. 4, may decrease EMS-causing *Vibrio* fitness and also generate a pronounced decline in biofilm formation or pathogenesis. The decrease in *Vibrio* fitness may be directly related to a reduction of Dam expression in the recipient *Vibrio* cells as indicated by the observations found in fully incorporated PCT Application No. PCT/US18/33976, that: 1) *Vibrio* DNA is 30% less methylated when co-cultivated with bacteria expressing asRNA-Dam; 2) the *Vibrio* replication origin oriC and promoter of dnaA, critical elements in the initiation of DNA replication, were 2-folds less methylated than in controls not exposed to bacteria expressing asRNA-Dam; 3) expression of *Vibrio* dam gene was also decreased 2-fold relative to controls; 4) expression of the *Vibrio* dnaA gene was decreased 3-fold relative to controls; 5) expression of *Vibrio* dam gene may be decreased 6-fold when exposed to *Enterobacter* Ag1 expressing asRNA-Dam in the model animal organism. Such results demonstrate the ability of the current invention to control disease and biofilm generation by targeted production and delivery of asRNA from a donor to a recipient bacterium in a host organism.

As noted above, the delivery of heterologous asRNA or quorum quenching molecules, may be accomplished through the introduction of genetically modified host-specific donor microorganisms, such as enteric, endophytic, symbiotic, and/or endosymbiotic bacteria. Such genetically modified host-specific microorganisms may include: 1) microorganisms that are part of the target pathogen's normal internal or external bacterial microbiome; 2) microorganisms that have been modified to be capable of colonizing a target host, tissue, cell or host environment; 3) microorganisms that that are utilized as a food or energy source by the target host; or 4) microorganisms that have been modified to colonize, or transiently persist in the target host as in the case of a probiotic or probiotic-like microorganism, a specific animal, plant, tissue, cell or host environment. As noted above, in one preferred embodiment, the heterologous asRNA donor bacterium may include *E. coli*, as well as bacterium from the genus *Enterobacter*, such as Ag1 as herein described.

In one preferred embodiment, donor bacteria may be transformed with artificially created genetic constructs, such as plasmids that may generate heterologous asRNA polynucleotides and/or quorum quenching molecules. Such plasmids may be constructed to be transferrable to other bacteria through conjugation and other means which may allow for widespread distribution of the construct, in some instances. In certain embodiments, asRNA molecules and/or quorum quenching molecules can be encoded on plasmids and/or BACs under the control of a constitutive, inducible, heterologous, or homologous gene promoter/terminator pair in the donor bacteria delivering the heterologous asRNA polynucleotides and/or quorum quenching molecules. In an additional embodiment, genetic constructs for the generation of heterologous asRNA polynucleotides and/or quorum quenching molecules may be integrated into the bacterial genome of the delivery or host bacteria.

In another preferred embodiment, one or more heterologous asRNA polynucleotides and/or quorum quenching molecules may be delivered to a target animal host/population through genetically modified donor bacteria that may naturally colonize the host, or be configured to colonize the host. The donor bacteria may then, in one preferred embodiment, disseminate the genetic constructs expressing the heterologous asRNA polynucleotides and/or quorum quenching molecules to naturally occurring host microorganisms and/or pathogenic bacteria in the surrounding environment. In this embodiment, once colonized in the target host, vertical transmission of the modified bacteria may be passed to the host's progeny, thus naturally replicating the pathogenic bacterial resistance to subsequent generations. Additionally, the modified bacteria may also be horizontally transmitted to the host population at large through the distribution of the modified bacteria into the environment as waste. Such a feature may allow for the one-time, or at least only periodic, administration of the genetically modified bacteria to the host and/or host's environment, generating a significant commercial advantage.

The inventive technology may further comprise methods and techniques to control the levels and timing of the expression of heterologous asRNA polynucleotides in the donor bacteria. In one preferred embodiment, the expression of one or more heterologous asRNA polynucleotides may be under the control of a novel gene switch. This gene switch may be controlled by a switch molecule, which may be a water-soluble and food-grade molecule that can be added to a host organism's environment or a food supply. The presence of this switch molecule may activate, for example heterologous asRNA production. In its absence, asRNA production may not occur, or may only occur at negligible levels.

Additional embodiments of the present invention may include methods and systems to optimize the effectiveness of heterologous asRNA polynucleotides. In one preferred embodiment, asRNA may be co-expressed and/or fused with chaperone proteins to protect the RNA molecules from degradation. Additional preferred embodiments may include the co-expression and/or fusing of secretion tags/moieties that may facilitate secretion and/or uptake of heterologous asRNA polynucleotides, increasing their effectiveness.

Bacterial endoribonucleases, exoribonucleases and RNA degradosomes may degrade non-coding RNA molecules such as asRNA. In one embodiment, the inventive technology may include modification of the previously identified delivery bacteria to have decreased expression, or inactivated function or activity of these protein families. This decrease or inactivation in expression and/or activity may inhibit or decrease single-stranded non-coding RNA species degradation. In one preferred embodiment, the previously identified host-specific bacteria may be genetically modified to efficiently express heterologous asRNA polynucleotides in an RNA endoribonuclease, exoribonuclease and/or degradosomes deficient background. In one preferred embodiment, a donor bacterium may lack, or have degraded RNase III function. In this preferred embodiment, these non-coding RNA molecule degradation genes may be knocked out by homologous recombination or other appropriate methods.

Another embodiment of the inventive technology may include systems and methods to facilitate the overexpression of host-specific bacterial genes known to enhance stabilization and/or mobilization of non-coding RNA molecules, such as asRNA and/or gRNA, as well as the mobilization and dissemination of their underlying genetic constructs, such as plasmids. In this preferred embodiment, one or more genes known to stabilize asRNA or mobilize genetic constructs such as plasmids may be overexpressed to enhance their lifetime and facilitate movement within host organism/cell/tissue.

In another embodiment, non-coding RNA molecules, such as heterologous asRNA polynucleotides, may be delivered by engineered and/or genetically modified bacteria that induce formation of intracellular connections, especially in non-optimal environmental conditions, or where certain essential nutrients are lacking in the surrounding environment. In this manner, bacteria may form nanotubes to exchange nutrients, genetic material and other chemical signals among connected cells and thus help to distribute metabolic functions within microbial communities. In this embodiment, auxotrophic bacteria may be genetically modified to induce formation of nanotubes which may allow the direct dissemination of asRNA from donor bacteria to target or recipient bacteria. In another embodiment, auxotrophic bacteria may be genetically modified to induce formation of nanotubes which may allow the dissemination of genetic constructs that encode for asRNA to target bacteria which lack the artificial genetic construct. In this configuration, under certain environmental or nutrient-deficient conditions, delivery bacteria may disseminate asRNA and/or the genetic constructs, such as plasmids, that encode an asRNA to other bacteria in the community. This action may help impair the expression of specific target genes among a large population of pathogenic bacteria.

In this embodiment, such genetic constructs may include transcription regulation portions, such as promoters, terminators, co-activators and co-repressors and similar control elements that may be regulated in prokaryotic, as well as eukaryotic systems. Such systems may allow for control of the type, timing and amount of heterologous asRNA polynucleotides, or other non-coding RNA molecules, expressed within the system. Additional embodiments may include genetic constructs that may be induced through outside factors, such as the presence of a specific protein or compound within a cell, such as stress related proteins generated in response to a pathogen, or even the proteins and other precursor compounds generated by pathogens and the like.

As noted above, in a preferred embodiment, one or more heterologous asRNA polynucleotides may be delivered to a target host/population of shrimp through genetically modified bacteria that may naturally, or be configured to, colonize and/or be symbiotic with the shrimp. In this embodiment, once colonized in the host, vertical transmission of the modified bacteria may be passed to the host's progeny, thus naturally replicating the pathogenic resistance to subsequent generations. In certain embodiments, genetically modified bacteria expressing one or more heterologous asRNA polynucleotides may colonize a shrimp throughout its lifecycle. For example, a genetically modified donor bacteria expressing one or more heterologous asRNA polynucleotides may colonize a shrimp while it is: an egg, a nauplius, a protozoea, a mysis, post-larval stage or an adult. In this embodiment, the colonized bacteria may express heterologous asRNA polynucleotides, that may be directed to be expressed and transported from the donor bacterium and taken up by a recipient pathogen bacteria and inhibit expression or one or more essential genes. Moreover, these colonized bacteria, having permanently and/or temporarily become a part of the host's natural microbiome, may continuously deliver the heterologous asRNA polynucleotides, in one instance via the intestine from the earliest larval stages to the adult stage, providing pathogen-specific mRNA down-regulation of essential pathogen genes throughout the host's lifecycle. In addition, as the donor bacterial vector may be an already naturally occurring part of the host's microbiome, its presence may not pose any risk to the organism, environment or end-consumers.

The inventive technology may include methods and techniques for the generation of host-specific bacteria, and in particular, host-specific enteric or symbiotic bacteria that may act as an appropriate donor vector for heterologous asRNA polynucleotides and quorum quenching molecules directed to bacterial pathogens that affect aquatic organisms. As an exemplary model, shrimp may be utilized as a target host. However, as can be appreciated by one of ordinary skill in the art, such methods and techniques may be applied to a variety of different organisms.

The term "aquaculture" as used herein includes the cultivation of aquatic organisms under controlled conditions.

The term "aquatic organism" and/or "aquatic animal" as used herein include organisms grown in water, either fresh or saltwater. Aquatic organisms/animals includes vertebrates, invertebrates, arthropods, fish, mollusks, including, shrimp (e.g., penaeid shrimp, *Penaeus esculentu, Penaeus setiferus, Penaeus stylirostris, Penaeus occidentalis, Penaeus japonicus, Penaeus vannamei, Penaeus monodon, Penaeus chinensis, Penaeus aztecus, Penaeus duorarum, Penaeus indicus*, and *Penaeus merguiensis, Penaeus californiensis, Penaeus semisulcatus, Penaeus monodon*, brine shrimp, freshwater shrimp, etc), crabs, oysters, scallop, prawn clams, cartilaginous fish (e.g., sea bream, trout, bass, striped bass, tilapia, catfish, salmonids, carp, catfish, yellowtail, carp zebrafish, red drum, etc), crustaceans, among others. Shrimp include shrimp raised in aquaculture as well.

The term "probiotic" refers to a microorganism, such as bacteria, that may colonize a host and provide a benefit. The term "probiotic" also refers to a microorganism, such as bacteria, that may colonize a host for a sufficient length of time to delver a therapeutic or effective amount of an heterologous asRNA polynucleotide and/or a quorum quenching molecule. A probiotic may include endosymbiotic bacteria, or naturally occurring flora that may permanently to temporarily colonize an animal, such as an aquatic organism. Probiotic organisms may also include algae, and fungi, such as yeast.

Specific examples of bacterial vectors include bacteria (e.g., cocci and rods), filamentous algae and detritus. Specific embodiments of transformable bacterial vectors cells that may be endogenous through all life cycles of the host may include all those listed herein. Additional embodiments may include one or more additional bacterial strains.

The term "operon" refers to a unit made up of linked genes.

The "quorum quencher" or "quorum quenching" molecules refers to heterologous or homologous molecules that inhibit QS and/or the formation of biofilms and/or reduce bacterial pathogenicity.

The present invention may include novel systems and methods for the expression of gRNA in a symbiotic donor bacterial species or strain which may be utilized by the CRISPR/Cas9 system to disrupt of target genes in pathogenic bacteria expressing CRISPR/Cas9 genes, such as dam, or QS genes. Generally, CRISPR/Cas9 may be used to generate a knock-out or disrupt target genes by co-expressing a gRNA specific to the gene to be targeted and the endonuclease Cas9. CRISPR may consist of two components: gRNA and a non-specific CRISPR-associated endonuclease (Cas9). The gRNA may be a short synthetic RNA composed of a scaffold sequence that may allow for Cas9-binding and a ~20 nucleotide spacer or targeting sequence which defines the genomic target to be modified. In one preferred embodiment, exemplary bacteria, such as symbiotic, endosymbiotic bacteria may be genetically modified to produce one or more gRNAs that are targeted to the genetic sequence of a pathogenic or other target gene and that can associate with the target bacteria's naturally occurring Cas9 endonuclease. In another preferred embodiment, exemplary bacteria, such as endophytic and/or enteric bacteria may be genetically modified to produce one or more gRNAs that are targeted to the genetic sequence of a pathogenic or other target gene, such as dam in *Vibrio*, and that can associate with the target bacteria's naturally occurring Cas9 endonuclease.

As used herein, the term "antisense RNA" or "asRNA" refers to an RNAi agent that is a single stranded oligonucleotide. In a typical asRNA, the single strand is complementary to all or a part of the target mRNA. The complementarity of an asRNA may be with any part of the specific gene transcript, i.e., at the 5' non-coding sequence, 3' non-translated sequence, introns, or the coding sequence. asRNA may be introduced into a cell to inhibit translation of a complementary mRNA by base pairing to it and physically obstructing the translation machinery. Antisense RNA anneal to a complementary mRNA target sequence, and translation of the mRNA target sequence is disrupted as a result of steric hindrance of either ribosome access or ribosomal read through. The antisense RNA mechanism is different from RNA interference (RNAi), a related process in which double-stranded RNA fragments (dsRNA, also called small interfering RNAs (siRNAs)) trigger catalytically mediated gene silencing, most typically by targeting the RNA-induced silencing complex (RISC) to bind to and degrade the mRNA. Annealing of a strand of the asRNA molecule to mRNA or DNA can result in fast degradation of duplex RNA, hybrid RNA/DNA duplex, or duplex RNA resembling precursor tRNA by ribonucleases in the cell, or by cleavage of the target RNA by the antisense compound itself As used herein, *Vibrio* is a genus of Gram-negative, facultative anaerobic bacteria possessing a curved-rod shape, with *Vibrio* sp. indicating a species within the genus *Vibrio*. In some embodiments, *Vibrio* sp. can comprise any one or more of the following *Vibrio* species, and in all possible combinations: *adaptatus, aerogenes, aestivus, aestuarianus, agarivorans, albensis, alfacsensis, alginolyticus, anguillarum, areninigrae, artabrorum, atlanticus, atypicus, azureus, brasiliensis, bubulus, calviensis, campbellii, casei, chagasii, cholera, cincinnatiensis, coralliilyticus, crassostreae, cyclitrophicus, diabolicus, diazotrophicus, ezurae, fischeri, fluvialis, fortis, furnissii, gallicus, gazo genes, gigantis, halioticoli, harveyi, hepatarius, hippocampi, hispanicus, hollisae, ichthyoenteri, indicus, kanaloae, lentus, litoralis, logei, mediterranei, metschnikovii, mimicus, mytili, natriegens, navarrensis, neonates, neptunius, nereis, nigripulchritudo, ordalii, orientalis, pacinii, parahaemolyticus, pectenicida, penaeicida, pomeroyi, ponticus, proteolyticus, rotiferianus, ruber, rumoiensis, salmonicida, scophthalmi, splendidus, superstes, tapetis, tasmaniensis, tubiashii, vulnificus, wodanis*, and *xuii*.

As used herein, the phrase "host" or "target host" refers to a organism or population carrying a disease-causing pathogen, or an organism or population that is susceptible to a disease-causing pathogen. A "host" or "target host" may further include an organism or population capable of carrying a disease-causing pathogen.

As used herein, the terms "controlling" and/or "biocontrol" refer to reducing and/or regulating pathogen/disease progression and/or transmission.

As used herein, "vaccine" refers to compositions that result in both active and passive immunizations. Both polypeptides and polynucleotides and their expressed gene products are referred to as vaccines herein. A feed may include a treated bacteria configured to express an heterologous RNA polynucleotide and/or a quorum quenching molecule may also be a vaccine. Feeding treated feed to an animal may be a vaccination.

As used herein, the phrase "feed" refers to animal consumable material introduced as part of the feeding regimen or applied directly to the water in the case of aquatic animals. A "treated feed" refers to a feed treated with a treated bacteria configured to express bacteria polynucleotide and of quorum quenching molecules as generally described herein. A "feed may also be a or a shrimp culture pond/aquaculture inoculum.

The term "nucleic acid" as used herein, refers to a polymer of ribonucleotides or deoxyribonucleotides. Typically, "nucleic acid or "nucleic acid agent" polymers occur in either single or double-stranded form, but are also known to form structures comprising three or more strands. The term "nucleic acid" includes naturally occurring nucleic acid polymers as well as nucleic acids comprising known nucleotide analogs or modified backbone residues or linkages, which are synthetic, naturally occurring, and non-naturally occurring, which have similar binding properties as the reference nucleic acid, and which are metabolized in a manner similar to the reference nucleotides. Exemplary analogs include, without limitation, phosphorothioates, phosphoramidates, methyl phosphonates, chiral-methyl phosphonates, 2-O-methyl ribonucleotides, and peptide-nucleic acids (PNAs). "DNA", "RNA", "polynucleotides", "polynucleotide sequence", "oligonucleotide", "nucleotide", "nucleic acid", "nucleic acid molecule", "nucleic acid sequence", "nucleic acid fragment", and "isolated nucleic acid fragment" are used interchangeably herein.

The term "recombinant" when used with reference, e.g., to a cell, or nucleic acid, protein, or vector, indicates that the cell, organism, nucleic acid, protein or vector, has been modified by the introduction of a heterologous nucleic acid or protein or the alteration of a native nucleic acid or protein, or that the cell is derived from a cell so modified. Thus, for example, recombinant cells may express genes that are not found within the native (non-recombinant or wild-type) form of the cell or express native genes that are otherwise abnormally expressed, over-expressed, under expressed or not expressed at all.

The terms "genetically modified," "bio-transformed," "transgenic", "transformed", "transformation", and "transfection" are similar in meaning to "recombinant". "Transformation", "transgenic", and "transfection" refer to the transfer of a polynucleotide into the genome of a host organism or into a cell. Such a transfer of polynucleotides can result in genetically stable inheritance of the polynucleotides or in the polynucleotides remaining extra-chromosomally (not integrated into the chromosome of the cell). Genetically stable inheritance may potentially require the transgenic organism or cell to be subjected for a period of time to one or more conditions which require the transcription of some or all of the transferred polynucleotide in order for the transgenic organism or cell to live and/or grow. Polynucleotides that are transformed into a cell but are not integrated into the host's chromosome remain as an expression vector within the cell. One may need to grow the cell under certain growth or environmental conditions in order for the expression vector to remain in the cell or the cell's progeny. Further, for expression to occur, the organism or cell may need to be kept under certain conditions. Host organisms or cells containing the recombinant polynucleotide can be referred to as "transgenic" or "transformed" organisms or cells or simply as "transformants", as well as recombinant organisms or cells.

The term "vector" refers to some means by which DNA, RNA, a protein, or polypeptide can be introduced into a host. The polynucleotides, protein, and polypeptide which are to be introduced into a host can be therapeutic or prophylactic in nature; can encode or be an antigen; can be regulatory in nature; etc. There are various types of vectors including virus, plasmid, bacteriophages, cosmids, and bacteria.

An "expression vector" is a nucleic acid capable of replicating in a selected host cell or organism. An expression vector can replicate as an autonomous structure, or alternatively can integrate, in whole or in part, into the host cell chromosomes or the nucleic acids of an organelle, or it may be used as a shuttle for delivering foreign DNA to cells, and thus replicate along with the host cell genome. Thus, expression vectors are polynucleotides capable of replicating in a selected host cell, organelle, or organism, e.g., a plasmid, virus, artificial chromosome, nucleic acid fragment, and for which certain genes on the expression vector (including genes of interest) are transcribed and translated into a polypeptide or protein within the cell, organelle or organism; or any suitable construct known in the art, which comprises an "expression cassette". In contrast, as described in the examples herein, a "cassette" is a polynucleotide containing a section of an expression vector of this invention. The use of the cassette assists in the assembly of the expression vectors. An expression vector is a replicon, such as plasmid, phage, virus, chimeric virus, or cosmid, and which contains the desired polynucleotide sequence operably linked to the expression control sequence(s).

A polynucleotide sequence is "operably linked" to an expression control sequence(s) (e.g., a promoter and, optionally, an enhancer) when the expression control sequence controls and regulates the transcription and/or translation of that polynucleotide sequence. As used herein, the phrase "gene product" refers to an RNA molecule or a protein. Moreover, the term "gene" may sometime refer to the genetic sequence, the transcribed and possibly modified mRNA of that gene, or the translated protein of that mRNA.

The present teachings contemplate the targeting of homologs and orthologs according to the selected pathogen species, for example species of *Vibrio*. Homologous sequences include both orthologous and paralogous sequences. The term "paralogous" relates to gene-duplications within the genome of a species leading to paralogous genes. The term "orthologous" relates to homologous genes in different organisms due to ancestral relationship. Thus, orthologs are evolutionary counterparts derived from a single ancestral gene in the last common ancestor of given two species (Koonin EV and Galperin MY (Sequence—Evolution—Function: Computational Approaches in Comparative Genomics. Boston: Kluwer Academic; 2003. Chapter 2, Evolutionary Concept in Genetics and Genomics. Available from: www.ncbi.nlm.nih.gov/books/NBK20255/) and therefore have great likelihood of having the same function. As such, orthologs usually play a similar role to that in the original species in another species.

Homology (e.g., percent homology, sequence identity+sequence similarity) can be determined using any homology comparison software computing a pairwise sequence alignment. As used herein, "sequence identity" or "identity" in the context of two nucleic acid or polypeptide sequences includes reference to the residues in the two sequences which are the same when aligned. When percentage of sequence identity is used in reference to proteins it is recognized that residue positions which are not identical often differ by conservative amino acid substitutions, where amino acid residues are substituted for other amino acid residues with similar chemical properties (e.g. charge or hydrophobicity) and therefore do not change the functional properties of the molecule. Where sequences differ in conservative substitutions, the percent sequence identity may be adjusted upwards to correct for the conservative nature of the substitution. Sequences which differ by such conservative substitutions are to have "sequence similarity" or "similarity". Means for making this adjustment are well-known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., according to the algorithm of Henikoff S and Henikoff JG. [Amino acid substitution matrices from protein blocks. Proc. Natl. Acad. Sci. U.S.A. 1992, 89(22): 10915-9].

According to a specific embodiment, a homolog sequences are at least 60%, 65%, 70%, 75%, 80%, 85%, 90%, 95% or even identical to the sequences (nucleic acid or amino acid sequences) provided herein. Homolog sequences of any of SEQ ID Nos 1-4 of between 50%-99% may be included in certain embodiments of the present invention.

Downregulating expression of a pathogen gene product can be monitored, for example, by direct detection of gene transcripts (for example, by PCR), by detection of polypeptide(s) encoded by the gene (for example, by Western blot or immunoprecipitation), by detection of biological activity of polypeptides encoded by the gene (for example, catalytic activity, ligand binding, and the like), or by monitoring changes in the host (for example, reduced motility of the host etc.). Additionally, or alternatively downregulating expression of a pathogen gene product may be monitored by measuring pathogen levels (e.g. bacterial levels etc.) in the host as compared to a wild type (i.e. control) host not treated by the agents of the invention.

As used herein, the term "interfering RNA molecules" or "interfering RNA" refers to an RNA polynucleotide which is capable of inhibiting or "silencing" the expression of a target gene in a pathogen. In certain embodiments, an "interfering RNA molecule" or "interfering RNA" may include an asRNA or heterologous asRNA. The inhibitory RNA sequence can be greater than 90% identical or even 100% identical, to the portion of the target gene transcript. Alternatively, the duplex region of the RNA may be defined functionally as a nucleotide sequence that is capable of hybridizing with a portion of the target gene transcript under stringent conditions (e.g., 400 mM NaCl, 40 mM PIPES pH 6.4, 1 mM EDTA, 60 degrees C. hybridization for 12-lb hours; followed by washing). The length of the single-stranded nucleotide sequences complementary to the target gene transcript may be at least about 18, 19, 21, 25, 50, 100, 200, 300, 400, 491, 500, 550, 600, 650, 700, 750, 800, 900, 1000 or more bases. In some embodiments of the invention, the length of the double-stranded nucleotide sequence is approximately from about 18 to about 530, or longer, nucleotides in length.

It will be noted that the asRNA can be defined in terms of the nucleic acid sequence of the DNA encoding the target gene transcript, and it is understood that a asRNA sequence corresponding to the coding sequence of a gene comprises an RNA complement of the gene's coding sequence, or other sequence of the gene which is transcribed into RNA.

For example, in order to silence the expression of an mRNA of interest, synthesis of the asRNA suitable for use with some embodiments of the invention can be selected as follows. First, the mRNA sequence is scanned including the 3' UTR and the 5' UTR. Second, the mRNA sequence is compared to an appropriate genomic database using any sequence alignment software, such as the BLAST software available from the NCBI server (wwwdotncbidotnlmdotnih-dotgov/BLAST/). Putative regions in the mRNA sequence which exhibit significant homology to other coding sequences are filtered out. Qualifying target sequences are selected as templates for asRNA synthesis. Preferred sequences are those that have little homology to other genes in the genome to reduce an "off-target" effect. It will be appreciated that the RNA silencing agent of some embodiments of the invention need not be limited to those molecules containing only RNA, but further encompasses chemically-modified nucleotides and non-nucleotides.

According to a specific embodiment, the vector for the heterologous asRNA polynucleotide and/or quorum-quenching molecules, or donor is bacteria. In other embodiments, the donor is an algae cell. Various algae species can be used in accordance with the teachings of the invention since they are a significant part of the diet for many kinds of hosts that feed opportunistically on microorganisms as well as on small aquatic animals such as rotifers. Examples of algae that can be used in accordance with the present teachings include, but are not limited to, blue-green algae as well as green algae. Specifically, *Actinastrum hantzschii, Ankistrodesmus falcatus, Ankistrodesmus spiralis, Aphanochaete elegans, Chlamydomonas* sp., *Chlorella ellipsoidea, Chlorella pyrenoidosa, Chlorella variegate, Chlorococcum hypnosporum, Chodatella brevispina, Closterium acerosum, Closteriopsis acicularis, Coccochloris peniocystis, Crucigenia lauterbomii, Crucigenia tetrapedia, Coronastrum ellipsoideum, Cosmarium botrytis, Desmidium swartzii, Eudorina elegans, Gloeocystis gigas, Golenkinia minutissima, Gonium multicoccum, Nannochloris oculata, Oocystis marssonii, Oocystis minuta, Oocystis pusilla, Palmella texensis, Pandorina morum, Paulschulzia pseudovolvox, Pediastrum clathratum, Pediastrum duplex, Pediastrum simplex, Planktosphaeria gelatinosa, Polyedriopsis spinulosa, Pseudococcomyxa adhaerans, Quadrigula closterioides, Radiococcus nimbatus, Scenedesmus basiliensis, Spirogyra pratensis, Staurastrum gladiosum, Tetraedron bitridens, Trochiscia hystrix. Anabaena catenula, Anabaena spiroides, Chroococcus turgidus, Cylindrospermum licheniforme, Bucapsis* sp. (U. Texas No. 1519), *Lyngbya spiralis, Microcystis aeruginosa, Nodularia spumigena, Nostoc linckia, Oscillatoria lutea, Phormidiumfaveolarum, Spinilina platensis.*

In a further embodiment, a composition including a genetically modified bacteria configured to express asRNA and/or quorum-quenching molecules may be formulated as a water dispersible granule or powder that may further be configured to be dispersed into the environment. In yet a further embodiment, the compositions of the present invention may also comprise a wettable powder, spray, emulsion, colloid, aqueous or organic solution, dust, pellet, or colloidal concentrate. Dry forms of the compositions may be formulated to dissolve immediately upon wetting, or alternatively, dissolve in a controlled-release, sustained-release, or other time-dependent manner. Alternatively or additionally, the composition may comprise an aqueous solution. Such aqueous solutions or suspensions may be provided as a concentrated stock solution which is diluted prior to application, or alternatively, as a diluted solution ready-to-apply. Such compositions may be formulated in a variety of ways. They may be employed as wettable powders, granules or dusts, by mixing with various inert materials, such as inorganic minerals (silicone or silicon derivatives, phyllosilicates, carbonates, sulfates, phosphates, and the like) or botanical materials (powdered corncobs, rice hulls, walnut shells, and the like). The formulations or compositions containing genetically modified bacteria may include spreader-sticker adjuvants, stabilizing agents, other pesticidal additives, or surfactants. Liquid formulations may be employed as foams, suspensions, emulsifiable concentrates, or the like. The ingredients may include biological agents, surfactants, emulsifiers, dispersants, or polymers.

Compositions of the invention, which may include genetically modified symbiotic donor bacteria expressing heterologous RNA polynucleotides and/or a quorum quenching molecule, can be used for the bio-control of pathogens in an animal or other host. Such an application comprises administering to a host an effective amount of the composition which expresses from the donor sufficient heterologous RNA polynucleotides and/or a quorum quenching molecule that may be transported out of the donor and taken-up by the target pathogen, thus interfering with expression of a target essential gene, and thereby controlling the pathogen and/or pathogen's disease causing effects on the host.

Compositions of the invention can be used for the control of pathogen gene expression and/or QS and its effects described herein, in vivo. Such an application comprises administering to target host, such as shrimp, an effective amount of the composition which suppresses the pathogen carried by the host, reducing or eliminating the disease state in the host as well as rendering the pathogen non-transferable, for example to a host population. Thus, regardless of the method of application, the amount of the genetically modified symbiotic donor bacteria expressing heterologous RNA polynucleotides and/od quorum quenching molecules that may be applied at an effective amount to kill or suppress a pathogen and/or suppress QS or its effects in a pathogen, will vary depending on factors such as, for example, the specific host to be controlled, the type of pathogen, in some instances the water source to be treated, the environmental conditions, and the method, rate, and quantity of application of the composition. The concentration of the composition that is used for environmental, systemic or foliar application will vary widely depending upon the nature of the particular formulation, means of application, environmental conditions, and degree of biocidal activity.

According to some embodiments, the heterologous asRNA polynucleotide and/or a quorum quenching molecule is provided in amounts effective to reduce or suppress expression of at least one pathogen gene product and/or reduce or suppress QS and/or reduce or suppress biofilm formation. As used herein "a suppressive amount" or "an effective amount" or a "therapeutically effective amount" refers to an amount of asRNA which is sufficient to down-regulate (reduce expression of) the target gene by at least 5%, 10% 20%, 30%, 40%, 50%, or more, say 60%, 70%, 80%, 90%, or even up to 100%. All ranges include the ranges in between those specifically stated. As used herein "a suppressive amount" or "an effective amount" or a quorum quenching molecule refers to an amount of a quorum quenching molecule which is sufficient to reduce QS and/or biofilm formation in a target pathogen, preferable an EMS-causing pathogen, by at least 5%, 10% 20%, 30%, 40%, 50%, or more, say 60%, 70%, 80%, 90%, or even up to 100%. All ranges include the ranges in between those specifically stated.

As used herein, the term "gene" or "polynucleotide" refers to a single nucleotide or a polymer of nucleic acid residues of any length. The polynucleotide may contain deoxyribonucleotides, ribonucleotides, and/or their analogs, and may be double-stranded or single stranded. A polynucleotide can comprise modified nucleic acids (e.g., methylated), nucleic acid analogs or non-naturally occurring nucleic acids, and can be interrupted by non-nucleic acid residues. For example, a polynucleotide includes a gene, a gene fragment, cDNA, isolated DNA, mRNA, tRNA, rRNA, and isolated RNA of any sequence, recombinant polynucleotides, primers, probes, plasmids, and vectors. Included within the definition, are nucleic acid polymers that have been modified, whether naturally or by intervention.

As used herein the terms "approximately" or "about" refer to ±10%. Whenever a numerical range is indicated herein, it is meant to include any cited numeral (fractional or integral) within the indicated range. The phrases "ranging/ranges between" a first indicated number and a second indicated number and "ranging/ranges from" a first indicated number "to" a second indicated number are used herein interchangeably and are meant to include the first and second indicated numbers and all the fractional and integral numerals there between.

The terms "comprises", "comprising", "includes", "including", "having" and their conjugates mean "including but not limited to." The term "consisting of" means "including and limited to". The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references, unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity, and should not be construed as an inflexible limitation on the scope of the invention. Accordingly, the description of a range should be considered to have specifically disclosed all the possible subranges as well as individual numerical values within that range. For example, description of a range, such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

As used herein the term "system" and/or "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts. As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

As used herein, "symbiotic" or "symbionts" generally refers to a bacterium that is a symbiont of a host. It may also include bacteria that persist throughout the life-cycle of a host, either internally or externally, and may further be passed horizontally to the offspring or eggs of a host. Symbionts can also include bacteria that colonize outside of host's cells and even in the tissue, lymph or secretions of the host. Endosymbionts generally refers to a subgroup of internal symbionts.

As used herein, "transbiotic" refers to the production of RNA polynucleotides or quorum quenchers inside naturally occurring or symbiotic bacterium that live within the target host organism that are designed to inhibit expression of target host or pathogen genes.

This invention utilizes routine techniques in the field of molecular biology. Basic texts disclosing the general methods of use in this invention include Green and Sambrook, 4th ed. 2012, Cold Spring Harbor Laboratory; Kriegler, Gene Transfer and Expression: A Laboratory Manual (1993); and Ausubel et al., eds., Current Protocols in Molecular Biology, 1994-current, John Wiley & Sons. Unless otherwise noted, technical terms are used according to conventional usage. Definitions of common terms in molecular biology maybe found in e.g., Benjamin Lewin, Genes IX, published by Oxford University Press, 2007 (ISBN 0763740632); Krebs, et al. (eds.), The Encyclopedia of Molecular Biology, published by Blackwell Science Ltd., 1994 (ISBN 0-632-02182-9); and Robert A. Meyers (ed.), Molecular Biology and Biotechnology: a Comprehensive Desk Reference, published by VCH Publishers, Inc., 1995 (ISBN 1-56081-569-8).

The invention now being generally described will be more readily understood by reference to the following examples, which are included merely for the purposes of illustration of certain aspects of the embodiments of the present invention. The examples are not intended to limit the invention, as one of skill in the art would recognize from the above teachings and the following examples that other techniques and methods can satisfy the claims and can be employed without departing from the scope of the claimed invention. Indeed, while this invention has been particularly shown and described with references to preferred embodiments thereof, it will be understood by those skilled in the art that various changes in form and details may be made therein without departing from the scope of the invention encompassed by the appended claims.

EXAMPLES

Example 1: Preventing EMS with Enteric Bacteria Disrupting Quorum Sensing Construct Design To degrade AI-1, the present inventors over-expressed the lactonase, AidH, from Ochrobactrum. Unlike *B. cereus* AiiA lactonase, the catalytic activity of AidH does not require zinc which may be in present only in limited quantities in sea water and/or artificial aquaculture environments. The present inventors placed the aidH gene under the control of strong Pupp promoter that is operably in both gram-positive and gram-negative bacteria. A Pupp-aidH expression cassette was cloned both in the pAD43 shuttle vector and in pACYC184. To absorb AI-2 from environment the present inventors cloned and overexpressed *E. coli* lsr operon. In attempt to decrease concentration of AI-1 and AI-2 signal molecules, the present inventors further co-express AI-1 and AI-2 quenching constructs using compatible plasmid constructs. Plasmid design is described in Materials and Methods. All plasmids were transformed into enteric natural isolate *Enterobacter* sp.

Example 2: Co-Cultivation of *Vibrio harveyi* with aidH-Expressing AG1 Constructs Leads to Decrease in *Vibrio* Luminescence As generally shown in FIG. 1, the present inventors demonstrated the quorum-quenching properties of the constructed strains. In this embodiment, the present inventors performed luminescence-quenching experiments with an array of *V. harveyi* strains that differentially respond to AI-1 and AI-2. For this assay, quorum-quenching AG1 constructs were co-cultivated with luminescence-emitting *Vibrio* strains over 12-16 hours in a 96-well assay plates with a transparent bottom. Control constructs expressing neutral genes (e.g. AG1-pOX or AG1-pLuc) were used as control strains in parallel experiment. During the bacterial growth, both luminescence and culture optical density were monitored. As observed by the present inventors, luminescence of *Vibrio* strains is sharply increased in the early stationary growth phase manifesting bacterial quorum sensing.

Figure 2A:
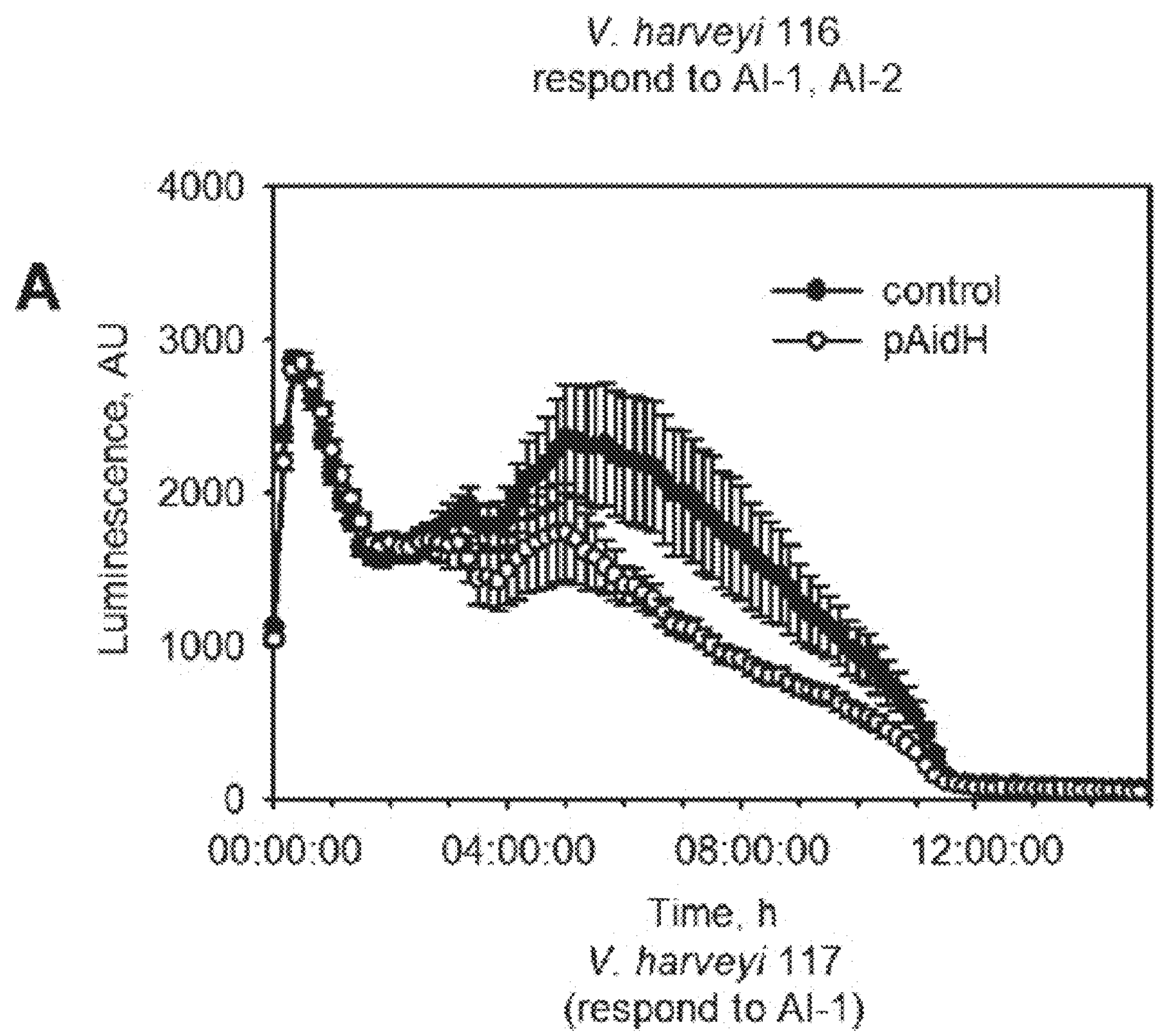
FIG. 2: Quorum quenching bacteria expressing lactonase AidH specifically decrease luminescence of *V. harveyi*. (A) Co-cultivation with Ag1-pAidH decrease luminescence of wt *V. harveyi* that responds to all autoinducers. (B) Co-cultivation with Ag1-pAidH strongly decreases luminescence of *V. harveyi* 117 that responds to AI-1 only. (C) Co-cultivation with Ag1-pAidH does not decrease luminescence of *V. harveyi* 118 that does not respond to AI-2.
Figure 2B:
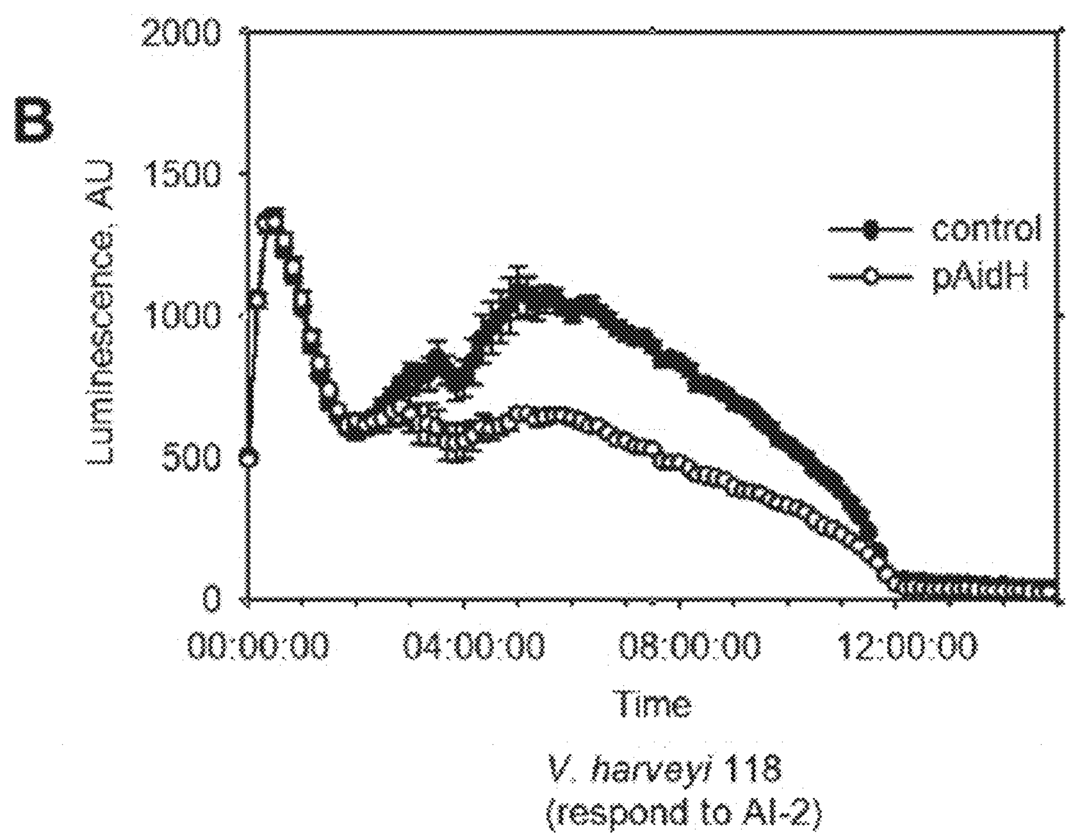
Figure 2C:
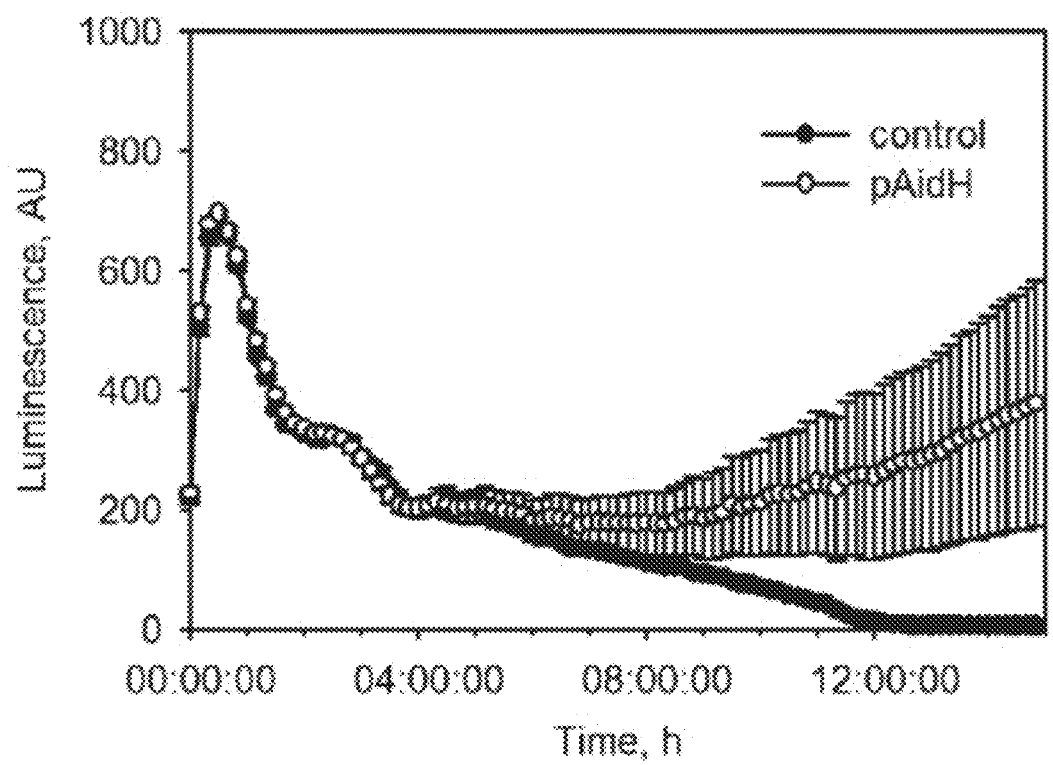
Figure 11A:
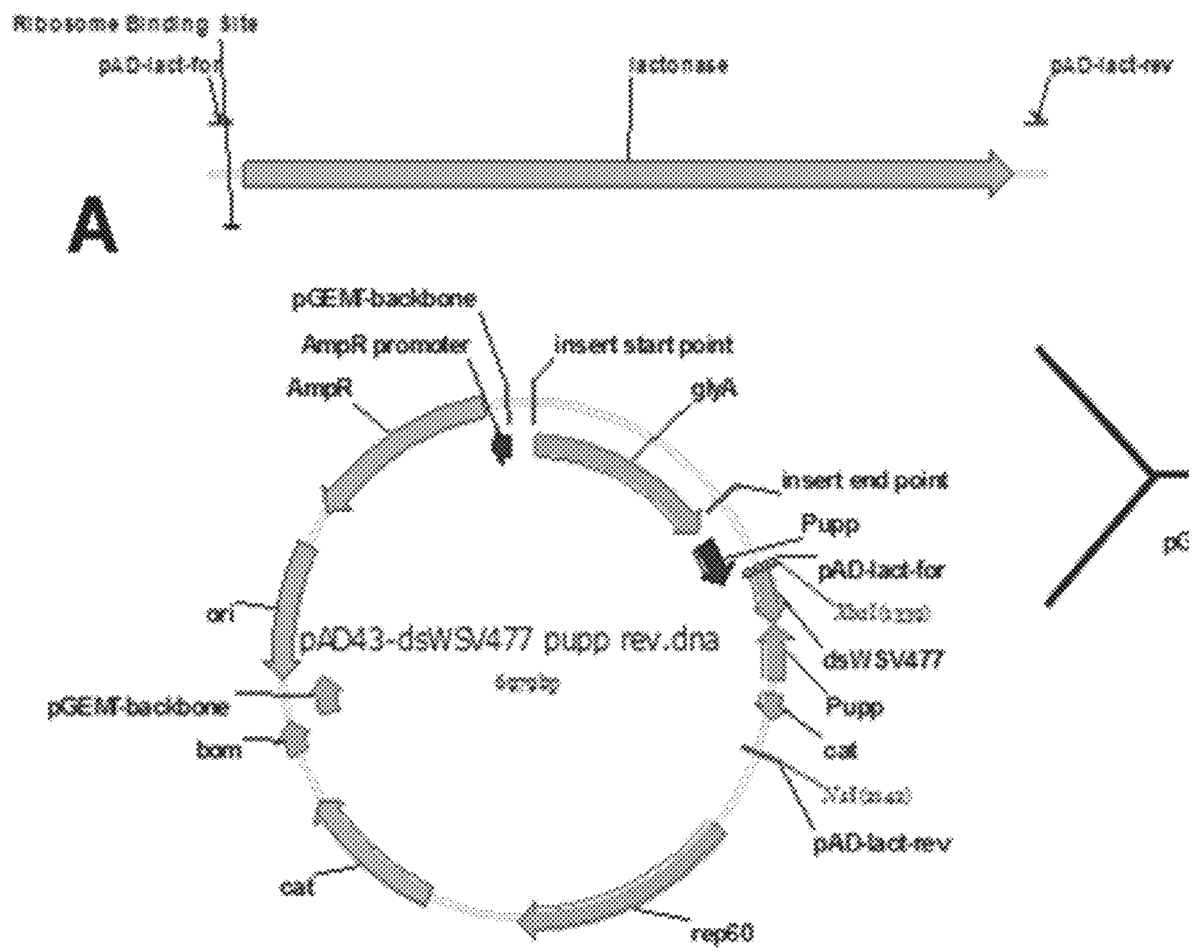
FIG. 11A-C: Maps of plasmids used in this work. Plasmids design is described in Material and Methods section. Sequences of the genes used for cloning of pAidH and pLsr plasmids as listed below under the section entitled SEQUENCE LISTING.
Figure 11B:
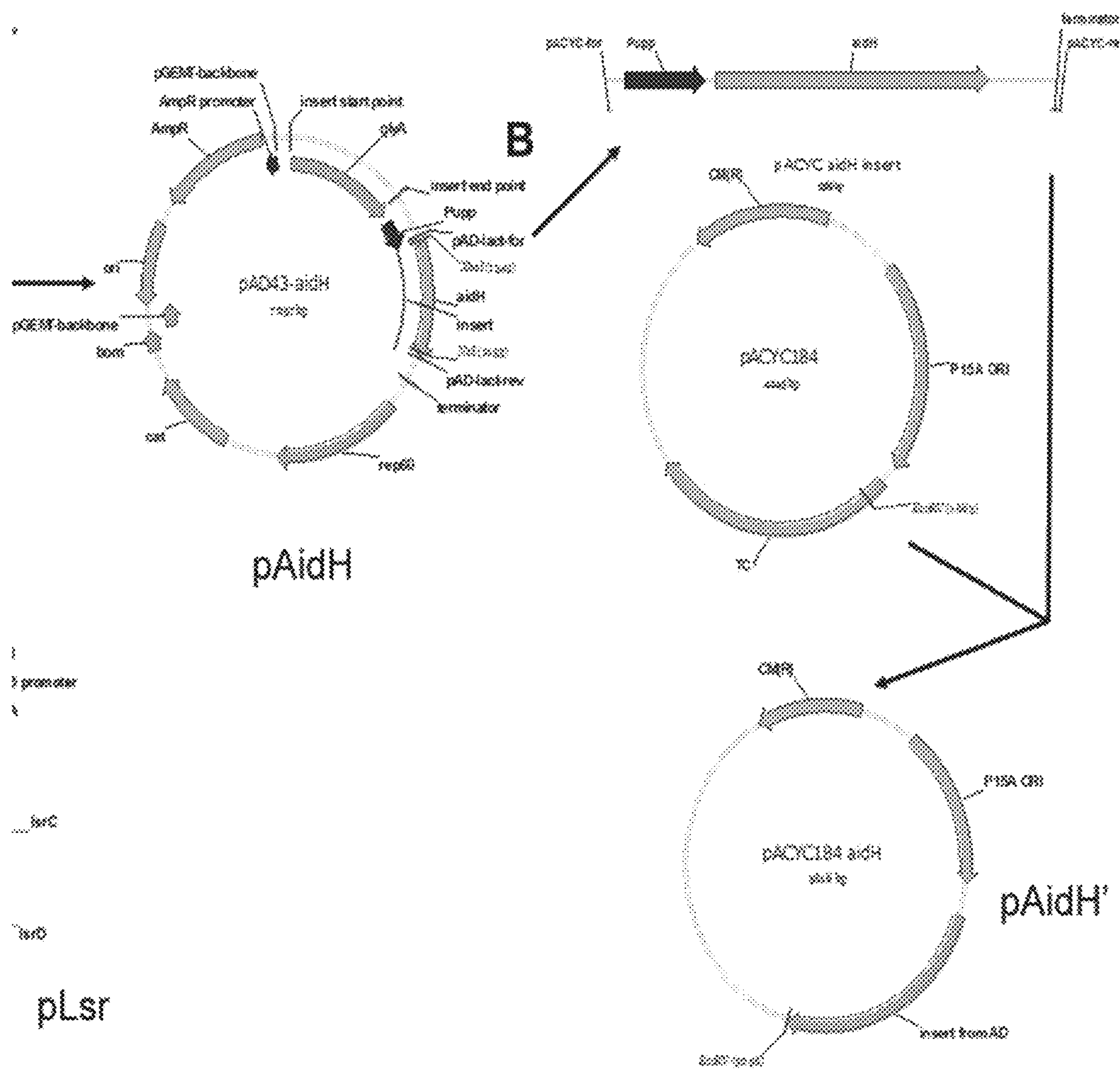
Figures 1, 11B:
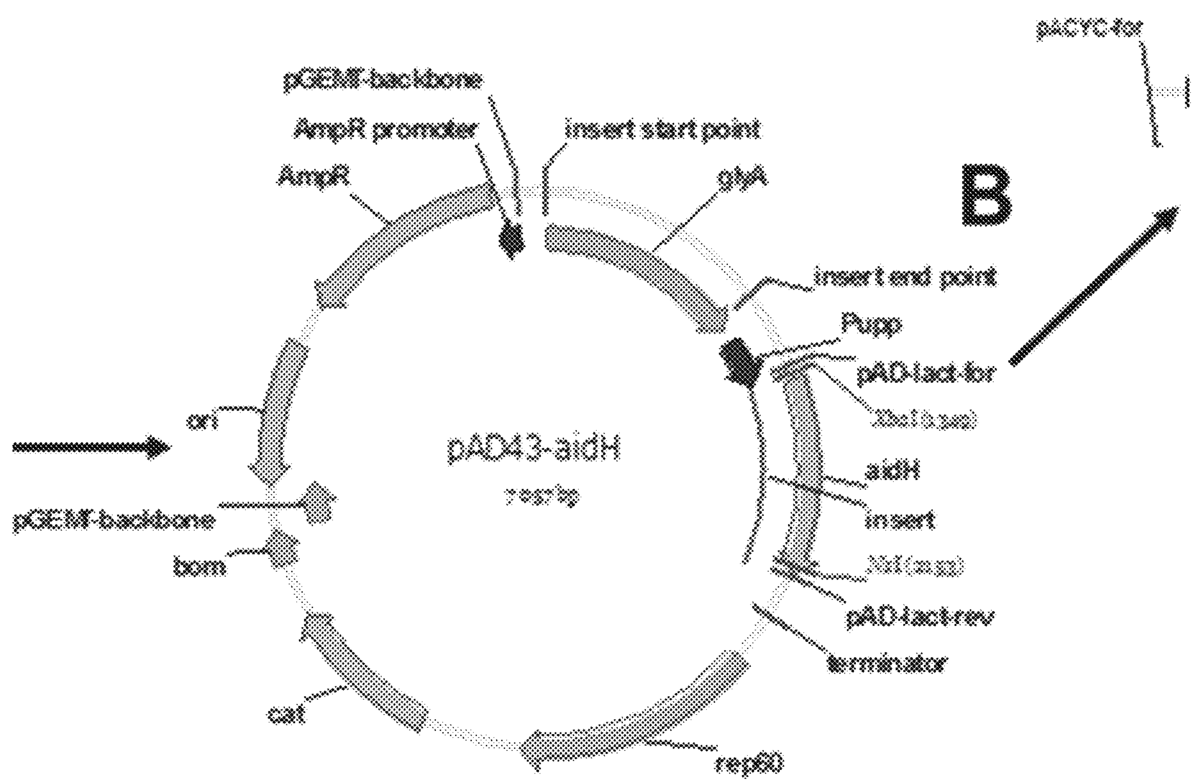
Figures 2, 11B:
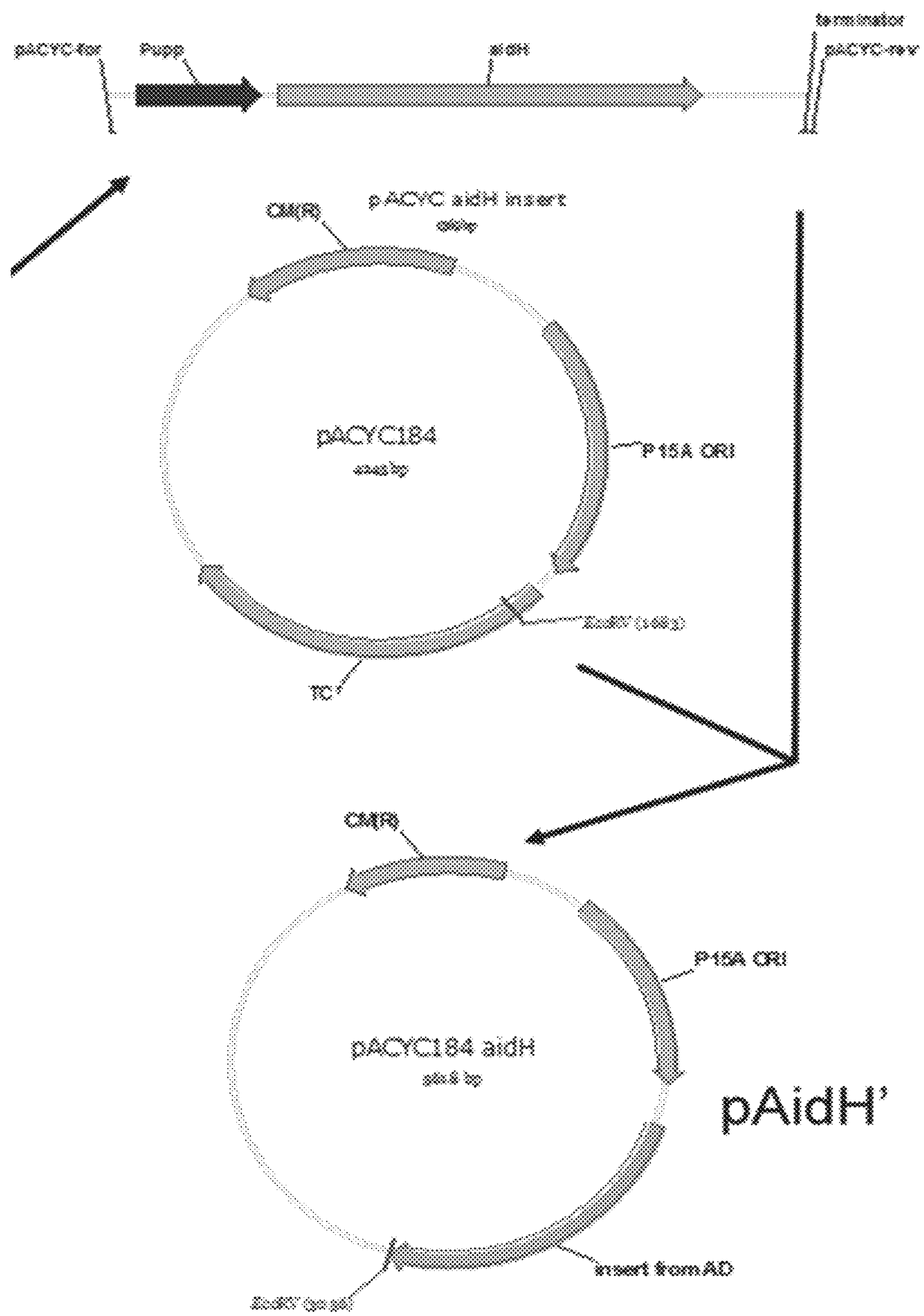
Figure 11C:
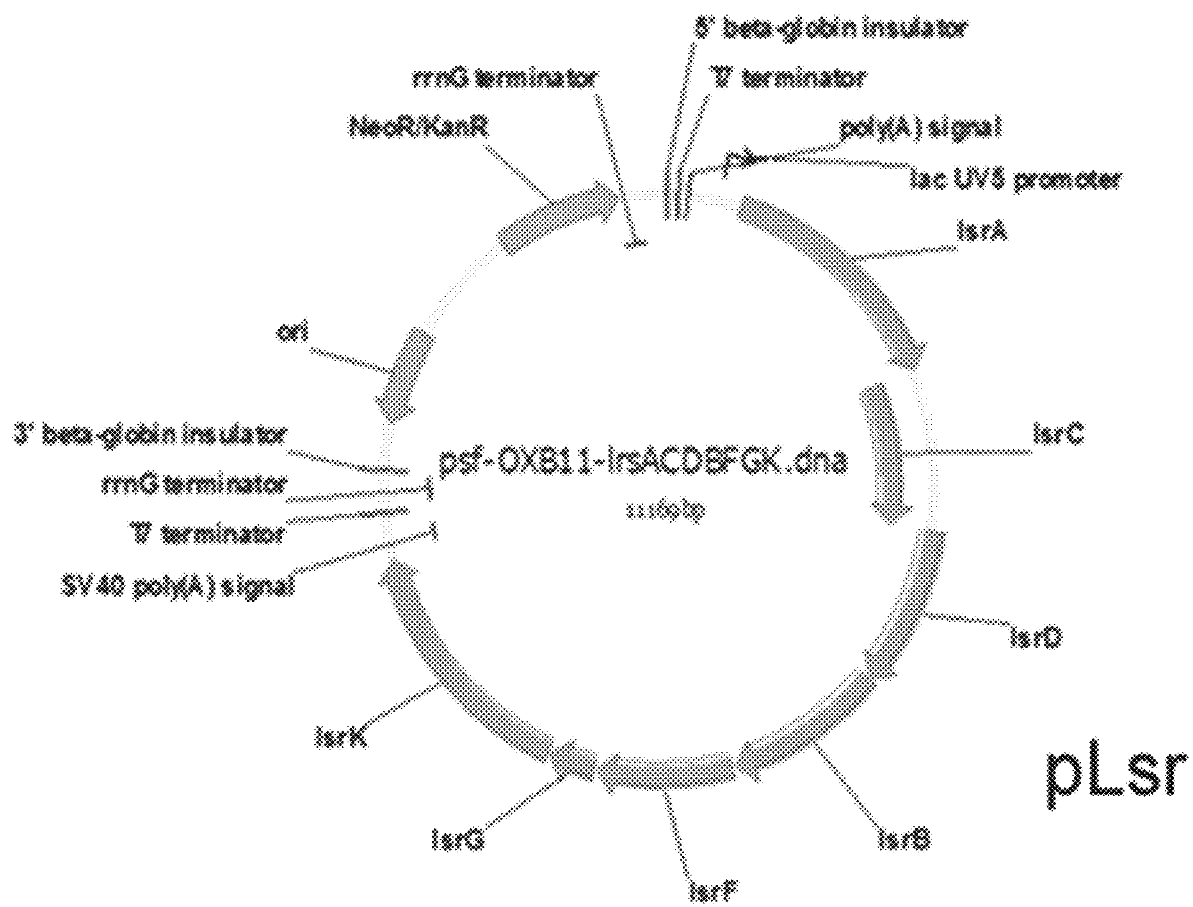
Figure 12:
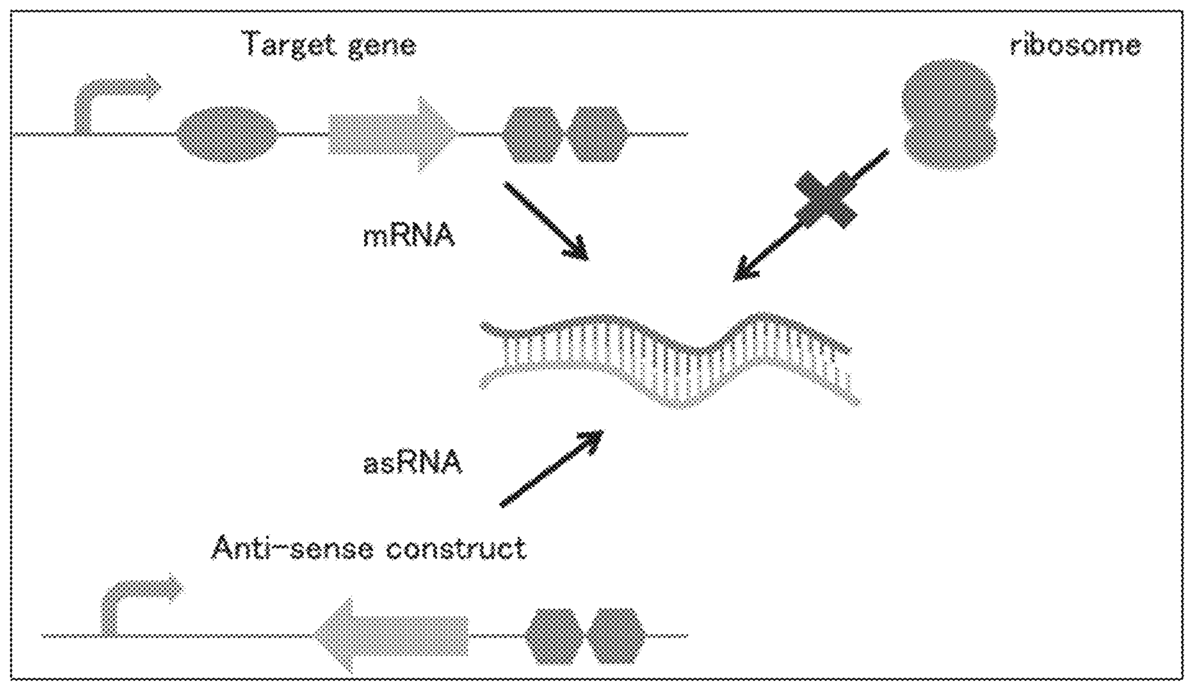
FIG. 12: Schematic of asRNA expressed in a genetically modified bacteria.
Figure 13:
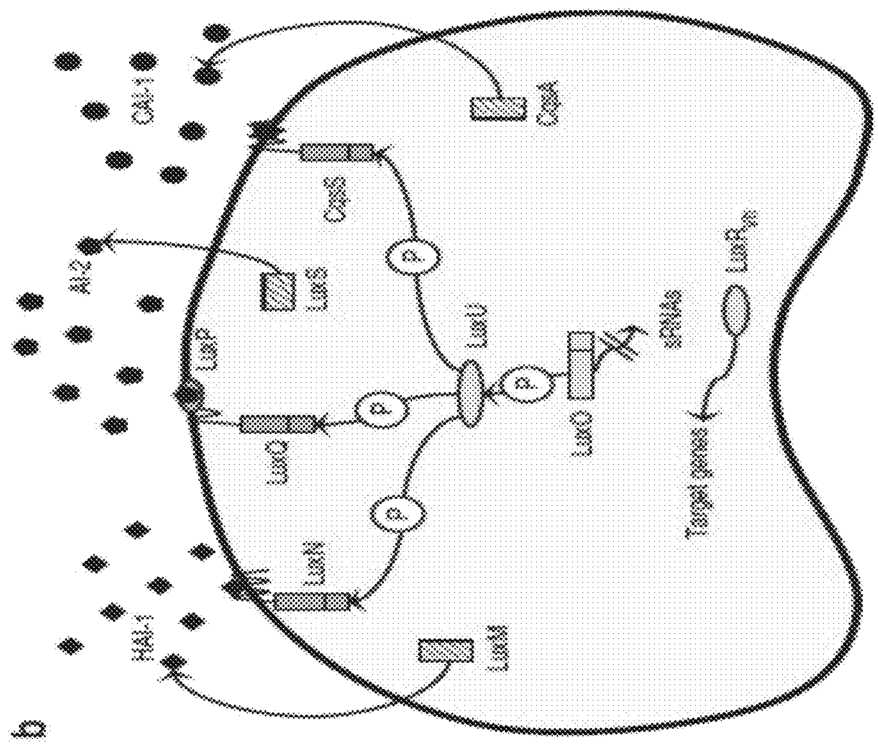
FIG. 13: Quorum sensing in *Vibrio harveyi*. The LuxM, LuxS and CqsA enzymes synthesize the autoinducers HAI-1, AI-2 and CAI-1 respectively. These autoinducers are detected at the cell surface by the LuxN, LuxP-LuxQ and CqsS receptor proteins respectively. A. At low signal molecule concentration, the receptors autophosphorylate and transfer phosphate to LuxO via LuxU. Phosphorylation activates LuxO, which together with s54 activates the production of small regulatory RNAs (sRNAs). These sRNAs, together with the chaperone Hfq, destabilize the mRNA encoding the response regulator LuxRVh. Therefore, in the absence of autoinducers, the LuxRVh protein is not produced. B. In the presence of high concentrations of the autoinducers, the receptor proteins switch from kinases to phosphatases, which results in dephosphorylation of LuxO. Dephosphorylated LuxO is inactive and therefore, the sRNAs are not formed and the response regulator LuxRVh is produced.
Figure 13:
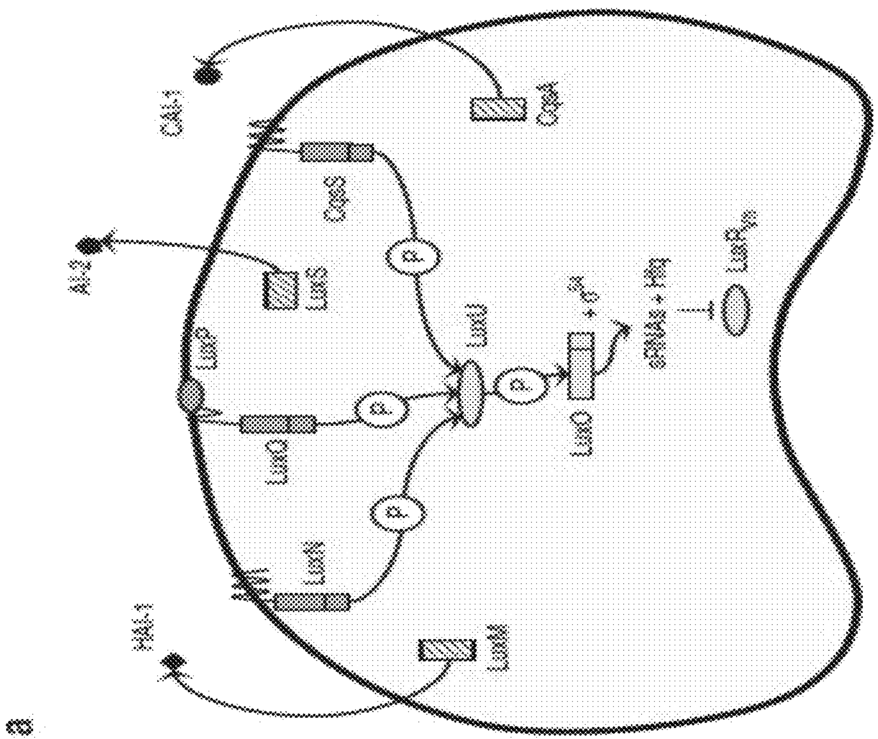
Figure 14:
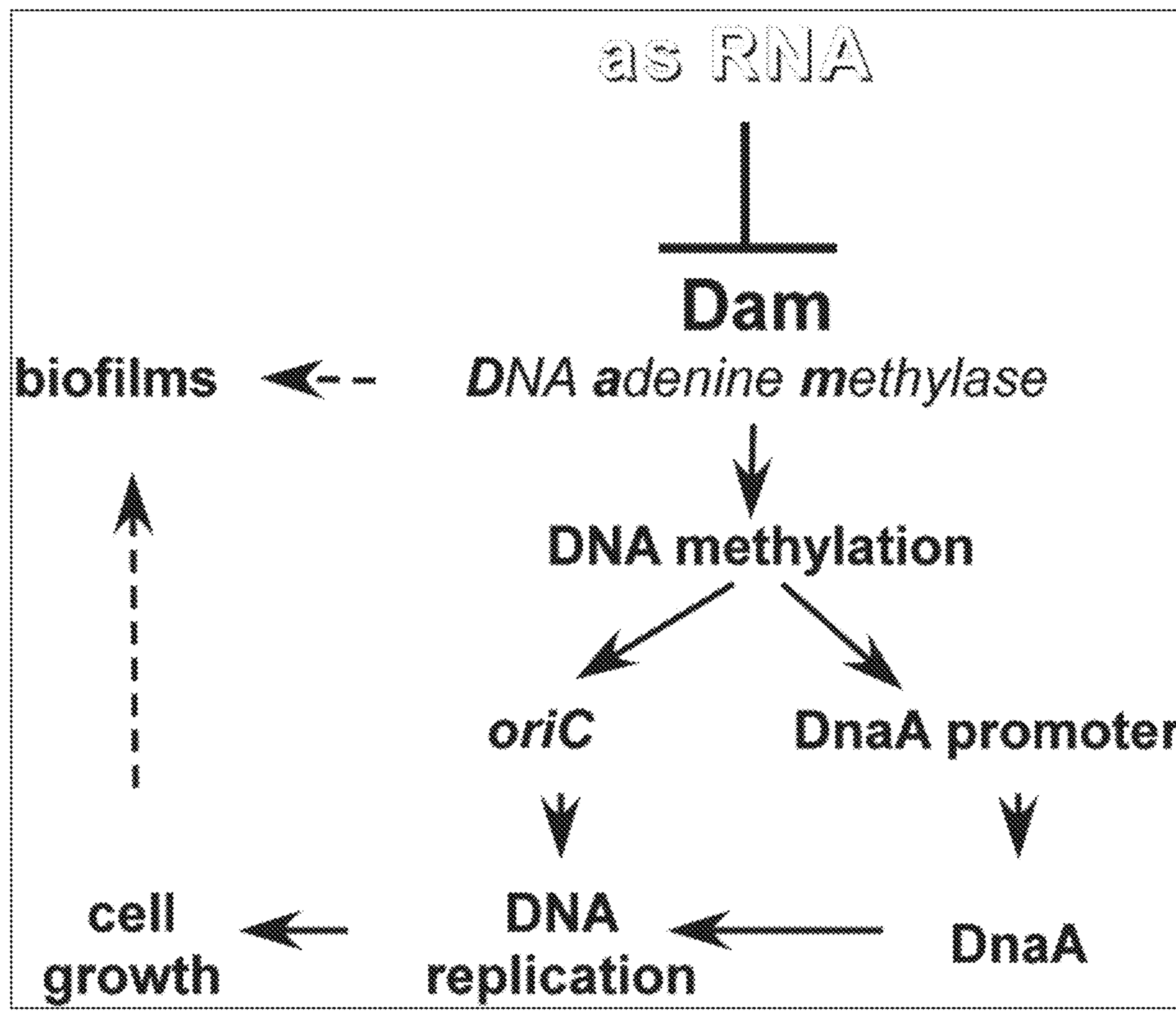
FIG. 14: Potential effects of asRNA blocking expression of the dam gene. Decrease in methylation of origin/DnaA promoter region leads to disruption of the DNA replication regulation loop and inhibition of *Vibrio* cell division. Repression of Dam expression inhibits biofilm formation by unknown mechanisms that may include transcriptional inhibition of specific gene promoters resulting in a slowdown of cell growth.

Again, as shown in FIG. 2, a AI-1, AG1 bacterial construct expressing aidH lactonase gene demonstrated the ability to quench both luminescence of wild-type *V. harveyi* 116 (FIG. 2A) and, even more prominently, luminescence of *V. harveyi* 117 mutant strain that respond to AI-1 only (FIG. 2B). However, no luminescence quenching was observed when the present inventors co-cultivated the genetically modified bacteria with a *V. harveyi* 118 strain that exclusively responds to AI-2 (FIG. 2C). Bacterial constructs expressing luciferase as neutral gene (pLuc) were used as control. Prominent luminescence-quenching effect of co-cultivation of *Vibrio* with AG1-pAidH demonstrates that the novel genetically engineered bacterial strains are efficient quorum quenchers as indicated by a reduction in bioluminescence.

Figure 3A:
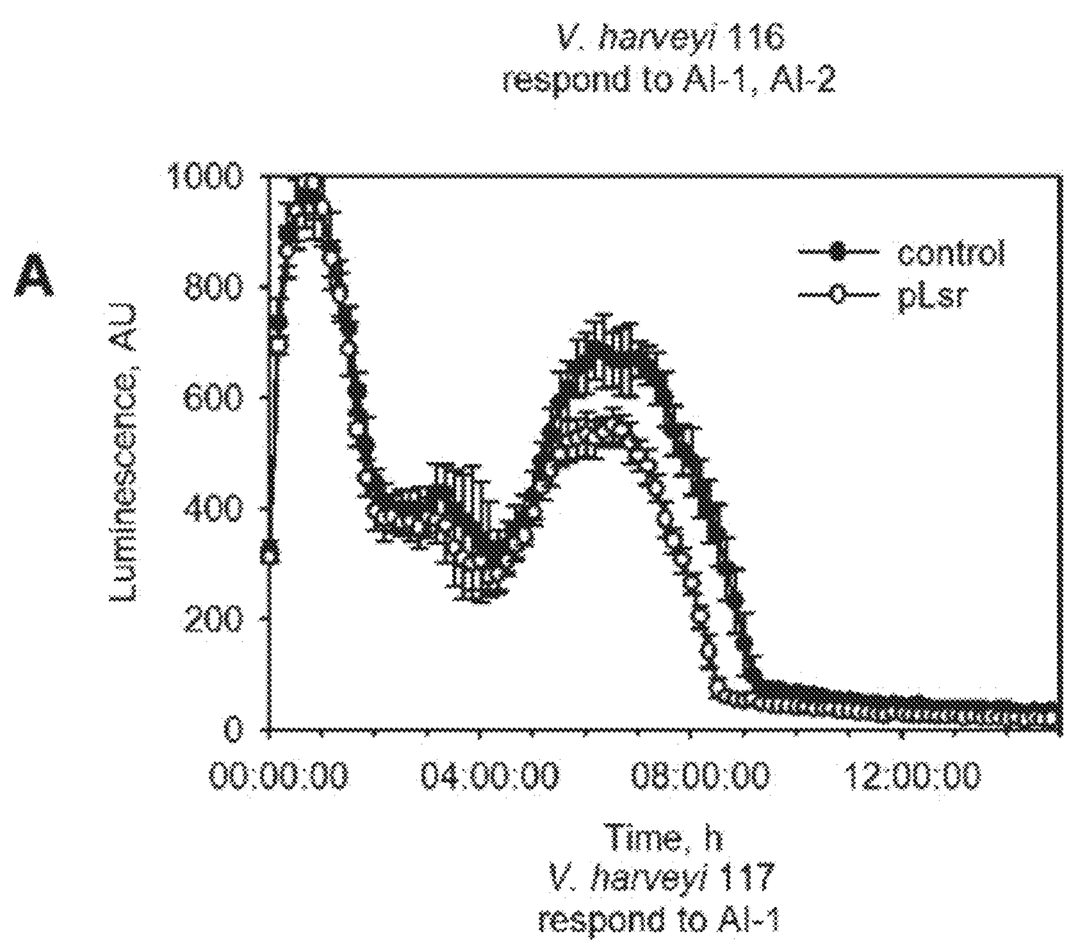
FIG. 3: Quorum quenching bacteria expressing lsr operon specifically decrease luminescence of *V. harveyi*. (A) Co-cultivation with Ag1-pLsr decrease luminescence of wt *V. harveyi* that responds to all autoinducers. (B) Co-cultivation with Ag1-pLsr weakly decreases luminescence of *V. harveyi* 117 that responds to AI-1 only. (C) Co-cultivation with Ag1-pAidH strongly decreases luminescence of *V. harveyi* 119 that does responds to AI-2 only.
Figure 3B:
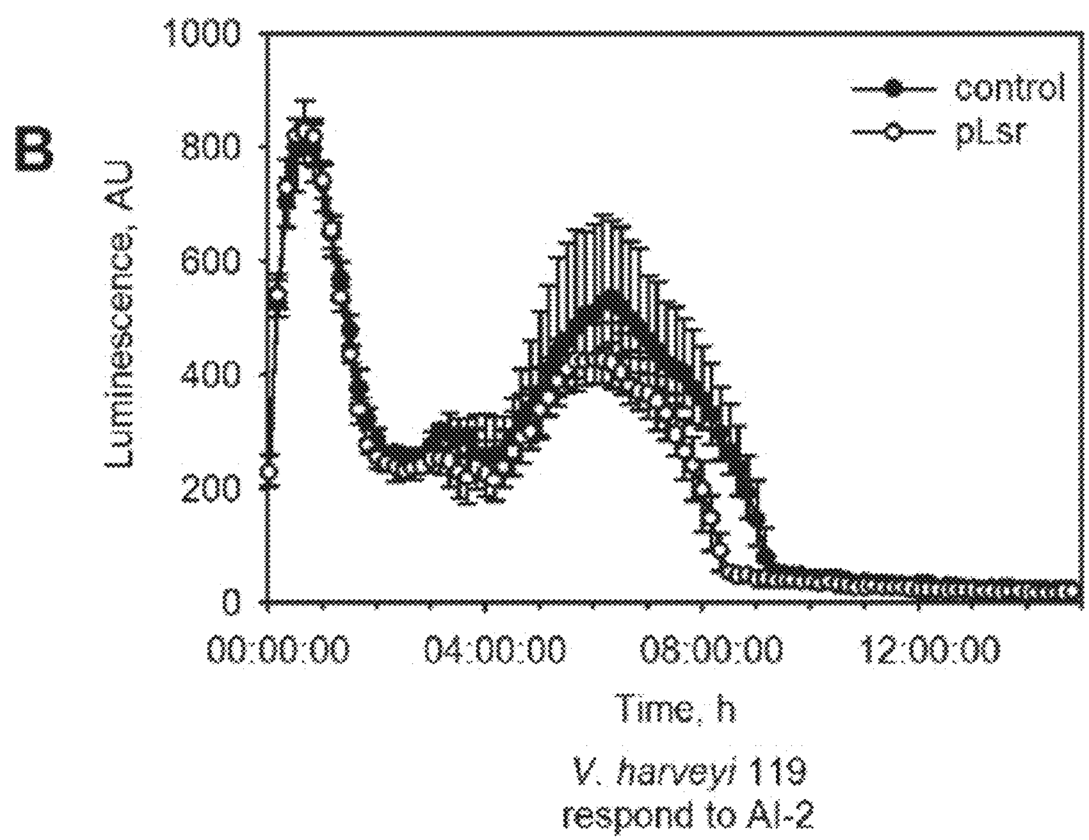
Figure 3C:
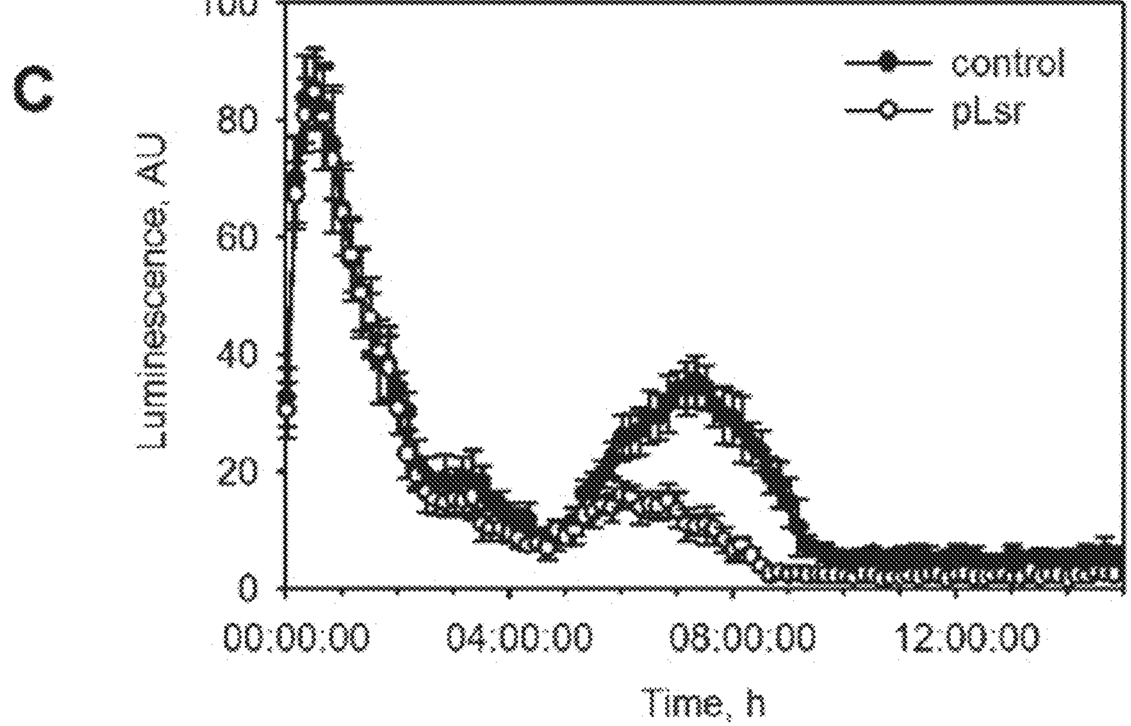

Example 3: Co-Cultivation of *Vibrio harveyi* with Lsr-Expressing AG1 Constructs Leads to Decrease in *Vibrio* Luminescence The present inventors next demonstrated that over-expressing lsr operon in Ag1 leads to quorum quenching. In this embodiment, the present inventors performed analogous experiments as generally described above utilizing an Ag1—pLsr construct. As control construct, Ag1-pOX strain bearing a plasmid without any insert was used. As generally shown in FIG. 3, AI-2, AG1-pLsr quenches wild-type *V. harveyi* 116 bioluminescence to a similar extent as Ag1-pAidH (FIG. 3A). However, there was negligible effect on bioluminescence from V. *harveyi* 117 (responsible to AI-1 only) (FIG. 3B). In contrast, bioluminescence of *Vibrio* strain 119, which only responds to AI-2, was noticeably quenched by co-cultivation with Ag1-pLsr (FIG. 3C). Thus, the present inventors confirmed that the novel genetically modified bacterial constructs reduced *Vibrio* quorum sensing both specifically and efficiently.

Figure 4:
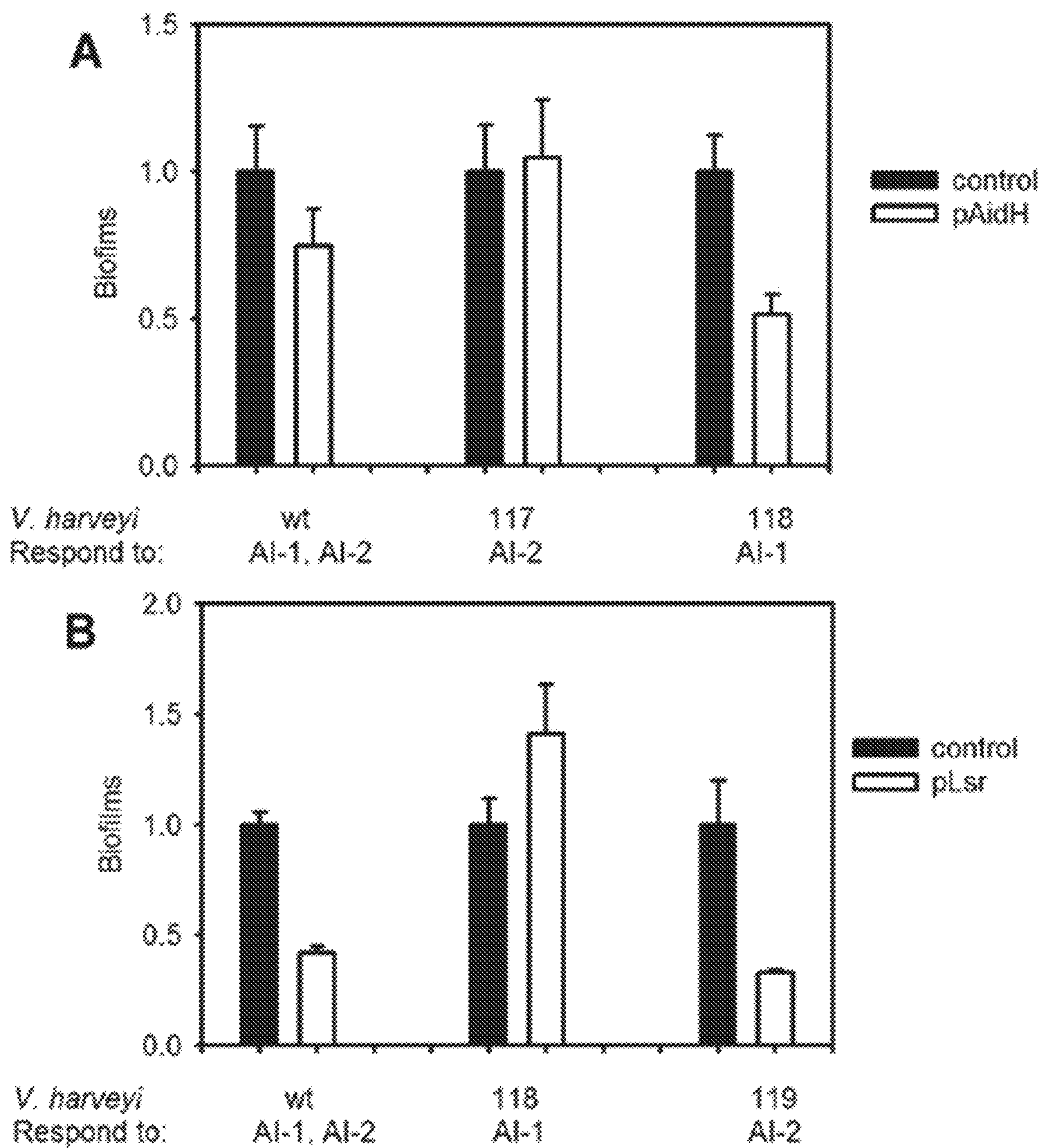
FIG. 4: Quorum quenching bacteria specifically decrease biofilm formation by V. *harveyi*. (A) Co-growth with AG1-pAidH decreases biofilm formation by only *V. harveyi* strains that are sensitive to corresponding lactone AI-1. (B) Co-growth with AG1-pLuc decreases biofilm formation by only *V. harveyi* strains that are sensitive to AI-2.

Example 4: Co-Cultivation of *Vibrio harveyi* with Quorum-Quenching Ag1 Constructs Leads to Reduced *Vibrio* Fitness and Reduced Biofilm Formation As outlined above, biofilm formation is an important pathogenic trait of many bacteria. In order to establish anti-pathogenic mechanisms of the designed quorum quenching constructs the present inventors studied their effect on biofilm formation by *V. harveyi*. As shown below, the present inventors demonstrated that AG1 alone produced almost no biofilms during while co-cultivation of AG1 with *V. harveyi* strains results in detectable biofilms layer. As generally shown FIG. 4A, elimination of AI-1 from bacterial media by AG1-pAidH leads to decreased biofilm formation by all *Vibrio* strains that respond to AI-1 (e.g. 116 and 118), but not by the mutant strain 117 that does not respond to AI-1. The present inventors further demonstrated that AG1-pLsr, which quenches AI-2 molecules, is able to decrease biofilm formation in all strains that are sensitive to AI-2 (e.g. wild-type 116 and its mutant variant 119). However, co-cultivation with AG1-pLsr has had no negative effect on biofilm formation by *V. harveyi* 118 that responds to AI-1 only. Thus, using the opportunistic pathogen *V. harveyi* as an exemplary model organism, the present inventors show that in certain embodiment, the novel's quorum-quenching constructs are able to decrease biofilm formation both efficiently and specifically. (FIG. 4)

Figure 5:
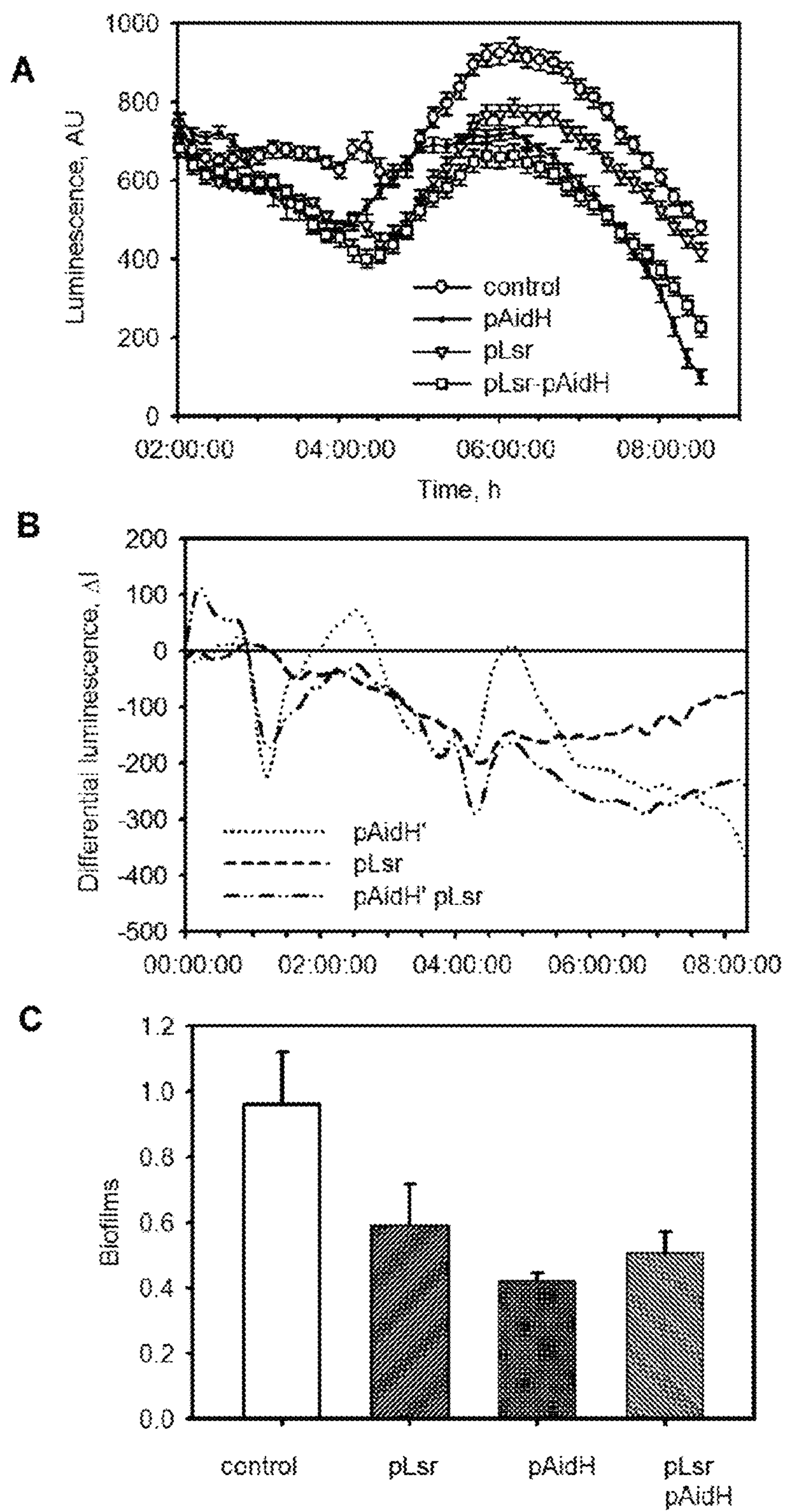
FIG. 5: Depletion of both AI-1 and AI-2 cumulatively decrease luminescence but not biofilm formation. (A) Effect of co-cultivation with Ag1-pAidH', Ag1-pLsr and Ag1-pAidH-pLsr on luminescence of wild-type *V. harveyi*. (B) Bioluminecence differential curves illustrate temporal differences in quorum quenching by Ag1-pAidH', Ag1-pLsr and double construct AG1-pAidH'pLsr. (C) Effect of co-cultivation with Ag1-pAidH', AG1-pLsr and AG1-pAidH'pLsr on biofilm formation wild-type *V. harveyi.*

Example 5: Co-Expression of aidH and Lsr in Ag1 Leads to Reduced *Vibrio* Luminescence but does not Decrease Biofilm Formation In one embodiment of the invention, the present inventors demonstrated that bacterial constructs expressing individual quorum quenching factors (e.g. lsr or aidH) exhibits similar but yet partial effects on both luminescence and biofilm formation. It was reasoned that co-expression of two quorum quenchers together may lead to an additive outcome. Thus, the present inventors cloned and expressed aidH gene under control of the same strong pupp promoter in compatible plasmid vector pACYC184 that may co-exist with pOX types of plasmids in bacterial cells. Both pLsr (pOX) and pAidH' (pLuc) plasmids were introduced into the AG1 cells. As generally shown in FIG. 5, while pACYC184-AidH has lower copy numbers compared with plasmid pAD-AidH, it produced sufficient AidH protein to quench *Vibrio* luminescence efficiently (FIG. 5 A, B) and to reduce biofilm formation (FIG. 5 C). While any effect of pLSR and pAidH' co-expression on biofilm formation was observed, a cumulative effect on *Vibrio* bioluminescence was demonstrated in the data. Importantly, co-expression of two quorum quenching constructs allows embodiments of the present invention to cover different bacteria population growth phases.

Example 6: Shrimp Feeding/*Vibrio parahaemolyticus* Challenge

To determine if disrupting quorum sensing in enteric bacteria provides protection to shrimp from pathogenic *Vibrio* sp., and if it reduces EMS-associated mortality, the present inventors performed shrimp EMS trials using *Vibrio parahaemolyticus* as an exemplary pathogen. In this embodiment, to establish a population of quorum quenching bacteria in shrimp intestines, shrimp were fed by *Enterobacter* expressing various plasmid encoded quorum quenching molecules or asRNA-dam for 5 days prior to *Vibrio* challenge.

To confirm that Ag1 bacteria are able to survive and persist in shrimp intestines, preliminary colonization experiments were conducted. Ag1 were transformed by plasmid pGFPuv (Clontech) encoding the fluorescent GFP protein. Shrimp were fed by food with Ag1-pGFPuv for 10 days and presence of Ag1 was detected at days 5 and 10 by analysis of shrimp intestines under fluorescent microscope (GFP fluorescence detected in the intestines) and by a plate counting method (Ag1 colonies were identified by GFP fluorescence) using isolated guts of shrimp. After days of Ag1 feeding the bacterial titer in the shrimp intestines was ~2.8E+06 cfu/g and it had slightly increased at day 10 (See Table 1 below). In this embodiment, day 5 after feeding the genetically modified bacteria to the shrimp the present inventors initiated *Vibrio* challenges.

Example 7: EMS-Induced Mortality Count

Figure 6:
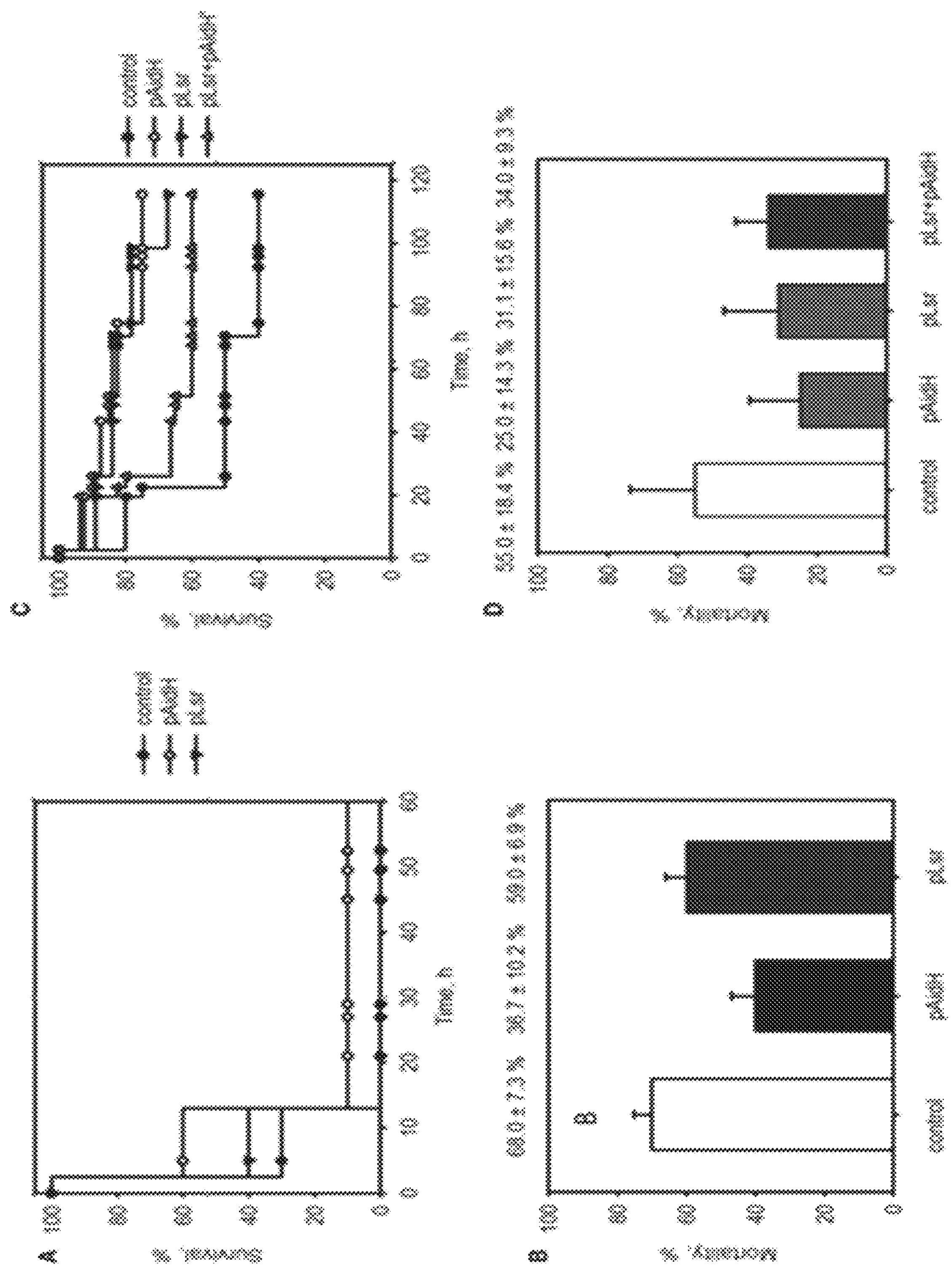
FIG. 6: Protective effect of quorum quenching *Enterobacter* strains for shrimp during *Vibrio* challenge. (A-B Trial 1), A, survival rate of shrimp fed Ag1-Luc, Ag1-pLsr and Ag1-pAidH bacteria. B, Total mortality count at 12 h post infection. (C-D Trial) C, survival rate of shrimp fed Ag1-Luc, Ag1-pLsr, Ag1-pAidH and Ag1-pLsr-AidHbacteria. D, Total mortality count at 120 h post infection.

In this example, two independent EMS-challenge trials were performed. As generally shown in FIG. 6, in trial 1 *Vibrio* infection appeared to be acute and yielded fast mortality in all tested groups; 100% of shrimp from control group died within 12-24 h after *Vibrio* challenge. However, development of infection was delayed in shrimp fed Ag-AidH1p bacteria (37% mortality within 12 h post-infection vs 68% mortality in control group), and 20% of the Ag-AidH1p group survived the 5 day experiment, while no shrimp from the control group survived. (FIG. 6A-B)

Conditions of infection were optimized for second quorum quenching shrimp trial. The infection dose was 10× reduced, and additional washing steps were added to eliminate the accumulation of bacterial toxins in the *Vibrio* culture before challenge. In this trial the infection developed more slowly and total mortality at day 5 post infection reached 55% in the control group fed only Ag1-Luc. Under these conditions all quorum quenching strains provided shrimp some level of protection. For best performing group, Ag-AidH1p, total mortality after 5 days post infection was 25% vs 55% for the control group. Shrimp fed Ag-1pLsr and Ag-AidH1p-lsr had mortality rates of 31% and 34% respectively. (FIG. 6 C-D)

Example 8: Reduction of Expression Virulence Genes in *Vibrio* from Intestines of Shrimp Fed *Enterobacter* Quorum Quenching Strains Ag1-pAidH, Ag1-pLsr and Ag1-pL1sr-pAidH As generally outline above, for many pathogenic bacteria quorum sensing is an important part of virulence regulation, and is involved in regulation of the expression of virulence genes. As such, the present inventors selected two separate *Vibrio parahaemolyticus* virulence factors, namely Mam7 and PirA, as markers for the pathogenicity state of *Vibrio* in this preferred embodiment. Mam7 is an adhesion protein which binds to fibronectin and is critical for initial attachment of *Vibrio* to host cells during early stage of infection. PirA is cytotoxic protein involved in EMS development.

Figure 7:
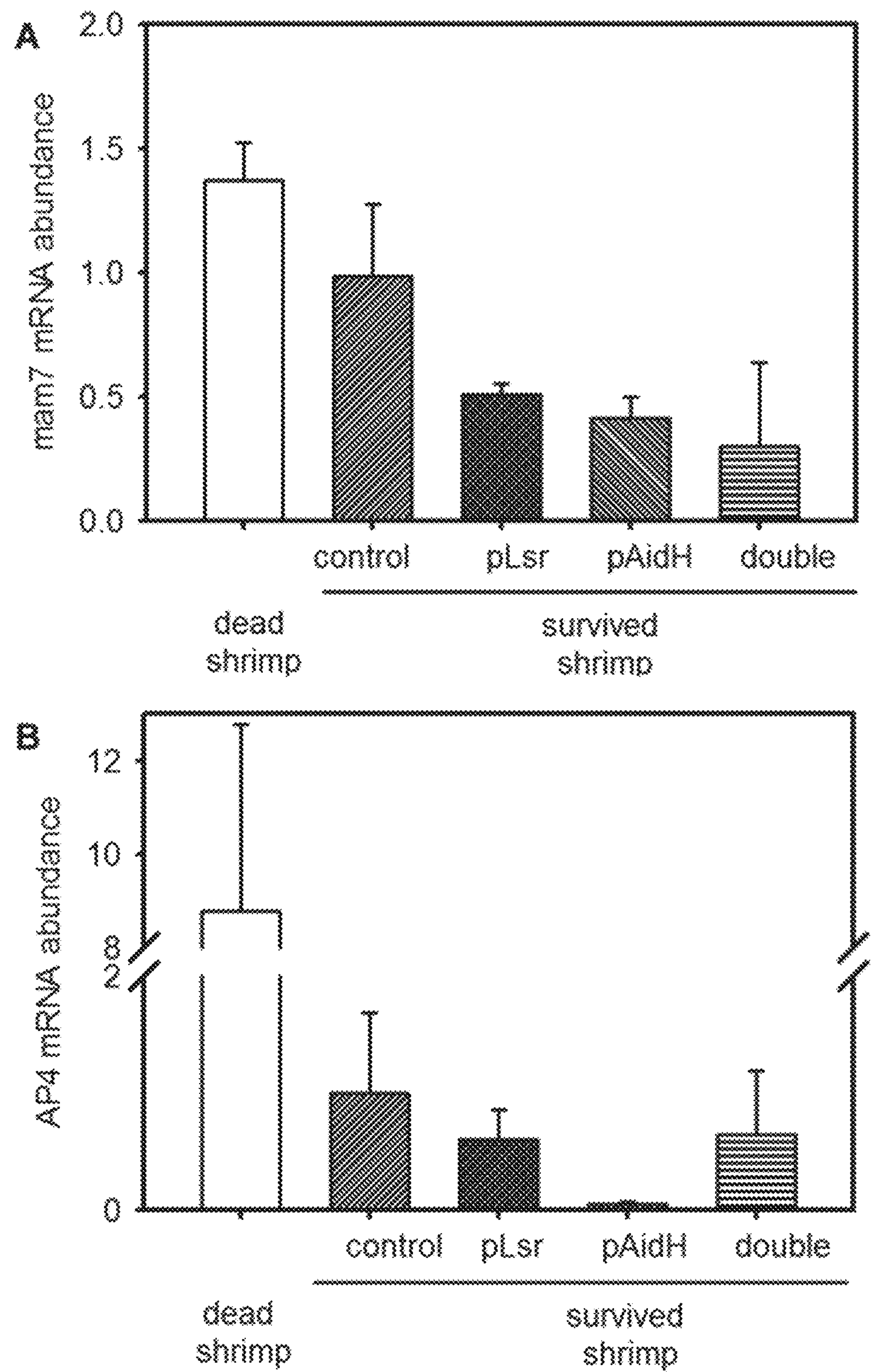
FIG. 7: Virulence gene expression in *Vibrio parahaemolyticus* from intestines of shrimp fed *Enterobacter* quorum quenching strains. (A) Mam7 expression level; and (B) Pir-like toxin expression level.

As generally shown in FIG. 7, alive and dead shrimp were collected in Trial 2 at 48 h after infection, and levels of Mam7 and Ap4 expression were assessed by qPCR on mRNA extracted from shrimp intestines. Expression of Mam7 was about 2-fold reduced in *Vibrio* from intestines of shrimp fed all quorum quenching *Enterobacter* strains. Mam7 expression levels in *Vibrio* from intestines of dead shrimp was approximately the same as in alive shrimp from control group indicating the mRNA was not degraded in dead shrimp. (See FIG. 7A.) Expression of the toxin PirA mRNA was also reduced in *Vibrio* obtained from shrimp fed all quorum quenching bacterial strains, with the highest reduction observed in shrimp fed Ag1-pAidH bacteria. Noticeable, this shrimp group had superior survival rates compared to all other groups. The level of pirA expression in *Vibrio* from intestines of dead shrimp was almost 10-fold elevated compared to all surviving shrimp (See FIG. 7B).

Example 9: Preventing EMS by Inoculating Shrimp with Enteric Shrimp Bacteria Expressing asRNA Targeting *Vibrio* Genes As described above, in one embodiment, the invite technology includes novel methods, systems and compositions for the regulation of the expression of target genes in bacteria by asRNA produced in another bacterium which targets a gene of interest expressed by the recipient bacteria. For example, in one embodiment, the invention may include reduction in dam expression in *Vibrio* co-cultivated with *Enterobacter* Ag1 expressing asRNA-dam. In *Vibrio*, dam-dependent DNA methylation is involved in regulation of pathogenicity pathways; therefore reduction in level of dam expression should lead to decreased *Vibrio* virulence. In one potential embodiment of this asRNA strategy, shrimp were fed by Ag1 expressing asRNA-dam and then challenged by *Vibrio parahaemolyticus.*

Example 10: EMS-Induced Mortality Count

Figure 8:
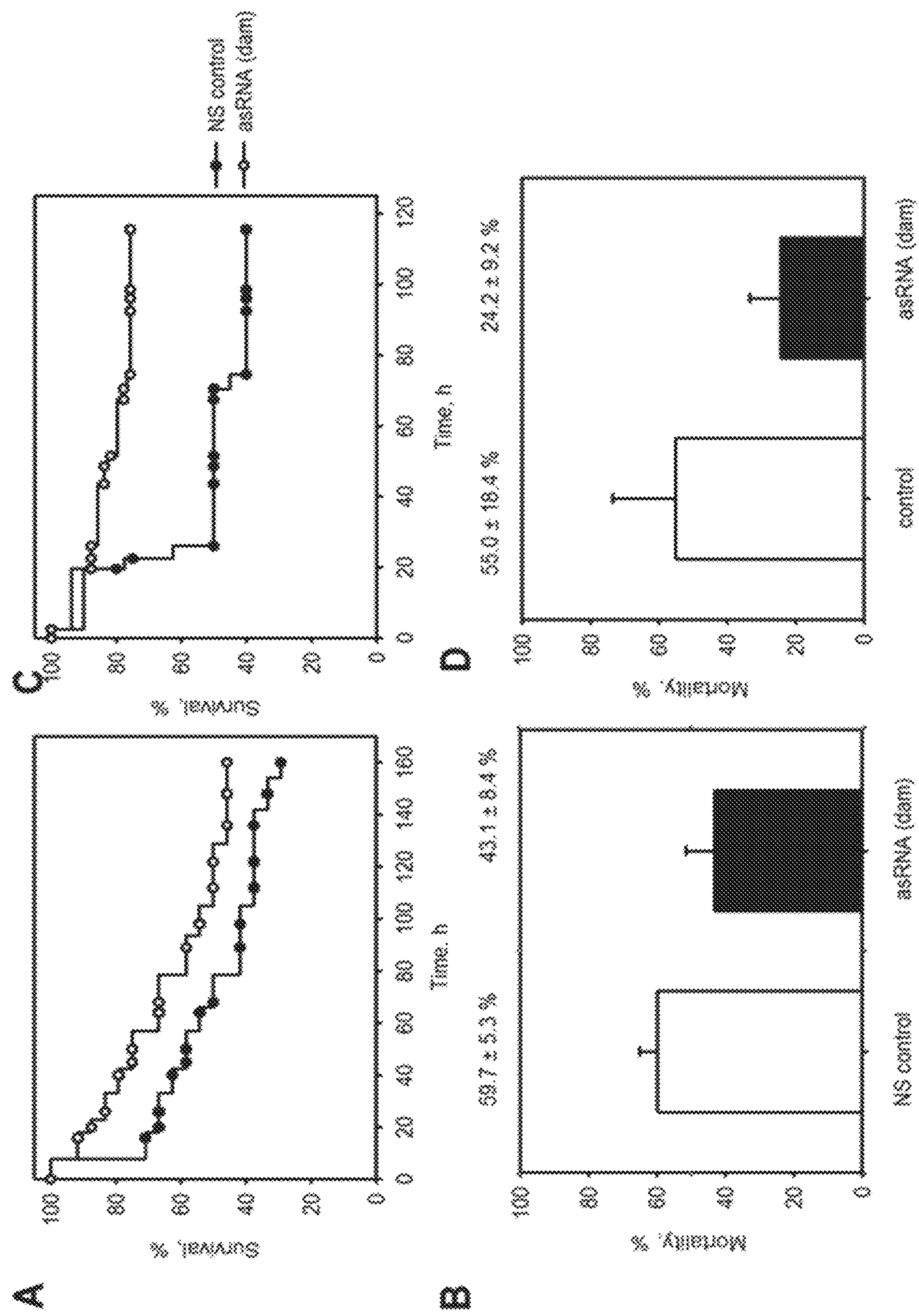
FIG. 8: Protective effect of *Enterobacter* expressing asRNA-dam for shrimp during *Vibrio* challenge. A-B Trial 1, A, survival rate of shrimp fed by Ag1-Luc (control) or by Ag1-asRNA-dam. B, Total mortality count at 5 days post infection. C-D Trial 2. C, survival rate of shrimp fed by Ag1-Luc (control) or by Ag1-asRNA-dam. B, Total mortality count at 5 days post infection.

In this example, two independent challenge trials were performed. As generally shown in FIG. 8, in both trials shrimp fed *Enterobacter* expressing asRNA-dam (Ag1-asRNA-dam) had reduced mortality compare to control group. In one challenge trial shown in FIG. 8A-B, shrimp were fed Ag1 configured to express an unspecific protein (Ag1-Luc) as a control. In this example, the reduction in mortality effect was moderate, with 43% of mortality in shrimp fed by Ag1-asRNA-dam vs 59% mortality in control group. (See FIG. 8) In a second trial shown in FIG. 8 C-D, the mortality rate for shrimp fed Ag1-asRNA-dam was reduced more than 2-fold compared to shrimp fed by Ag1-Luc. Mortality at day 5 post infection was 24% vs 55% for the control group. (FIG. 8 C-D) The differences in results between the first and second trial could be explained by the fact that in second trial culture of *Vibrio* cultures was rinsed 3× before adding the bacteria to the shrimp food, which potentially reduce accumulation of bacterial toxins in the food.

Figure 9:
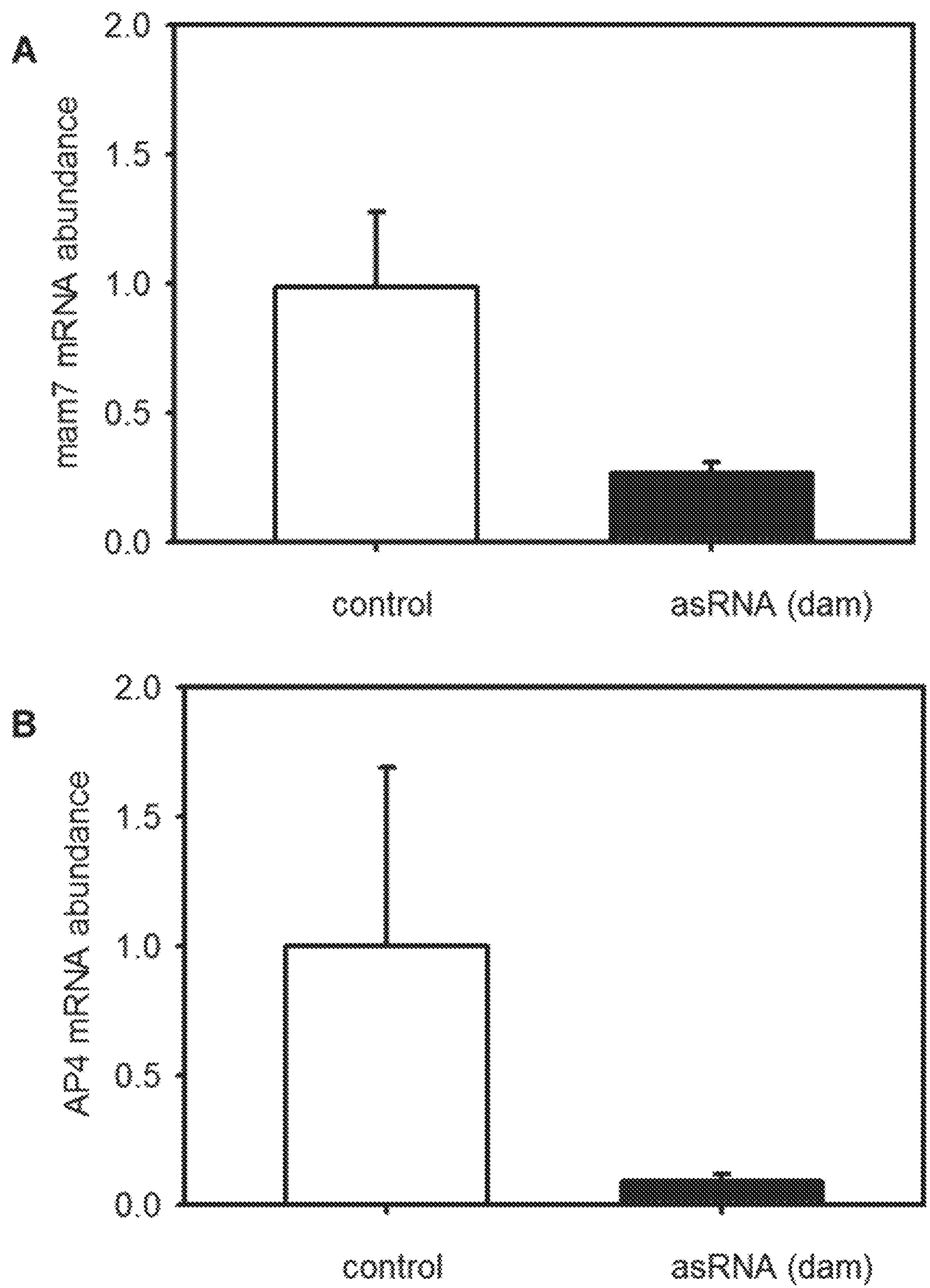
FIG. 9: Virulence gene expression in *Vibrio parahaemolyticus* from intestines of shrimp fed by *Enterobacter* expressing asRNA-dam. (A) Mam7 expression level; (B) Pir-like toxin expression level.

Example 11: Reduction of Expression of Virulence Genes in *Vibrio* Obtained from Shrimp Fed *Enterobacter* Expressing asRNA Targeting the Expression of the *Vibrio* Dam Gene In this example, the expression levels of *Vibrio parahaemoliticus* virulence genes mam7 and pirA were assessed by qPCR on RNA extracted from intestines of dead and alive shrimp collected in Trial 2 at 48 h after *Vibrio* challenge. Expression of both virulence genes was dramatically reduced in *Vibrio* obtained from intestines of shrimp fed Ag1-asRNA-dam. The mam7 gene expression was reduced 3.5 fold, and pirA expression was reduced ~10 times in this group. (FIG. 9)

Example 12: Mam7 Expression May be Regulated by Dam-Dependent DNA Methylation

Figure 10:
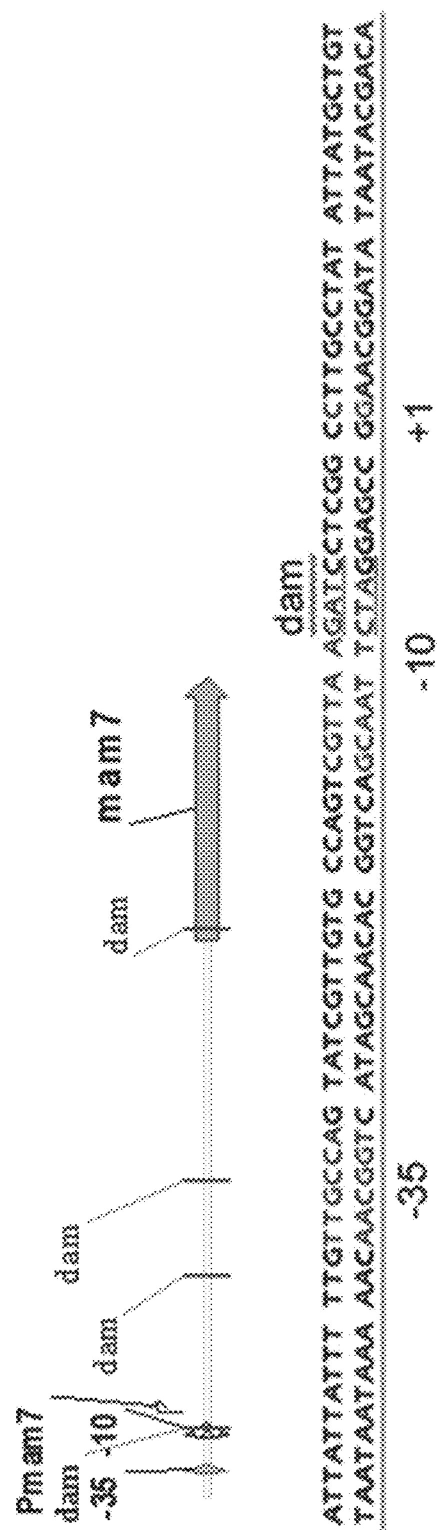
FIG. 10: Hypothetical mam7 promoter position and location of Dam target sequences in upstream of mam7 gene in *Vibrio* parahaemohticus.

Significantly, qPCR analysis indicated reduction in mam7 expression in *Vibrio* in shrimp fed Ag1-asRNA-dam, indicating that mam7 expression may be regulated by Dam-dependent DNA methylation. The Mam7 gene regulation, including promoter and/or other cis/trans acting regulator elements has not been previously identified. To check possibility of Dam-dependent regulation of mam7 expression, the present inventors analyzed upstream of mam7 gene (VP1611) with Softberry software (http://www.softberry.com/) to predict the position and composition of mam7 promoter. As shown in FIG. 10, a potential gene promoter was found at position 288 bp upstream of the mam7 start codon. Four potential Dam DNA methylase methylation target sequence (GATC) were found in the promoter area with one of them overlapping the −10 promoter element. This predicted promoter composition strongly suggests Dam-dependent regulation of mam7 gene expression.

Example 13: Using Enteric Shrimp Bacteria Engineered to Express Quorum Sensing Disrupting Molecules or asRNAs Targeting the Silencing of Essential/and or Virulence Genes in *Vibrio*

The present inventors describe herein systems, methods and compositions for the use of genetically engineered bacteria, more specifically enteric shrimp bacteria engineered to express quorum sensing disrupting molecules and/or asRNAs targeting the silencing of essential/and or virulence genes to protect shrimp from the development of *Vibrio* infection and reduce EMS-associated mortality. It was further demonstrates that *Vibrio* from intestines of shrimp fed quorum quenching bacteria and/or asRNA-dam-expressing bacteria had reduced expression of the virulence genes mam7 and pirA. Taken together these results demonstrate certain embodiments of the current inventive technology that use engineered enteric bacteria as an effective platform for protection of shrimp from pathogen infection.

Example 14: Material and Methods

Strains and Plasmids Design and Construction

All the strains and plasmids used in this invention are listed in Table 2. To create bioactive strains, plasmids described below were transformed into electro-competent *Enterobacter* cells. The plasmid descriptions are as follows: (a) pAidH—aidH gene of Ochrobactrum sp. (Mei et al., 2010) was codon-optimized to *Enterobacter* expression using the Vector NT program suit. The codon optimized gene was supplemented with ribosome-binding-site and was ordered as DNA fragment via IDTDNA. Add-on PCR was performed using the oligonucleotides pAD-lact-for and pAD-lact-rev (Table 3). For cloning, NEBuilder® HiFi DNA Assembly kit (NEB) was used to assembly the amplified gene sequences and the linearized pAD43 plasmid (FIG. 10A); (b) pLuc—was used as a control plasmid encoding the neutral gene. It was made as described above, but the luciferase gene was used instead aidH; (c) pAidH', pLuc'. Vector pACYC184 was used to create aidH (Luc)-expressing pAD/pSF compatible vector. To amplify genes with corresponding the promoter, terminator and ribosome binding sites, add-on PCR was performed using pACYC-for and pACYC-rev oligonucleotides. Finally, the PCR product was cloned into EcoRV-linearized pACYC184 plasmid using NEBuilder® HiFi DNA Assembly kit (NEB). Plasmid map is shown on FIG. 10

Plasmids that made by GENESCRIPT: (a) pLsr—contains the *E. coli* lsr operon expressed under the control of the lacUV promoter in the multiple copy plasmid vector pSF-OXB19 (Sigma). Plasmid map is shown on FIG. 10; (b) p(asDam) and p(asGFP) A paired termini (PT) RNA-stabilizing design for producing anti-sense RNA (asRNA) was used for creating asRNA-expressing cassettes. 38 bp-long flanking inverted GC-reach fragments were added on both ends of the specific asRNA sequence forming a hairpin structure with the asRNA loop at the end. rrnB terminator (terminator from rrnB *E. coli* gene) was placed after a 207 bp long connector sequence at the end of asRNA-expressing cassette, and the cassette was cloned into pAD-43-25 plasmid under control of the Pupp promoter.

Bacterial Growth

LBS media was used for bacteria growth (10 g/L Bacto-Tryptone, 5 g/L yeast extract, 20 g/L NaCl, 50 mM Tris-HCl pH 7.5). When required, antibiotics were used at the following concentrations: carbenicillin 50 μg/ml, ampicillin 100 μg/ml, chloramphenicol 25 μg/ml.

Biofilm Assay

*Vibrio harveyi* strains and *Enterobacter* Ag1 strains were grown overnight in LBS medium, diluted to $OD_{600}$ 0.2-0.4 and mixed with *Vibrio* sp. in a ratio of *Vibrio*/Ag1 at 5/1. Then 150 μl the mixed culture was added into wells of a 96 well plate (3 independent experiments with 8 technical replicates in each experiment were analyzed for each treatment) and incubated without shaking on 28° C. for 24 h. After incubation, the bacterial biofilms were stained by crystal violet according to the protocol described by O'Toole (O'Toole, 2011) and absorbance was measured on Tecan plate reader at 550 nm.

Bioluminescence Assay

*Vibrio*-strains and *Enterobacter* Ag1 strains (quorum quenchers) were grown overnight in LBS medium, diluted to $OD_{600\ nm}$ of 0.1-0.2 and were mixed in a ratio of 1:1 in a black 96 well tissue culture plate with clear bottom. Plates were covered by air breathable transparent film. Mixed cultures were grown on 28° C. for 12 h in a Sinergy H4 plate reader with periodic aeration. Luminescence and $OD_{600\ nm}$ measurements were taken every 20 min. 8 parallel curves taken for each experimental condition; 2 independent experiments were performed; averaged curves are shown.

qRT-PCR

Relative gene expression in *Vibrio* cells was measured by quantitative real-time PCR (qRT-PCR). Total RNAs were isolated using an Omega E.Z.N.A Bacterial RNA kit. Real-time PCR amplification was performed by using a Mx3000P QPCR system (Agilent technologies). A Luna® Universal One-Step RT-qPCR Kit (NEB) was used to perform one step RT-PCR. Oligonucleotides concentration and cycling conditions used were according manufacturer recommendations. Genes and gene specific primers are listed in Tables 5 and 6 respectively. Less than 25 ng of total bacterial RNA was used in each reaction. Relative expression levels of the specific transcripts were calculated using the gyrB mRNA expression level as the internal reference for normalization.

Data Analyses

Averages and standard errors of the mean (SEM) were calculated from at least three independent experiments. All other data were analyzed by Anova test with SigmaPlot. Significance of differences between experimental groups was accepted at a P value of <0.05.

Shrimp *Vibrio* Challenge

Bacteria: *Enterobacter* sp. Ag1 was transformed with plasmids indicated in Table 2. Bacteria were grown overnight in LB with the corresponding antibiotic, and then centrifuged and mixed into commercial shrimp food (Zeigler PL 40) at a concentration of 1E+10 CFU/gm feed and refrigerated. Prepared feed was fed to one-two gram shrimp at 10% body weight, divided into three feedings per day.

Shrimp feeding: SPF shrimp (Shrimp Improvement System, Islamorada, FL) 1 g weight were maintained in 7 gallon aquariums (n=12). Shrimp were randomly assigned to treatments groups: shrimp fed with commercial food with Ag1-Luc (ns), shrimp fed commercial food with Ag1-pLsr; shrimp fed commercial food with Ag1-pAidH; shrimp fed commercial food with Ag1-pAidH and shrimp fed with commercial food with Ag1-pLsr-AidH. Bacteria were provided to shrimp for 5 days before *Vibrio* challenge and during the course of the challenge via feed.

EMS challenge: An EMS+*V. parahaemolyticus* isolate was cultured in Tryptic Soy Broth (TSB)+2% NaCl, grown overnight, centrifuged, rinsed 3 times and suspended in Tryptic Soy Broth (TSB). The suspension was brought up to a concentration of $10^{10}$ CFU/ml. One ml of the prepared suspension was mixed with one gram of shrimp feed (Zeigler PL 40) and allowed to soak into the feed 15 minutes. The shrimp were fed 5% of their body weight.

EMS-induced mortality count: Mortality count was performed at day 2-5 after the *Vibrio* challenge. 4-6 biological replicates (separate tanks) were analyzed for shrimp from all treatment groups.

TABLE 1

Fluorescence load in intestines of shrimp fed by GFP-expressing Ag1.

| Group | Fluorescent bacterial load, 5 days, cfu/g | Fluorescent bacterial load, 10 days, cfu/g |
|---|---|---|
| shrimp fed Ag1-GFP | 2.8E+06 | 7.7E+07 |
| shrimp fed commercial food | 0 | 0 |

TABLE 2

Bacterial strains and plasmids.

| Strains | Genotype | Origin |
|---|---|---|
| *Vibrio harveyi* 116 | WT | ATCC type strain BAA-1116, BB120 |
| *Vibrio harveyi* 117 | luxN::tn5Kan | ATCC BAA-1117, BB170 |
| *Vibrio harveyi* 118 | luxPQ::tn5Kan | ATCC BAA-1118, BB886 |
| *Vibrio harveyi* 119 | luxM::tn5Kan | ATCC BAA-1119, BB152 |
| *Vibrio parahaemoliticus* | pirA positive WT isolate from infected shrimp pond | HBOI, Florida |
| Ag1 | *Enterobacter* sp. | Obtained from NMSU, Xu lab, *Aedes gambiae* midgut isolate |
| Ag1-asDam | Ag1 (pAD Dam) $Ap^R$, asRNA to *Vibrio dam* under Pupp cloned into pAD43-25 | Plasmid made by GENESCRIPT transformed into Ag1 |
| Ag1-asGFP | Ag1 (pAD GFP) $Ap^R$, asRNA to gfp under Pupp cloned into pAD43-25 | Plasmid made by GENESCRIPT transformed into Ag1 |
| Ag1-pLsr | Ag1 transformed with pLsr | Ag1 transformed with pLsr. This invention |
| Ag1-pAidH | Ag1 (pAD pAidH) $Ap^R$ | This invention |
| Ag1-pAidH' | Ag1 (pACYC184 pAidH) $Cm^R$, | This invention |
| Ag1-pOX | Ag1 transformed with pSF-OXB19 | This invention |
| Ag1-pAidH' pLsr | Ag1 transformed with pAidH' and pLsr | This invention |
| | Ag1 transformed with pGFPuv | |
| Ag1-pGFPuv | | This invention |

| Plasmid | Description | Origin |
|---|---|---|
| pAD43-25 | Gram-positive-*E. coli* shuttle vector expressing gfp under Pupp, $Ap^R$ | (Dunn & Handelsman, 1999) |
| pSF-OXB19 | General cloning vector, $Ap^R$ | Sigma |
| pLsr | *E. coli* lsr operon expressed under medium strength bacterial promoter $Ap^R$ | This invention |
| pAidH | aidH lactonase under Pupp cloned into pAD43-25, $Ap^R$ | This invention |
| pAidH' | aidH lactonase under Pupp cloned into pACYC184, $Cm^R$ | This invention |
| pLuc | luciferase under Pupp cloned into pAD43-25, $Ap^R$ | This invention |
| pGFPuv | *E. coli* vector expressing gfpuv under lac promoter | Clontech |

TABLE 3

Oligonucleotides used for lactonase cloning.

| Oligo | Sequence |
|---|---|
| pAD lact-for | GGGAAAACTGTATGTATTTGATCCTGCTT ATCGATCTAGAGAAAGA |
| pAD lact-rev | CAAGTTAAGGGATGCAGTTTACACGAACG AAAATCGCCATTCGCC |
| pACYC-for | TGCCGGGCCTCTTGCGGGATGATTGAAGA AGACTGCCGAG |
| pACYC-rev | ATGCTGTCGGAATGGACGATATCCGCTTA CAGACAAGCTG |

TABLE 4

Oligonucleotides used in qPCR analysis.

| Name | Sequence |
|---|---|
| Vp-mam7-for | GCTTAGAAAGCATGAGCGCC |
| Vp-mam7-rev | TGCCACGGTACATGATTGGT |
| Vp-gyrB-for | CGAGCATGCGCTAAGTGTTG |
| Vp-gyrB-rev | TAACGCTGACGGCTTAGACC |
| Vp-Ap4-for | ATGAGTAACAATATAAAACATGAAAC |
| Vp-Ap4-rev | TTGAGAATACGGGACGTGGG |

TABLE 5

Genes used in qPCR analysis

| Gene | Chromosome location | Function | Ref |
|---|---|---|---|
| gyrB | 1: 11353-13770 | DNA gyrase subunit B | |
| mam7 | 1: 1708552-1711200 | Adhesin | (Krachler et al., 2011) |
| pirA | plasmid | Early mortality syndrome toxin | (Lee et al., 2015) |

REFERENCES

The following references are hereby incorporated in their entirety by reference:

[1] Dunn, A. K. & J. Handelsman, (1999) A vector for promoter trapping in *Bacillus cereus*. *Gene* 226: 297-305.

[2] Krachler, A. M., H. Ham & K. Orth, (2011) Outer membrane adhesion factor multivalent adhesion molecule 7 initiates host cell binding during infection by gram-negative pathogens. *Proc Natl Acad Sci USA* 108: 11614-11619.

[3] Lee, C. T., I. T. Chen, Y. T. Yang, T. P. Ko, Y. T. Huang, J. Y. Huang, M. F. Huang, S. J. Lin, C. Y. Chen, S. S. Lin, D. V. Lightner, H. C. Wang, A. H. Wang, L. I. Hor & C. F. Lo, (2015) The opportunistic marine pathogen *Vibrio parahaemolyticus* becomes virulent by acquiring a plasmid that expresses a deadly toxin. *Proc Natl Acad Sci USA* 112: 10798-10803.

[4] Mei, G. Y., X. X. Yan, A. Turak, Z. Q. Luo & L. Q. Zhang, (2010) AidH, an alpha/beta-hydrolase fold family member from an Ochrobactrum sp. strain, is a novel N-acylhomoserine lactonase. *Applied and Environmental Microbiology* 76: 4933-4942.

[5] O'Toole, G. A., (2011) Microtiter dish biofilm formation assay. J Vis Exp.

[6] Ruwandeepika H. A., Karunasagar I., Bossier P., Defoirdt T. (2015). Expression and quorum sensing regulation of type III secretion system genes of *Vibrio harveyi* during infection of gnotobiotic brine shrimp. PLoS One 10:e0143935. 10.1371/journal.pone.0143935.

[7] Soonthornchai W, Chaiyapechara S, Jarayabhand P, Soderhall K, Jiravanichpaisal P (2015) Interaction of *Vibrio* spp. with the Inner Surface of the Digestive Tract of *Penaeus monodon*. PLoS ONE 10(8): e0135783. doi: 10.1371/journal.pone.0135783.

[8] Thammasorn, T., Jitrakorn, S., Charoonnart, P. et al. Aquacult Int (2017) Probiotic bacteria (*Lactobacillus plantarum*) expressing specific double-stranded RNA and its potential for controlling shrimp viral and bacterial diseases. 25: 1679. https://doi.org/10.1007/s10499-017-0144-z.

[9] Defoirdt T, Boon N, Sorgeloos P, Verstraete W and Bossier P (2008) Quorum sensing and quorum quenching in *Vibrio harveyi*: lessons learned from in vivo work. *The ISME Journal* 2: 19-26.

[10] De Schryver P, Defoirdt T, Sorgeloos P (2014) Early Mortality Syndrome Outbreaks: A Microbial Management Issue in Shrimp Farming? *PLoS Pathog* 10(4): e1003919. doi:10.1371/journal.ppat.1003919.

[11] Nguyen D V, Christiaens O, Bossier P and Smagghe G (2016) RNA interference in shrimp and potential applications in aquaculture. *Reviews in Aquaculture* (2016) 0: 1-12. doi: 10.1111/raq.12187.

[12] Rajamani S, Teplitski M, Kumar A, Krediet C, Sayre RT and Bauer WD (2011) AHL lactonase (AiiA) inactivation of quorum sensing agonists produced by *Chlamydomonas reinhardtii* and characterization of aiiA transgenic algae. *J. Phycol.* 47:1219-1227.

[13] Rajamani S and Sayre RT (2017) FRET-based biosensors for the detection and quantification of AI-2 class quorum sensing compounds. In: Molecular Methods in Quorum Sensing. Eds. *Livia* Leoni and Giordano Rampioni. Springer.

[14] Taga M E, Semmelhack J L and Bassler B L (2001) The LuxS-dependent autoinducer AI-2 controls the expression of an ABC transporter that functions in AI-2 uptake in *Salmonella typhimurium. Molecular Microbiology* 42: 777-793.

[15] Soonthornchai W, Chaiyapechara S, Jarayabhand P, Soderhall K, Jiravanichpaisal P (2015) Interaction of *Vibrio* spp. with the Inner Surface of the Digestive Tract of *Penaeus monodon. PLoS ONE* 10(8): e0135783. doi: 10.1371/journal.pone.0135783.

[16] Kobayashi, M. & Brummett, R. 2014. Disease management in aquaculture. In: Forum for Agricultural Risk Management in Development.

Yadav, M. K., Y. Y. Go, S. W. Chae & J. J. Song, (2015) The Small Molecule DAM Inhibitor, Pyrimidinedione, Disrupts *Streptococcus pneumoniae* Biofilm Growth In Vitro. *PLoS One* 10: e0139238.

[17] Berenstein, D., K. Olesen, C. Speck & O. Skovgaard, (2002) Genetic organization of the *Vibrio harveyi* DnaA gene region and analysis of the function of the V. *harveyi* DnaA protein in *Escherichia coli. J Bacteriol* 184: 2533-2538.

[18] Collier, J., H. H. McAdams & L. Shapiro, (2007) A DNA methylation ratchet governs progression through a bacterial cell cycle. *Proc Natl Acad Sci USA* 104: 17111-17116.

[19] Hoynes-O'Connor, A 3. asRNA-Dam alignment to dam mRNA. & T. S. Moon, (2016) Development of Design Rules for Reliable Antisense RNA Behavior in *E. coli. ACS Synth Blot* 5: 1441-1454.

[20] Julio, S. M., D. M. Heithoff, D. Provenzano, K. E. Klose, R. L. Sinsheimer, D. A. Low & M. J. Mahan, (2001) DNA Adenine Methylase Is Essential for Viability and Plays a Role in the Pathogenesis of *Yersinia pseudotuberculosis* and *Vibrio cholerae. Infection and immunity* 69: 7610-7615.

[21] Nakashima, N., T. Tamura & L. Good, (2006) Paired termini stabilize antisense RNAs and enhance conditional gene silencing in *Escherichia coli. Nucleic Acids Res* 34: e138.

[22] O'Toole, G. A., (2011) Microtiter dish biofilm formation assay. *J Vis Exp.*

[23] Val, M. E., S. P. Kennedy, A. J. Soler-Bistue, V. Barbe, C. Bouchier, M. Ducos-Galand, O.

[24] Skovgaard & D. Mazel, (2014) Fuse or die: how to survive the loss of Dam in *Vibrio cholerae. Mol Microbiol* 91: 665-678.

[25] Martinez Cruz, Patricia et al. "Use of Probiotics in Aquaculture." ISRN Microbiology 2012 (2012).

[26] Ma, D.; Hu, Y.; Wang, J.; Ye, S. & Li, A. (2006). Effects of antibacterial use in aquaculture on biogeochemical processes in marine sediment. The Science of the Total Environment, vol. 367, No. 1, pp. 273-277.

SEQUENCE LISTINGS
DNA
aidH (lactonase gene)
*Ochrobactrum*

SEQ ID NO. 1

```
ATGACAATTAATTATCATGAATTGGAAACCAGTCACGGTCGTATCGCAGT

CCGTGAGTCAGAAGGGGAAGGTGCGCCGCTGCTGATGATACATGGTAATA

GCAGTTCCGGGGCGATTTTTGCGCCACAGCTTGAGGGGGAAATAGGAAAG

AAATGGCGTGTCATTGCCCCAGATCTGCCGGGACATGGAAAGAGCACGGA

CGCAATCGACCCGGACCGCTCTTACAGCATGGAAGGCTACGCTGATGCCA

TGACAGAGGTTATGCAACAACTCGGTATTGCAGATGCGGTGGTATTCGGC

TGGAGCCTTGGAGGTCATATTGGCATAGAAATGATCGCGCGTTACCCAGA

AATGCGTGGTTTAATGATTACGGGCACCCCTCCGGTTGCACGGGAAGAAG

TAGGACAAGGCTTTAAGAGTGGTCCAGATATGGCGCTTGCAGGTCAAGAA

ATTTTTTCAGAACGGGATGTTGAGTCTTACGCTCGGAGTACGTGCGGAGA

ACCTTTTGAAGCTAGTCTTTTGGACATCGTAGCACGGACTGACGGGCGGG

CTAGACGCATTATGTTCGAAAAATTTGGGAGTGGAACTGGCGGTAACCAA

CGGGACATCGTTGCTGAAGCACAATTACCTATTGCCGTAGTGAATGGGCG

GGATGAACCATTTGTCGAGTTGGACTTCGTTAGCAAAGTTAAATTTGGAA

ACCTCTGGGAAGGTAAAACTCATGTAATCGACAATGCGGGACATGCTCCT

TTCCGGGAAGCTCCAGCTGAGTTCGATGCATATCTCGCCCGCTTCATACG

TGATTGTACGCAGTAA
```

DNA
lsr operon
*E. coli*

SEQ ID NO. 2

```
ATGCAAACGAGTGATACCCGCGCGTTACCGCTACTTTGCGCCCGCTCGGT

TTATAAACAGTATTCAGGGGTCAATGTCCTGAAAGGCATCGATTTTACGT
```

-continued

```
TGCATCAGGGGGAGGTCCACGCCCTGCTCGGCGGCAATGGTGCCGGTAAA

TCGACGTTAATGAAGATTATTGCCGGTATTACCCCTGCTGATAGCGGTAC

GCTGGAGATTGAGGGCAACAACTACGTCAGATTAACGCCAGTTCATGCTC

ATCAGCTGGGTATTTATCTCGTTCCCCAGGAACCGCTGCTTTTCCCAAGC

CTGTCGATAAAAGAAAACATCCTGTTTGGGCTGGCAAAAAAACAGCTCTC

CATGCAGAAAATGAAGAACTTGCTGGCGGCGCTGGGCTGCCAGTTTGATC

TGCATAGTCTGGCAGGATCGCTGGATGTCGCCGATCGCCAAATGGTGGAA

ATCCTCCGCGGGCTGATGCGCGACTCGCGGATTCTGATCCTCGATGAACC

TACCGCCTCGCTTACCCCTGCGGAAACCGAACGCTTGTTTAGTCGCTTGC

AAGAGCTGCTTGCTACTGGCGTGGGTATTGTTTTTATCTCGCATAAGCTG

CCGGAAATTCGCCAGATTGCCGATCGAATTAGCGTGATGCGCGACGGAAC

CATCGCCTTAAGCGGCAAAACCAGCGAACTGTCTACCGACGACATTATTC

AGGCCATCACCCCAGCGGTACGGGAAAAATCGCTCTCTGCCAGCCAAAAA

TTATGGCTGGAGTTACCTGGTAACCGCCCACAACATGCCGCCGGAACGCC

GGTGCTGACACTGGAAAATCTGACCGGCGAAGGTTTCAGGAATGTCAGCC

TGACGCTCAATGCCGGAGAAATTCTGGGCCTGGCTGGGCTGGTGGGGGCC

GGACGCACAGAACTGGCCGAGACGCTCTATGGTCTGCGTACTTTGCGTGG

CGGACGCATTATGCTGAATGGTAAAGAGATCAATAAATTATCCACTGGAG

AACGTTTACTGCGCGGTCTGGTTTATCTGCCGGAAGATCGCCAGTCATCC

GGACTGAATCTCGATGCTTCGCTGGCCTGGAACGTCTGCGCCCTTACTCA

TAACCTTCGTGGATTCTGGGCGAAAACCGCGAAAGATAATGCCACCCTGG

AACGTTATCGTCGGGCGCTGAATATTAAATTCAACCAACCGGAACAAGCT

GCACGGACATTATCCGGTGGCAACCAGCAAAAAATCCTCATTGCCAAATG

CTTGGAAGCTTCGCCGCAAGTATTGATTGTCGATGAGCCGACGCGCGGCG

TGGATGTCTCGGCCCGTAATGATATCTACCAGCTGTTGCGCAGCATCGCC

GCACAAAATGTGGCTGTGCTGCTTATCTCCTCCGACCTGGAAGAGATCGA

ACTGATGGCAGATCGTGTGTATGTGATGCATCAGGGCGAAATTACCCACT

CTGCACTGACCGAGCGCGATATTAATGTCGAGACTATTATGCGCGTTGCC

TTCGGCGATAGTCAGCGTCAGGAGGCGTCATGCTGAAGTTTATTCAGAAC

AACCGTGAAATCACGGCACTGCTGGCGGTGGTGCTGCTGTTTGTATTACC

CGGTTTTCTCGACCGCCAGTATTTAAGTGTGCAAACGCTGACCATGGTTT

ATAGCAGCGCGCAAATCCTGATCCTGCTGGCAATGGGCGCGACGCTGGTA

ATGCTTACGCGCAATATTGATGTTTCAGTGGGTTCGATTACCGGAATGTG

CGCGGTGCTGTTGGGGATGTTACTGAACGCAGGATATTCACTACCTGTTG

CTTGTGTCGCGACTTTACTGCTTGGTTTGCTCGCGGGATTTTTCAACGGT

GTCCTGGTCGCGTGGCTAAAGATCCCTGCCATTGTTGCCACCCTTGGCAC

GTTAGGGTTGTACAGAGGCATCATGTTGCTGTGGACTGGCGGCAAATGGA

TTGAAGGGTTACCCGCCGAACTGAAACAGCTCTCCGCCCCGCTGCTGCTT

GGCGTTTCAGCAATTGGTTGGTTGACGATAATTCTGGTGGCATTTATGGC

CTGGCTGCTGGCAAAGACGGCGTTTGGACGCAGTTTTTATGCCACGGGCG
```

-continued

```
ATAATTTACAGGGCGCTCGTCAACTGGGCGTTCGTACTGAAGCCATTCGC
ATTGTGGCATTTTCGTTGAACGGCTGCATGGCGGCACTGGCGGGAATTGT
GTTTGCTTCGCAGATTGGTTTTATCCCCAACCAGACCGGTACCGGGCTGG
AGATGAAAGCAATTGCAGCCTGCGTGCTGGGCGGCATTAGTTTGCTCGGT
GGTTCCGGTGCGATCATTGGTGCGGTACTCGGCGCATGGTTCCTGACGCA
GATCGATAGCGTACTGGTGCTGTTGCGCATTCCGGCATGGTGGAATGATT
TTATCGCGGGTCTGGTTCTGCTGGCGGTGCTGGTGTTTGATGGACGCCTG
CGTTGTGCGCTGGAACGTAATCTACGGCGGCAAAAATATGCCCGCTTTAT
GACGCCACCGCCATCCGTTAAACCCGCTTCGTCAGGTAAAAAACGGGAGG
CCGCATAATGCGTATTCGCTACGGTTGGGAACTGGCTCTTGCCGCACTGC
TCGTTATTGAGATTGTCGCATTTGGTGCAATTAACCCGCGAATGTTAGAT
CTCAATATGTTGCTGTTCAGCACCAGTGACTTTATCTGCATTGGCATTGT
CGCCCTACCGCTAACGATGGTGATTGTCAGTGGCGGGATCGATATTTCGT
TTGGTTCGACCATCGGCCTCTGCGCCATTGCATTGGGCGTACTGTTTCAA
AGTGGTGTGCCGATGCCGCTGGCGATACTCCTGACCTTACTGCTCGGCGC
ATTGTGCGGGCTGATCAACGCCGGATTAATTATCTATACCAAAGTTAACC
CGCTGGTGATTACGCTTGGCACGCTGTATCTGTTTGCCGGAAGCGCTCTG
CTGCTTTCCGGTATGGCCGGAGCGACGGGGTACGAAGGTATTGGTGGATT
CCCGATGGCGTTTACAGATTTCGCTAACCTGGATGTGCTGGGACTCCCCG
TTCCGCTGATTATCTTCCTGATATGTCTCCTCGTTTTCTGGCTCTGGCTG
CATAAAACCCATGCCGGACGTAATGTGTTTTTGATTGGGCAAAGCCCGCG
CGTGGCGCTTTATAGCGCGATTCCAGTTAACCGTACCTTATGTGCGCTCT
ATGCCATGACGGGGCTGGCGTCTGCGGTCGCCGCTGTGCTGCTGGTATCG
TATTTTGGTTCAGCACGTTCCGATCTCGGTGCGTCGTTTCTGATGCCCGC
CATCACCGCCGTGGTGCTTGGCGGGGCCAATATTTATGGTGGTTCCGGTT
CCATTATCGGCACCGCCATTGCGGTTTTATTAGTGGGATATTTGCAACAA
GGTTTGCAAATGGCAGGAGTGCCAAATCAGGTGTCCAGCGCCCTTTCCGG
TGCGCTACTTATCGTCGTTGTCGTAGGTCGTTCCGTTAGCCTGCATCGCC
AGCAAATTAAAGAGTGGCTGGCGCGTCGGGCCAATAACCCATTGCCATAA
AGGATATCTTCATGACACTTCATCGCTTTAAGAAAATCGCCTTACTTAGC
GCTCTTGGCATTGCCGCAATCTCTATGAATGTGCAGGCCGCAGAGCGTAT
TGCATTTATTCCCAAACTGGTTGGCGTGGGATTTTTTACCAGCGGTGGCA
ACGGCGCACAACAAGCGGGTAAAGAGCTGGGCGTTGATGTGACCTACGAC
GGGCCGACAGAACCCAGTGTTTCTGGTCAGGTACAGTTGATTAATAACTT
CGTCAATCAAGGTTATAACGCCATTATCGTTTCTGCGGTTTCGCCTGATG
GCTTGTGTCCGGCACTGAAACGCGCCATGCAACGTGGTGTGAGAGTGCTG
ACCTGGGACTCTGATACTAAACCGGAGTGCCGCTCTTACTACATTAATCA
GGGAACGCCCGCCCAGTTAGGAGGTATGTTGGTGGATATGGCGGCGCGTC
AGGTGAATAAAGACAAAGCCAAAGTCGCGTTTTTCTACTCAAGCCCCACC
GTTACGGACCAAAACCAGTGGGTGAAAGAAGCGAAAGCGAAAATCGCCAA
AGAGCATCCAGGCTGGGAAATTGTCACTACGCAGTTTGGCTATAACGATG
```

-continued

```
CCACTAAATCGTTACAAACCGCAGAAGGAATATTAAAAGCGTATAGCGAT
CTCGACGCCATTATCGCCCCCGATGCCAACGCCCTGCCCGCTGCCGCACA
AGCCGCAGAAAACTTGAAAAATGACAAAGTAGCGATTGTCGGATTCAGTA
CGCCAAATGTGATGCGCCCGTATGTAGAGCGCGGCACGGTGAAAGAATTT
GGCCTGTGGGATGTGGTTCAGCAAGGCAAAATTTCAGTGTATGTCGCGGA
TGCATTATTGAAAAAAGGATCAATGAAAACGGGCGACAAGCTGGATATCA
AGGGCGTAGGTCAGGTTGAAGTCTCGCCAAACAGCGTTCAGGGCTATGAC
TACGAAGCGGATGGTAATGGCATCGTACTGTTACCGGAGCGCGTGATATT
CAACAAAGAGAATATCGGCAAATACGATTTCTGATGTGCATTACTTAACC
GGAGTAAGTTATGGCAGATTTAGACGATATTAAAGATGGTAAAGATTTTC
GTACCGATCAACCGCAAAAAAATATCCCTTTTACCCTGAAAGGTTGCGGT
GCGCTGGATTGGGGAATGCAGTCACGCTTATCGCGGATATTTAATCCGAA
AACGGGTAAAACCGTGATGCTGGCTTTTGACCATGGTTATTTTCAGGGAC
CGACTACCGGACTTGAACGCATTGATATAAATATCGCCCCGCTGTTTGAA
CATGCCGATGTATTAATGTGTACGCGCGGCATTTTGCGCAGCGTAGTTCC
CCCTGCGACCAATAGGCCGGTGGTACTGCGGGCGTCAGGTGCGAACTCTA
TTCTGGCGGAATTAAGTAATGAAGCCGTGGCGTTATCGATGGATGACGCC
GTGCGCCTGAACAGTTGCGCGGTGGCGGCGCAGGTTTATATCGGCAGCGA
ATATGAACATCAGTCGATCAAAAATATTATTCAGCTGGTTGATGCCGGAA
TGAAAGTGGGAATGCCGACCATGGCCGTGACTGGCGTGGGCAAAGATATG
GTGCGCGATCAGCGTTATTTCTCGCTCGCGACTCGAATCGCCGCTGAAAT
GGGGGCGCAAATTATCAAAACCTATTATGTCGAAAAAGGTTTTGAACGGA
TTGTTGCCGGATGTCCGGTACCCATTGTTATTGCTGGCGGTAAAAAATTA
CCGGAGCGCGAGGCGCTGGAAATGTGCTGGCAGGCTATCGATCAGGGCGC
TTCTGGTGTGGATATGGGGCGTAATATTTTCCAGTCTGACCATCCGGTGG
CGATGATGAAAGCCGTACAGGCGGTGGTTCACCATAACGAAACGGCTGAT
CGGGCATATGAACTCTATCTGAGTGAAAAACAGTAACTGCGGATCTAAGG
AGAAGAATTATGCACGTCACACTGGTTGAAATTAACGTTCATGAAGACAA
GGTTGACGAGTTTATCGAAGTTTTCGCCAGAACCACCTGGGCTCTGTAC
AGGAAGAAGGCAATTTGCGCTTCGATGTCTTACAGGACCCGGAAGTGAAT
TCGCGCTTTTATATCTACGAAGCCTATAAAGATGAAGACGCAGTGGCGTT
CCATAAAACCACGCCCCACTACAAAACCTGTGTCGCGAAACTGGAATCTT
TAATGACCGGGCCGCGTAAAAAACGTCTGTTCAATGGTTTGATGCCGTGA
ATCTACCTCGAGGTTTATGGCTCGACTCTTTACCCTTTCAGAATCAAAGT
ACTACCTGATGGCGCTGGATGCAGGCACCGGAAGTATTCGGGCTGTGATA
TTCGACCTGGAAGGCAATCAAATAGCAGTGGGACAGGCGGAGTGGCGGCA
TCTGGCAGTACCGGACGTTCCTGGTTCTATGGAATTTGATCTCAACAAAA
ACTGGCAACTGGCGTGTGAGTGTATGCGCCAGGCGCTGCACAACGCCGGC
ATAGCCCCGGAGTATATCGCTGCCGTTTCGGCATGTTCGATGCGTGAAGG
CATTGTTTTATATAATAATGAAGGAGCCCCGATCTGGGCCTGCGCCAATG
```

-continued

TGGATGCCAGAGCGGCACGCGAAGTTAGCGAACTTAAAGAACTGCACAAC

AATACCTTTGAAAACGAAGTTTATCGCGCGACCGGACAAACACTGGCTTT

AAGTGCCATCCCCAGATTACTTTGGCTGGCGCACCATCGTTCCGATATTT

ACCGTCAGGCATCAACCATCACCATGATCAGCGACTGGCTGGCCTATATG

CTCAGCGGCGAACTGGCGGTGGATCCCTCTAACGCTGGCACCACGGGACT

TCTTGATCTAACCACCCGTGACTGGAAACCTGCATTGCTGGATATGGCTG

GCCTACGTGCCGATATTCTTTCTCCTGTCAAAGAAACCGGCACATTGCTG

GGCGTGGTAAGTTCACAAGCGGCGGAACTCTGCGGTCTGAAGGCGGGCAC

TCCGGTGGTCGTTGGAGGAGGCGACGTGCAGCTTGGTTGCCTTGGGTTAG

GCGTTGTGCGTCCGGCACAAACCGCGGTTCTTGGCGGCACATTCTGGCAG

CAAGTTGTAAATTTAGCCGCGCCGGTGACAGACCCAGAAATGAACGTGCG

CGTTAATCCTCATGTTATTCCTGGCATGGTACAAGCTGAATCTATAAGCT

TTTTTACCGGACTCACCATGCGCTGGTTCCGCGATGCTTTCTGTGCCGAA

GAAAAACTGATTGCCGAACGTTTAGGCATCGACACCTATACGCTGCTGGA

AGAGATGGCCAGTCGGGTGCCGCCTGGGTCGTGGGGCGTAATGCCGATCT

TCTCCGACAGAATGCGCTTTAAAACCTGGTATCACGCTGCGCCTTCCTTT

ATTAACTTGTCCATTGACCCGGATAAATGTAACAAAGCGACATTGTTCCG

TGCGCTGGAAGAAAATGCGGCGATTGTATCAGCGTGTAACTTGCAGCAAA

TTGCTGATTTCTCGAATATTCATCCTTCATCGTTAGTCTTTGCAGGCGGA

GGTTCAAAAGGGAAATTATGGAGTCAAATTCTCGCTGATGTCTCGGGATT

ACCCGTCAATATTCCGGTGGTCAAAGAAGCCACTGCATTAGGATGTGCCA

TTGCAGCTGGCGTCGGTGCCGGAATTTTTTCATCAATGGCAGAAACCGGA

GAACGCCTGGTTCGCTGGGAACGGACGCACACACCAGACCCGGAAAAGCA

TGAACTTTATCAGGATTCACGCGATAAGTGGCAGGCAGTTTATCAGGATC

AGCTGGGGCTGGTTGATCATGGACTGACGACGTCGTTATGGAAAGCGCCT

GGGTTATAG asRNA
anti-sense RNA sequence targeting expression of dam gene in *Vibrio*

SEQ ID NO. 3

UAAUUCAACAAGAAUUGGGACAACUCCAGUGAAAAGUUCUUCUCCUUUAC

UCAU

DNA
dam gene
Vibrio sp.

SEQ ID NO. 4

ATGAAAAAGCAACGAGCCTTTCTTAAGTGGGCAGGAGGCAAATACGGTCT

GGTTGAAGACATCCAACGTCATTTACCACCGGCTCGAAAGCTAGTTGAAC

CCTTTGTTGGTGCTGGCTCGGTTTTTCTAAATACCGACTATGACCACTAT

CTACTGGCGGATATTAACCCCGACCTGATTAATCTCTATAACTTACTAAA

AGAGCGTCCTGAAGAGTACATCTCAGAAGCGAAGCGCTGGTTTGTTGCAG

AGAACAATCGCAAAGAAGCGTACTTGAATATTCGCGCCGAGTTTAATAAA

ACGGATGACGTGATGTACCGCTCGTTGGCGTTCCTATACATGAACCGCTT

TGGCTTTAATGGCTTATGTCGTTATAACAAAAAAGGCGGCTTTAATGTCC

CGTTTGGTTCTTACAAAAAGCCTTATTTCCCAGAAGCGGAGCTAGAATTC

-continued

TTTGCTGAAAAAGCCAAGAAAGCGACGTTCGTATGTGAAGGTTACCCAGA

AACGTTCAGTCGAGCGCGTAAAGGCAGCGTGGTTTATTGCGATCCACCGT

ACGCACCGTTGTCGAACACGGCGAACTTTACCTCTTATGCTGGCAACGGC

TTTACGCTGGATGATCAAGCTGCATTGGCTGATATTGCAGAGAAAGCCGC

AACTGAACGTGGTATCCCTGTTCTGATCTCAAACCATGACACGACATTAA

CGCGTCGCCTTTATCATGGTGCGGAGCTTAATGTCGTAAAAGTGAAGCGA

ACCATCAGTCGTAATGGCAGTGGTCGTAATAAAGTTGACGAGTTGCTGGC

GCTATTTCGTGCACCTGACGCGGACAAATCTGACTCTTAA

DNA
Artificial Sequence
pAD lact-for

SEQ ID NO. 5

GGGAAAACTGTATGTATTTGATCCTGCTTATCGATCTAGAGAAAGA

DNA
Artificial Sequence
pAD lact-rev

SEQ ID NO. 6

CAAGTTAAGGGATGCAGTTTACACGAACGAAAATCGCCATTCGCC

DNA
Artificial Sequence
pACYC-for

SEQ ID NO. 7

TGCCGGGCCTCTTGCGGGATGATTGAAGAAGACTGCCGAG

DNA
Artificial Sequence
pACYC-rev

SEQ ID NO. 8

ATGCTGTCGGAATGGACGATATCCGCTTACAGACAAGCTG

DNA
Artificial Sequence
Vp-mam7-for

SEQ ID NO. 9

GCTTAGAAAGCATGAGCGCC

DNA
Artificial Sequence
Vp-mam7-rev

SEQ ID NO. 10

TGCCACGGTACATGATTGGT

DNA
Artificial Sequence
Vp-gyrB-for

SEQ ID NO. 11

CGAGCATGCGCTAAGTGTTG

DNA
Artificial Sequence
Vp-gyrB-rev

SEQ ID NO. 12

TAACGCTGACGGCTTAGACC

DNA
Artificial Sequence
Vp-Ap4-for

SEQ ID NO. 13

ATGAGTAACAATATAAAACATGAAAC

DNA
Artificial Sequence
Vp-Ap4-rev

SEQ ID NO. 14

TTGAGAATACGGGACGTGGG

What is claimed is:

1. A compound for the biocontrol of pathogenic bacteria comprising:

a treated feed, a solid inoculum, or a liquid inoculum for a target host infected with or susceptible to a pathogenic bacteria, said treated feed, solid inoculum, or liquid inoculum comprising a genetically modified donor bacteria that may be introduced to a target host or said target host's environment, wherein said genetically modified donor bacteria is configured to express heterologous lsr operon or aidH and wherein:

said heterologous nucleic acid comprises a nucleotide sequence according to SEQ ID NO:1 or a sequence having approximately 75% or more homology with SEQ ID NO:1 which encodes for said heterologous aidH as a quorum quenching molecule configured to remove exogenous autoinducer-1 (AI-1) molecules from the environment; or said heterologous nucleic acid comprises a nucleotide sequence according to SEQ ID NO:2 or a sequence having approximately 75% or more homology with SEQ ID NO:2 which encodes for said heterologous lsr operon as a quorum quenching molecule configured to remove exogenous autoinducer-2 (AI-2) molecules from the environment resulting in the reduction or inhibition of quorum sensing (QS) in said pathogenic bacteria.

2. The compound of claim 1, wherein said target host comprises an aquatic organism.

3. The compound of claim 2, wherein said aquatic organism comprises a shrimp.

4. The compound of claim 3, wherein said target host's environment comprises an aquaculture environment.

5. The compound of claim 4, wherein said pathogenic bacteria comprises an Early Mortality Syndrome (EMS) causing pathogenic bacteria.

6. The compound of claim 5, wherein said Early Mortality Syndrome (EMS) causing pathogenic bacteria comprises a species of *Vibrio*.

7. The compound of claim 6, wherein said lsr operon is operably linked to a promotor that is configured to express at least one ATP-binding cassette transporter (ABC transporter) and at least one chaperone protein that actively pump exogenous autoinducer molecule AI-2 from the environment into said genetically modified bacterial cell.

8. The compound of claim 7, wherein said promotor comprises a constitutive or an inducible promotor.

9. The compound of claim 1, wherein said genetically modified bacteria comprises a genetically modified bacteria selected from the group consisting of: an enteric genetically modified donor bacteria, a symbiotic genetically modified donor bacteria, a shrimp probiotic genetically modified donor bacteria, an shrimp symbiotic genetically modified donor bacteria, an shrimp endosymbiotic genetically modified donor bacteria, an shrimp enteric genetically modified donor bacteria, Ag1, *Salmonella typhimurium, Bacillus subtilis, Enterobacter*, and *E. coli*, or other symbiotic bacteria.

10. The compound of claim 1, wherein said genetically modified bacteria configured to express said heterologous lsr operon may be transmitted through vertical or horizontal transfer.

11. The compound of claim 1, wherein said genetically modified bacteria configured to express a said heterologous lsr operon comprises a genetically modified bacteria configured to express a said heterologous lsr operon wherein said levels of exogenous AI-2 molecules in the environment are reduced to a level where biofilm formation or expression of pathogenesis genes, including those involved in toxin production by said pathogenic bacteria is reduced, or inhibited.

12. The compound of claim 1, wherein said genetically modified bacteria configured to express a said heterologous lsr operon comprises a genetically modified bacteria configured to express a said heterologous lsr operon wherein said levels of exogenous AI-2 molecules in the environment are reduced to a level where QS-mediated pathogenicity of said pathogenic bacteria is reduced, or inhibited.

13. The compound of claim 1 wherein said genetically modified bacteria configured to express a said heterologous lsr operon comprises a genetically modified bacteria configured to express a said heterologous lsr operon wherein said levels of exogenous AI-2 molecules in the environment are reduced to a level where EMS caused by *Vibrio* is treated or prevented.

14. The compound of claim 1 wherein said genetically modified bacteria configured to express a said heterologous lsr operon comprises a genetically modified bacteria configured to express said heterologous lsr operon wherein said levels of exogenous AI-2 molecules in the environment are reduced to a level where mortality of said target host due to EMS caused by one or more *Vibrio* is reduced.

15. A method of treating Early Mortality Syndrome (EMS) in an organism comprising introducing a compound according to claim 1 to a target host or said target host's environment that is infected by, or susceptible to infection by, an EMS-causing bacterial pathogen, wherein said target host is a shrimp, wherein said target host's environment comprises an aquaculture environment, and wherein said EMS-causing pathogen comprises a species of *Vibrio*.

* * * * *

SEQUENCE LISTING

<160> NUMBER OF SEQ ID NOS: 14

<210> SEQ ID NO 1
<211> LENGTH: 816
<212> TYPE: DNA
<213> ORGANISM: Ochrobactrum

<400> SEQUENCE: 1

```
atgacaatta attatcatga attggaaacc agtcacggtc gtatcgcagt ccgtgagtca     60

gaaggggaag gtgcgccgct gctgatgata catggtaata gcagttccgg ggcgattttt    120

gcgccacagc ttgaggggga aataggaaag aaatggcgtg tcattgcccc agatctgccg    180

ggacatggaa agagcacgga cgcaatcgac ccggaccgct cttacagcat ggaaggctac    240

gctgatgcca tgacagaggt tatgcaacaa ctcggtattg cagatgcggt ggtattcggc    300

tggagccttg gaggtcatat tggcatagaa atgatcgcgc gttacccaga aatgcgtggt    360

ttaatgatta cgggcacccc tccggttgca cgggaagaag taggacaagg ctttaagagt    420

ggtccagata tggcgcttgc aggtcaagaa atttttcag aacgggatgt tgagtcttac    480

gctcggagta cgtgcggaga acctttgaa gctagtcttt tggacatcgt agcacggact    540

gacgggcggg ctagacgcat tatgttcgaa aaatttggga gtggaactgg cggtaaccaa    600

cgggacatcg ttgctgaagc acaattacct attgccgtag tgaatgggcg ggatgaacca    660

tttgtcgagt tggacttcgt tagcaaagtt aaatttggaa acctctggga aggtaaaact    720

catgtaatcg acaatgcggg acatgctcct ttccgggaag ctccagctga gttcgatgca    780

tatctcgccc gcttcatacg tgattgtacg cagtaa                              816
```

<210> SEQ ID NO 2
<211> LENGTH: 7409
<212> TYPE: DNA
<213> ORGANISM: E. coli

<400> SEQUENCE: 2

```
atgcaaacga gtgataccg cgcgttaccg ctactttgcg cccgctcggt ttataaacag     60

tattcagggg tcaatgtcct gaaaggcatc gattttacgt tgcatcaggg ggaggtccac    120

gccctgctcg gcggcaatgg tgccggtaaa tcgacgttaa tgaagattat tgccggtatt    180

acccctgctg atagcggtac gctggagatt gagggcaaca actacgtcag attaacgcca    240

gttcatgctc atcagctggg tatttatctc gttccccagg aaccgctgct tttcccaagc    300

ctgtcgataa aagaaaacat cctgtttggg ctggcaaaaa aacagctctc catgcagaaa    360

atgaagaact tgctggcggc gctgggctgc cagtttgatc tgcatagtct ggcaggatcg    420

ctggatgtcg ccgatcgcca aatggtggaa atcctccgcg ggctgatgcg cgactcgcgg    480

attctgatcc tcgatgaacc taccgcctcg cttacccctg cggaaaccga acgcttgttt    540

agtcgcttgc aagagctgct tgctactggc gtgggtattg tttttatctc gcataagctg    600

ccggaaattc gccagattgc cgatcgaatt agcgtgatgc gcgacggaac catcgcctta    660

agcggcaaaa ccagcgaact gtctaccgac gacattattc aggccatcac cccagcggta    720

cgggaaaaat cgctctctgc cagccaaaaa ttatggctgg agttacctgg taaccgccca    780

caacatgccg ccggaacgcc ggtgctgaca ctggaaaatc tgaccggcga aggtttcagg    840

aatgtcagcc tgacgctcaa tgccggagaa attctgggcc tggctgggct ggtgggggcc    900

ggacgcacag aactggccga gacgctctat ggtctgcgta ctttgcgtgg cggacgcatt    960

atgctgaatg gtaaagagat caataaatta tccactggag aacgtttact gcgcggtctg   1020
```

```
gtttatctgc cggaagatcg ccagtcatcc ggactgaatc tcgatgcttc gctggcctgg   1080

aacgtctgcg cccttactca taaccttcgt ggattctggg cgaaaaccgc gaaagataat   1140

gccaccctgg aacgttatcg tcgggcgctg aatattaaat tcaaccaacc ggaacaagct   1200

gcacggacat tatccggtgg caaccagcaa aaaatcctca ttgccaaatg cttggaagct   1260

tcgccgcaag tattgattgt cgatgagccg acgcgcggcg tggatgtctc ggcccgtaat   1320

gatatctacc agctgttgcg cagcatcgcc gcacaaaatg tggctgtgct gcttatctcc   1380

tccgacctgg aagagatcga actgatggca gatcgtgtgt atgtgatgca tcagggcgaa   1440

attacccact ctgcactgac cgagcgcgat attaatgtcg agactattat gcgcgttgcc   1500

ttcggcgata gtcagcgtca ggaggcgtca tgctgaagtt tattcagaac aaccgtgaaa   1560

tcacggcact gctggcggtg gtgctgctgt ttgtattacc cggttttctc gaccgccagt   1620

atttaagtgt gcaaacgctg accatggttt atagcagcgc gcaaatcctg atcctgctgg   1680

caatgggcgc gacgctggta atgcttacgc gcaatattga tgtttcagtg ggttcgatta   1740

ccggaatgtg cgcggtgctg ttggggatgt tactgaacgc aggatattca ctacctgttg   1800

cttgtgtcgc gactttactg cttggtttgc tcgcgggatt tttcaacggt gtcctggtcg   1860

cgtggctaaa gatccctgcc attgttgcca cccttggcac gttagggttg tacagaggca   1920

tcatgttgct gtggactggc ggcaaatgga ttgaagggtt acccgccgaa ctgaaacagc   1980

tctccgcccc gctgctgctt ggcgtttcag caattggttg gttgacgata attctggtgg   2040

catttatggc ctggctgctg gcaaagacgg cgtttggacg cagtttttat gccacgggcg   2100

ataatttaca gggcgctcgt caactgggcg ttcgtactga agccattcgc attgtggcat   2160

tttcgttgaa cggctgcatg gcggcactgg cgggaattgt gtttgcttcg cagattggtt   2220

ttatccccaa ccagaccggt accgggctgg agatgaaagc aattgcagcc tgcgtgctgg   2280

gcggcattag tttgctcggt ggttccggtg cgatcattgg tgcggtactc ggcgcatggt   2340

tcctgacgca gatcgatagc gtactggtgc tgttgcgcat tccggcatgg tggaatgatt   2400

ttatcgcggg tctggttctg ctggcggtgc tggtgtttga tggacgcctg cgttgtgcgc   2460

tggaacgtaa tctacggcgg caaaaatatg cccgctttat gacgccaccg ccatccgtta   2520

aacccgcttc gtcaggtaaa aaacgggagg ccgcataatg cgtattcgct acggttggga   2580

actggctctt gccgcactgc tcgttattga gattgtcgca tttggtgcaa ttaacccgcg   2640

aatgttagat ctcaatatgt tgctgttcag caccagtgac tttatctgca ttggcattgt   2700

cgccctaccg ctaacgatgg tgattgtcag tggcgggatc gatatttcgt ttggttcgac   2760

catcggcctc tgcgccattg cattgggcgt actgtttcaa agtggtgtgc cgatgccgct   2820

ggcgatactc ctgaccttac tgctcggcgc attgtgcggg ctgatcaacg ccggattaat   2880

tatctatacc aaagttaacc cgctggtgat tacgcttggc acgctgtatc tgtttgccgg   2940

aagcgctctg ctgctttccg gtatggccgg agcgacgggg tacgaaggta ttggtggatt   3000

cccgatggcg tttacagatt tcgctaacct ggatgtgctg ggactccccg ttccgctgat   3060

tatcttcctg atatgtctcc tcgttttctg gctctggctg cataaaaccc atgccggacg   3120

taatgtgttt ttgattgggc aaagcccgcg cgtggcgctt tatagcgcga ttccagttaa   3180

ccgtacctta tgtgcgctct atgccatgac ggggctggcg tctgcggtcg ccgctgtgct   3240

gctggtatcg tattttggtt cagcacgttc cgatctcggt gcgtcgtttc tgatgcccgc   3300

catcaccgcc gtggtgcttg gcggggccaa tatttatggt ggttccggtt ccattatcgg   3360
```

```
caccgccatt gcggttttat tagtgggata tttgcaacaa ggtttgcaaa tggcaggagt   3420
gccaaatcag gtgtccagcg ccctttccgg tgcgctactt atcgtcgttg tcgtaggtcg   3480
ttccgttagc ctgcatcgcc agcaaattaa agagtggctg gcgcgtcggg ccaataaccc   3540
attgccataa aggatatctt catgacactt catcgcttta agaaaatcgc cttacttagc   3600
gctcttggca ttgccgcaat ctctatgaat gtgcaggccg cagagcgtat tgcatttatt   3660
cccaaactgg ttggcgtggg attttttacc agcggtggca acggcgcaca acaagcgggt   3720
aaagagctgg gcgttgatgt gacctacgac gggccgacag aacccagtgt ttctggtcag   3780
gtacagttga ttaataactt cgtcaatcaa ggttataacg ccattatcgt ttctgcggtt   3840
tcgcctgatg gcttgtgtcc ggcactgaaa cgcgccatgc aacgtggtgt gagagtgctg   3900
acctgggact ctgatactaa accggagtgc cgctcttact acattaatca gggaacgccc   3960
gcccagttag gaggtatgtt ggtggatatg gcggcgcgtc aggtgaataa agacaaagcc   4020
aaagtcgcgt tttctactc aagccccacc gttacggacc aaaaccagtg ggtgaaagaa   4080
gcgaaagcga aaatcgccaa agagcatcca ggctgggaaa ttgtcactac gcagtttggc   4140
tataacgatg ccactaaatc gttacaaacc gcagaaggaa tattaaaagc gtatagcgat   4200
ctcgacgcca ttatcgcccc cgatgccaac gccctgcccg ctgccgcaca agccgcagaa   4260
aacttgaaaa atgacaaagt agcgattgtc ggattcagta cgccaaatgt gatgcgcccg   4320
tatgtagagc gcggcacggt gaaagaattt ggcctgtggg atgtggttca gcaaggcaaa   4380
atttcagtgt atgtcgcgga tgcattattg aaaaaaggat caatgaaaac gggcgacaag   4440
ctggatatca agggcgtagg tcaggttgaa gtctcgccaa acagcgttca gggctatgac   4500
tacgaagcgg atggtaatgg catcgtactg ttaccggagc gcgtgatatt caacaaagag   4560
aatatcggca aatacgattt ctgatgtgca ttacttaacc ggagtaagtt atggcagatt   4620
tagacgatat taaagatggt aaagatttc gtaccgatca accgcaaaaa aatatccctt   4680
ttaccctgaa aggttgcggt gcgctggatt ggggaatgca gtcacgctta tcgcggatat   4740
ttaatccgaa aacgggtaaa accgtgatgc tggcttttga ccatggttat tttcagggac   4800
cgactaccgg acttgaacgc attgatataa atatcgcccc gctgtttgaa catgccgatg   4860
tattaatgtg tacgcgcggc attttgcgca gcgtagttcc ccctgcgacc aataggccgg   4920
tggtactgcg ggcgtcaggt gcgaactcta ttctggcgga attaagtaat gaagccgtgg   4980
cgttatcgat ggatgacgcc gtgcgcctga acagttgcgc ggtggcggcg caggtttata   5040
tcggcagcga atatgaacat cagtcgatca aaaatattat tcagctggtt gatgccggaa   5100
tgaaagtggg aatgccgacc atggccgtga ctggcgtggg caaagatatg gtgcgcgatc   5160
agcgttattt ctcgctcgcg actcgaatcg ccgctgaaat gggggcgcaa attatcaaaa   5220
cctattatgt cgaaaaaggt tttgaacgga ttgttgccgg atgtccggta cccattgtta   5280
ttgctggcgg taaaaaatta ccggagcgcg aggcgctgga aatgtgctgg caggctatcg   5340
atcagggcgc ttctggtgtg gatatggggc gtaatatttt ccagtctgac catccggtgg   5400
cgatgatgaa agccgtacag gcggtggttc accataacga aacggctgat cgggcatatg   5460
aactctatct gagtgaaaaa cagtaactgc ggatctaagg agaagaatta tgcacgtcac   5520
actggttgaa attaacgttc atgaagacaa ggttgacgag tttatcgaag tttttcgcca   5580
gaaccacctg ggctctgtac aggaagaagg caatttgcgc ttcgatgtct tacaggaccc   5640
ggaagtgaat tcgcgctttt atatctacga agcctataaa gatgaagacg cagtggcgtt   5700
ccataaaacc acgccccact acaaaacctg tgtcgcgaaa ctggaatctt taatgaccgg   5760
```

gccgcgtaaa aaacgtctgt tcaatggttt gatgccgtga atctacctcg aggtttatgg 5820
ctcgactctt taccctttca gaatcaaagt actacctgat ggcgctggat gcaggcaccg 5880
gaagtattcg ggctgtgata ttcgacctgg aaggcaatca aatagcagtg ggacaggcgg 5940
agtggcggca tctggcagta ccggacgttc ctggttctat ggaatttgat ctcaacaaaa 6000
actggcaact ggcgtgtgag tgtatgcgcc aggcgctgca caacgccggc atagccccgg 6060
agtatatcgc tgccgtttcg gcatgttcga tgcgtgaagg cattgtttta tataataatg 6120
aaggagcccc gatctgggcc tgcgccaatg tggatgccag agcggcacgc gaagttagcg 6180
aacttaaaga actgcacaac aatacctttg aaaacgaagt ttatcgcgcg accggacaaa 6240
cactggcttt aagtgccatc cccagattac tttggctggc gcaccatcgt tccgatattt 6300
accgtcaggc atcaaccatc accatgatca gcgactggct ggcctatatg ctcagcggcg 6360
aactggcggt ggatccctct aacgctggca ccacgggact tcttgatcta accacccgtg 6420
actggaaacc tgcattgctg gatatggctg gcctacgtgc cgatattctt tctcctgtca 6480
aagaaaccgg cacattgctg ggcgtggtaa gttcacaagc ggcggaactc tgcggtctga 6540
aggcgggcac tccggtggtc gttggaggag gcgacgtgca gcttggttgc cttgggttag 6600
gcgttgtgcg tccggcacaa accgcggttc ttggcggcac attctggcag caagttgtaa 6660
atttagccgc gccggtgaca gacccagaaa tgaacgtgcg cgttaatcct catgttattc 6720
ctggcatggt acaagctgaa tctataagct tttttaccgg actcaccatg cgctggttcc 6780
gcgatgcttt ctgtgccgaa gaaaaactga ttgccgaacg tttaggcatc gacacctata 6840
cgctgctgga agagatggcc agtcgggtgc cgcctgggtc gtggggcgta atgccgatct 6900
tctccgacag aatgcgcttt aaaacctggt atcacgctgc gccttccttt attaacttgt 6960
ccattgaccc ggataaatgt aacaaagcga cattgttccg tgcgctggaa gaaaatgcgg 7020
cgattgtatc agcgtgtaac ttgcagcaaa ttgctgattt ctcgaatatt catccttcat 7080
cgttagtctt tgcaggcgga ggttcaaaag ggaaattatg gagtcaaatt ctcgctgatg 7140
tctcgggatt acccgtcaat attccggtgg tcaaagaagc cactgcatta ggatgtgcca 7200
ttgcagctgg cgtcggtgcc ggaatttttt catcaatggc agaaaccgga gaacgcctgg 7260
ttcgctggga acggacgcac acaccagacc cggaaaagca tgaactttat caggattcac 7320
gcgataagtg gcaggcagtt tatcaggatc agctggggct ggttgatcat ggactgacga 7380
cgtcgttatg gaaagcgcct gggttatag 7409

<210> SEQ ID NO 3
<211> LENGTH: 54
<212> TYPE: RNA
<213> ORGANISM: Artificial
<220> FEATURE:
<223> OTHER INFORMATION: Anti-sense RNA sequence targeting expression of dam gene in Vibrio

<400> SEQUENCE: 3
uaauucaaca agaauuggga caacuccagu gaaaaguucu ucuccuuuac ucau 54

<210> SEQ ID NO 4
<211> LENGTH: 840
<212> TYPE: DNA
<213> ORGANISM: Vibrio sp.

<400> SEQUENCE: 4
atgaaaaagc aacgagcctt tcttaagtgg gcaggaggca aatacggtct ggttgaagac 60

```
atccaacgtc atttaccacc ggctcgaaag ctagttgaac cctttgttgg tgctggctcg    120

gtttttctaa ataccgacta tgaccactat ctactggcgg atattaaccc cgacctgatt    180

aatctctata acttactaaa agagcgtcct gaagagtaca tctcagaagc gaagcgctgg    240

tttgttgcag agaacaatcg caaagaagcg tacttgaata ttcgcgccga gtttaataaa    300

acggatgacg tgatgtaccg ctcgttggcg ttcctataca tgaaccgctt tggctttaat    360

ggcttatgtc gttataacaa aaaaggcggc tttaatgtcc cgtttggttc ttacaaaaag    420

ccttatttcc cagaagcgga gctagaattc tttgctgaaa aagccaagaa agcgacgttc    480

gtatgtgaag gttacccaga aacgttcagt cgagcgcgta aaggcagcgt ggtttattgc    540

gatccaccgt acgcaccgtt gtcgaacacg gcgaacttta cctcttatgc tggcaacggc    600

tttacgctgg atgatcaagc tgcattggct gatattgcag agaaagccgc aactgaacgt    660

ggtatccctg ttctgatctc aaaccatgac acgacattaa cgcgtcgcct ttatcatggt    720

gcggagctta atgtcgtaaa agtgaagcga accatcagtc gtaatggcag tggtcgtaat    780

aaagttgacg agttgctggc gctatttcgt gcacctgacg cggacaaatc tgactcttaa    840
```

<210> SEQ ID NO 5
<211> LENGTH: 46
<212> TYPE: DNA
<213> ORGANISM: Artificial Sequence
<220> FEATURE:
<223> OTHER INFORMATION: pAD-lact-for

<400> SEQUENCE: 5

```
gggaaaactg tatgtatttg atcctgctta tcgatctaga gaaaga                    46
```

<210> SEQ ID NO 6
<211> LENGTH: 45
<212> TYPE: DNA
<213> ORGANISM: Artificial Sequence
<220> FEATURE:
<223> OTHER INFORMATION: pAD-lact-rev

<400> SEQUENCE: 6

```
caagttaagg gatgcagttt acacgaacga aaatcgccat tcgcc                     45
```

<210> SEQ ID NO 7
<211> LENGTH: 40
<212> TYPE: DNA
<213> ORGANISM: Artificial Sequence
<220> FEATURE:
<223> OTHER INFORMATION: pACYC-for

<400> SEQUENCE: 7

```
tgccgggcct cttgcgggat gattgaagaa gactgccgag                          40
```

<210> SEQ ID NO 8
<211> LENGTH: 40
<212> TYPE: DNA
<213> ORGANISM: Artificial Sequence
<220> FEATURE:
<223> OTHER INFORMATION: pACYC-rev

<400> SEQUENCE: 8

```
atgctgtcgg aatggacgat atccgcttac agacaagctg                          40
```

<210> SEQ ID NO 9
<211> LENGTH: 20
<212> TYPE: DNA

-continued

```
<213> ORGANISM: Artificial Sequence
<220> FEATURE:
<223> OTHER INFORMATION: Vp-mam7-for

<400> SEQUENCE: 9

gcttagaaag catgagcgcc                                                  20


<210> SEQ ID NO 10
<211> LENGTH: 20
<212> TYPE: DNA
<213> ORGANISM: Artificial Sequence
<220> FEATURE:
<223> OTHER INFORMATION: Vp-mam7-rev

<400> SEQUENCE: 10

tgccacggta catgattggt                                                  20


<210> SEQ ID NO 11
<211> LENGTH: 20
<212> TYPE: DNA
<213> ORGANISM: Artificial Sequence
<220> FEATURE:
<223> OTHER INFORMATION: Vp-gyrB-for

<400> SEQUENCE: 11

cgagcatgcg ctaagtgttg                                                  20


<210> SEQ ID NO 12
<211> LENGTH: 20
<212> TYPE: DNA
<213> ORGANISM: Artificial Sequence
<220> FEATURE:
<223> OTHER INFORMATION: Vp-gyrB-rev

<400> SEQUENCE: 12

taacgctgac ggcttagacc                                                  20


<210> SEQ ID NO 13
<211> LENGTH: 26
<212> TYPE: DNA
<213> ORGANISM: Artificial Sequence
<220> FEATURE:
<223> OTHER INFORMATION: Vp-Ap4-for

<400> SEQUENCE: 13

atgagtaaca atataaaaca tgaaac                                           26


<210> SEQ ID NO 14
<211> LENGTH: 20
<212> TYPE: DNA
<213> ORGANISM: Artificial Sequence
<220> FEATURE:
<223> OTHER INFORMATION: Vp-Ap4-rev

<400> SEQUENCE: 14

ttgagaatac gggacgtggg                                                  20
```